(12) United States Patent
Ho

(10) Patent No.: US 6,506,936 B1
(45) Date of Patent: Jan. 14, 2003

(54) N-SUBSTITUTED ARYLSULFONYLAMINO HYDROXAMIC ACIDS USEFUL AS INHIBITORS OF C-PROTEINASE AND FOR TREATING OR PREVENTING DISORDERS RELATED TO UNREGULATED COLLAGEN PRODUCTION

(75) Inventor: Wen-Bin Ho, Los Altos, CA (US)

(73) Assignee: FibroGen, Inc., South San Francisco, CA (US)

( * ) Notice: Subject to any disclaimer, the term of this patent is extended or adjusted under 35 U.S.C. 154(b) by 0 days.

(21) Appl. No.: 09/259,183

(22) Filed: Feb. 25, 1999

(51) Int. Cl.$^7$ .................... C07C 311/46; A01K 31/18
(52) U.S. Cl. ......................... 562/621; 514/575
(58) Field of Search .................... 562/621; 514/575

(56) References Cited

U.S. PATENT DOCUMENTS

| | | |
|---|---|---|
| 5,455,258 A | 10/1995 | MacPherson et al. |
| 5,506,242 A | 4/1996 | MacPherson et al. |
| 5,552,419 A | 9/1996 | MacPherson et al. |
| 5,646,167 A | 7/1997 | MacPherson et al. |
| 5,672,615 A | 9/1997 | MacPherson et al. |

FOREIGN PATENT DOCUMENTS

| | | | |
|---|---|---|---|
| EP | 757984 | | 2/1997 |
| WO | WO 96/27583 | | 9/1996 |
| WO | WO 97/05865 | | 2/1997 |
| WO | 97/05865 | * | 2/1997 |

OTHER PUBLICATIONS

U.S. patent application Ser. No. 08/609,187, Prockop et al., filed Mar. 1, 1996.
U.S. patent application Ser. No. 09/261,671, Brenner and Ho, filed Mar. 3, 1999.
Gergel et al., 1968, *Zh. Org. Khim.* 4(1):59–63.
Ljunggren et al., 1974, "Fibrin–stabilizing factor inhibitors. 11. Monodansylated weak aliphatic diamines," *J. Med. Chem.* 17(6):649–651.
Kondo et al., "N–Arylglycine Chemotherapeutics. IV. Syntheses of 2–(*p*–Methoxyphenylamino) Acetohydroxamic Acid, 2–(*p*–Methoxyphenylamino) Acetamide, and their Derivatives," *Chemical Abstracts* 59:3824a, Columbus, OH, USA abstract (1963).

* cited by examiner

*Primary Examiner*—Robert Gerstl
(74) *Attorney, Agent, or Firm*—FibroGen, Inc.

(57) ABSTRACT

The present invention relates to a novel class of organic molecules capable of inhibiting C-proteinase, and to their use to regulate, modulate and/or inhibit abnormal collagen formation as a therapeutic approach towards the treatment of fibrotic disorders.

49 Claims, No Drawings

N-SUBSTITUTED ARYLSULFONYLAMINO HYDROXAMIC ACIDS USEFUL AS INHIBITORS OF C-PROTEINASE AND FOR TREATING OR PREVENTING DISORDERS RELATED TO UNREGULATED COLLAGEN PRODUCTION

1. FIELD OF THE INVENTION

The present invention relates to a novel class of organic molecules capable of inhibiting the enzyme C-proteinase, pharmaceutical compositions comprising the C-proteinase inhibitory compounds and methods of using the compounds and compositions to regulate, modulate and/or inhibit collagen production and/or maturation as a therapeutic approach towards the treatment or prevention of myriad diseases related to, or associated with, unregulated collagen production.

2. BACKGROUND OF THE INVENTION

Collagen Structure. At present, nineteen different types of collagens have been identified. These collagens, which include fibrillar collagen types I, II and III, are synthesized as procollagen precursor molecules which contain peptide extensions at both their amino- and carboxy-termini. These peptide extensions, referred to as "pro-regions," are designated as N- and C-propeptides, respectively. The pro-regions are typically cleaved upon secretion of the procollagen triple helical precursor molecule from the cell to yield a mature triple helical collagen molecule. Upon cleavage, the "mature" collagen molecule is capable of association, for example, into highly structured collagen fibers. See e.g., Fessler and Fessler, 1978, *Annu. Rev. Biochem.* 47:129–162; Bornstein and Traub, 1979, in: *The Proteins* (eds. Neurath, H. and Hill, R. H.), Academic Press, New York, pp. 412–632; Kivirikko et al., 1984, in: *Extracellular Matrix Biochemistry* (eds. Piez, K. A. and Reddi, A. H.), Elsevier Science Publishing Co., Inc., New York, pp. 83–118; Prockop and Kivirikko, 1984, *N. Engl. J. Med.* 311:376–383; Kuhn, 1987, in: *Structure and Function of Collagen Types* (eds. Mayne, R. and Burgeson, R. E.), Academic Press, Inc., Orlando, Fla., pp. 1–42.

Diseases Associated With The Abnormal Production of Collagen. A variety of critical diseases have been linked to inappropriate or unregulated collagen production and/or maturation. These diseases include pathological fibrosis or scarring (including endocardial sclerosis), idiopathic interstitial fibrosis, interstitial pulmonary fibrosis, perimuscular fibrosis, Symmers' fibrosis, pericentral fibrosis, hepatitis, dermatofibroma, billary cirrhosis, alcoholic cirrhosis, acute pulmonary fibrosis, idiopathic pulmonary fibrosis, acute respiratory distress syndrome, kidney fibrosis/glomerulonephritis, kidney fibrosis/diabetic nephropathy, scleroderma/systemic, scleroderma/local, keloids, hypertrophic scars, severe joint adhesions/arthritis, myelofibrosis, corneal scarring, cystic fibrosis, muscular dystrophy (duchenne's), cardiac fibrosis, muscular fibrosis/retinal separation, esophageal stricture and payronles disease. Further fibrotic disorders may be induced or initiated by surgery, including scar revision/plastic surgeries, glaucoma, cataract fibrosis, corneal scarring, joint adhesions, graft vs. host disease, tendon surgery, nerve entrapment, dupuytren's contracture, OB/GYN adhesions/fibrosis, pelvic adhesions, peridural fibrosis, restenosis. One strategy for the treatment of these diseases is to inhibit the pathological overproduction of collagen. Thus, identification and isolation of molecules which control, inhibit and/or modulate the production of collagen are of major medical interest.

Relationship Between Collagen Formation and C-Proteinase. Recent evidence suggests that C-proteinase is the essential key enzyme that catalyzes the cleavage of the C-propeptide of, for example, fibrillar collagens, including type I, type II, and type III collagen. See e.g. Prockep et al., 1998, *Matrix Biol.* 16:399–408; Lee et al., 1997, *J. Biol. Chem.* 272:19059–19066; Suzuk et al., 1996, *Development* 122:3587–3595.

C-proteinase was first observed in the culture media of human and mouse fibroblasts (Goldberg et al., 1975, *Cell* 4:45–50; Kessler and Goldberg, 1978, *Anal. Biochem.* 86:463–469), and chick tendon fibroblasts (Duskin et al., 1978, *Arch. Biochem. Biophys.* 185:326–332; Leung et al., 1979, *J. Biol. Chem.* 254:224–232). An acidic proteinase which removes the C-terminal propeptides from type I procollagen has also been identified. Davidson et al., 1979, *Eur. J. Biochem.* 100:551.

A partially purified protein having C-proteinase activity was obtained from chick calvaria in 1982. Njieha et al., 1982, *Biochemistry* 23:757–764. In 1985, chicken C-proteinase was isolated, purified and characterized from conditioned media of chick embryo tendons. Hojima et al., 1985, *J. Biol. Chem.* 260:15996–16003. Murine C-proteinase has been subsequently purified from media of cultured mouse fibroblasts. Kessler et al., 1986, *Collagen Relat. Res.* 6:249–266; Kessler and Adar, 1989, *Eur. J. Biochem.* 186:115–121. Finally, the cDNA encoding human C-proteinase has been identified (see, e.g., Takahara et al., 1994, *J. Biol. Chem.* 269:26280–26285; Li et al., 1996, *Proc. Natl. Acad. Sci. USA* 93:5127–5130; Kessler et al., 1996, *Science* 271:360–362.

C-Proteinase Inhibitors. Experiments conducted with purified forms of chick and mouse C-proteinases indicate that C-proteinase is instrumental in the formation of functional collagen fibers. Fertala et al., 1994, *J. Biol. Chem.* 269:11584. As a consequence of its critical role in collagen production and maturation, scientists have sought to identify compounds that inhibit C-proteinase. See e.g., Hojima et al., supra. Compounds identified to date include metal chelators (e.g., EDTA, phenanthroline, EGTA, basic amino acids (e.g., lysine and arginine), peptides (e.g., chymostatin, pepstatin A, and concanavalin A), proteins (e.g., $\alpha_2$-macroglobulin, ovostatin, and fetal bovine serum), metals ions (e.g., $Zn^{2+}$, $Cu^{2+}$, and $Cd^{2+}$), reducing agents (e.g., dithiothreitol), detergents (e.g., sodium dodecyl sulfate (SDS)) and certain salts and buffers (e.g., phosphate, ammonium sulfate, sodium chloride and tris hydrochloride). In contrast, microbial inhibitors such as leupeptin, phosphoramidon, antipain, bestatin, elastinal, and amastatin are considered to have weak or no effect on the activity of C-proteinase. For references discussing the various C-proteinase inhibitors identified to date, see Leung et al., supra; Ryhänen et al., 1982, *Arch. Biochem. Biophys.* 215:230–236; WO97/05865; and the references cited therein.

Matrix Metalloproteinase Hydroxamic Acid Inhibitors

C-proteinase belongs to the matrix metalloproteinase (MMP) superfamily of zinc endopeptidases which are involved in tissue remodeling. Members of the MMP family include MMP-1 (human collagenase), MMP-2 (gelatinase), and MMP-9 (human gelatinase B). See e.g. WO98/34918; Krumme et al., 1998, *FEBS Lett.* 436:209–212. The MMPs are characterized by an active site zinc ion that plays an essential role in the enzymatic activity of MMPs. Rational drug discovery efforts, involving the inhibition of MMPs, have focused on inhibitor classes that contain a functional group that can coordinate the zinc ion and thereby inactivate the target MMP. See e.g. Krumme et al., supra. One such inhibitor class are hydroxamic acids. As revealed by the x-ray crystal structure determination of hydroxamic acid:MMP cocrystals, the hydroxamic acid coordinates the active site zinc in a bidentate manner via the hydroxyl and carbonyl oxygens of the hydroxamic group. See Grams et al., 1995, *Biochem.* 34:14012–14020; Bode et al., 1994, *EMBO J.*, 13:1263–1269. Despite their potent affinity as zinc coordinators, hydroxamic acids demonstrate a considerable degree of specificity within the MMP family. Thus a potent inhibitor of MMP-1 (human collagenase) may have only minimal potency against another MMP such as C-proteinase. Thus the development of potent hydroxamic acid inhibitors against a particular MMP requires considerable research effort and experimentation.

Development of Compounds to Inhibit C-Proteinase Activity. In view of its essential role in the formation and maturation of collagen, C-proteinase provides an ideal therapeutic target towards the treatment or prevention of disorders related to, or associated with, unregulated collagen production or maturation. However, none of the C-proteinase inhibitors identified to date have proven to be clinically effective therapeutics for the treatment of collagen-related diseases. Accordingly, there remains a need in the art for compounds that are specific and potent inhibitors of C-proteinase, especially C-proteinase inhibitory compounds which provide clinically relevant benefits in the treatment or prevention of diseases associated with unregulated collagen production and/or maturation.

3. SUMMARY OF THE INVENTION

In one aspect, the present invention provides a novel class of organic molecules that are potent and/or selective inhibitors of C-proteinase. As a consequence of this activity, the compounds of the invention are capable of modulating, regulating or inhibiting collagen production or maturation by affecting C-proteinase activity.

The compounds of the invention are generally N-substituted arylsulfonylamino hydroxamic acids. In one embodiment, the compounds of the invention are N-aryl substituted arylsulfonylamino hydroxamic acids having the structural formula (I):

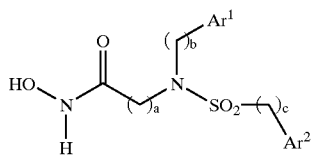

(I)

or pharmaceutically acceptable salts thereof, wherein:

a is an integer from 1 to 4;

b is an integer from 0 to 4;

c is an integer from 0 to 4;

$Ar^1$ is selected from the group consisting of $(C_5–C_{20})$ aryl, $(C_5–C_{20})$ aryl independently substituted with one or more $Y^1$, 5–20 membered heteroaryl and 5–20 membered heteroaryl independently substituted with one or more $Y^1$;

$Ar^2$ is selected from the group consisting of $(C_5–C_{20})$ aryl, $(C_5–C_{20})$ aryl independently substituted with one or more $Y^2$, 5–20 membered heteroaryl and 5–20 membered heteroaryl independently substituted with one or more $Y^2$;

each $Y^1$ is independently selected from the group consisting of an electron-donating functional group, an electron-withdrawing functional group, and a lipophilic functional group; and each $Y^2$ is independently selected from the group consisting of a functional group having an acidic hydrogen, a functional group capable of participating in a hydrogen bond, a polar functional group, an electron-withdrawing functional group, an electron-donating functional group, and a lipophilic functional group, with the provisos that:

(i) when a and b are each one, c is zero and $Ar^2$ is 4'-methoxyphenyl, then $Ar^1$ is other than phenyl, 4'-flourophenyl, 4'-chlorophenyl, 4'-trifluoromethylphenyl or 4'-methoxyphenyl; (ii) when a and b are each one, c is zero and $Ar^2$ is phenyl, then $Ar^1$ is other than 4'-chlorophenyl;

(iii) when a is two, b and c are each zero and $Ar^1$ is phenyl, then $Ar^2$ is other than 4'-chlorophenyl or 4'-bromophenyl; and (iv) when a and b are each one, c is zero then $Ar^1$ is other than carbocyclic aryl-lower alkyl, carbocyclic aryl, heterocyclic aryl, biaryl, biaryl-lower alkyl, heterocyclic aryl-lower alkyl, (N-aryl-lower alkylpiperazino)-lower alkyl wherein, in proviso (iv), aryl represents monocyclic or bicyclic aryl, carbocyclic aryl represents monocyclic or bicyclic carbocyclic aryl and heterocyclic aryl represents monocyclic or bicyclic heterocyclic aryl.

In another embodiment, the compounds of the invention are N-aryl substituted arylsulfonylamino hydroxamic acids having the structural formula (II):

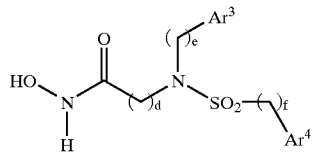

(II)

or pharmaceutically acceptable salts thereof, wherein:

d is an integer from 1 to 4;

e is an integer from 0 to 4;

f is an integer from 0 to 4;

$Ar^3$ is selected from the group consisting of $(C_5–C_{20})$ aryl, $(C_5–C_{20})$ aryl independently substituted with one or more $Y^3$, 5–20 membered heteroaryl and 5–20 membered heteroaryl independently substituted with one or more $Y^3$;

$Ar^4$ is selected from the group consisting of $(C_5–C_{20})$ aryl, $(C_5–C_{20})$ aryl independently substituted with one or more $Y^4$, 5–20 membered heteroaryl and 5–20 membered heteroaryl independently substituted with one or more $Y^4$;

each $Y^3$ is independently selected from the group consisting of —R', —OR', —SR', —NR'R', —NO, —$NO_2$, —CN, -halogen, methyl, —$SO_2NH_2$ and trihalomethyl;

each $Y^4$ is independently selected from the group consisting of —R', —OR', —OR", —SR', —SR", —NR'R', —$NO_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —$SO_2$R', —$SO_2$R", —NR'—$SO_2$—R', —NR'—C(O)—NR'R', tetrazol-5-yl, —NR'—C(O)—OR', —C(NR'R')=NR', —S(O)—R', —S(O)—R", and —NR'—C(S)—NR'R';

each R' is independently selected from the group consisting of —H, ($C_1$–$C_8$) alkyl, ($C_2$–$C_8$) alkenyl, and ($C_2$–$C_8$) alkynyl; and each R" is independently selected from the group consisting of ($C_5$–$C_{20}$) aryl and ($C_5$–$C_{20}$) aryl independently substituted with one or more —OR', —SR', —NR'R', —NO$_2$, —CN, halogen or trihalomethyl groups, with the provisos that:
(i) when d and e are each one, f is zero and $Ar^4$ is 4'-methoxyphenyl, then $Ar^3$ is other than phenyl, 4'-fluorophenyl, 4'-chlorophenyl, 4'-trifluoromethylphenyl or 4'-methoxyphenyl;
(ii) when d and e are each one, f is zero and $Ar^4$ is phenyl, then $Ar^3$ is other than 4'-chlorophenyl;
(iii) when d is two, d and e are each zero and $Ar^3$ is phenyl, then $Ar^4$ is other than 4'-chlorophenyl or 4'-bromophenyl; and
(iv) when d and e are each one, f is zero then $Ar^3$ is other than carbocyclic aryl-lower alkyl, carbocyclic aryl, heterocyclic aryl, biaryl, biaryl-lower alkyl, heterocyclic aryl-lower alkyl, (N-aryl-lower alkylpiperazino)-lower alkyl wherein, in proviso (iv), aryl represents monocyclic or bicyclic aryl, carbocyclic aryl represents monocyclic or bicyclic carbocyclic aryl and heterocyclic aryl represents monocyclic or bicyclic heterocyclic aryl.

In another embodiment, the compounds of the invention are N-cycloalkyl or N-heterocycloalkyl substituted arylsulfonylamino hydroxamic acids having the structural formula (III):

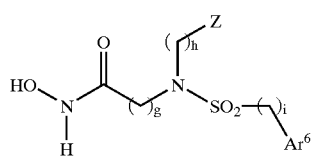

(III)

or pharmaceutically acceptable salts thereof, wherein:
g is an integer from 1 to 4;
h is an integer from 0 to 4;
i is an integer from 0 to 4;
Z is selected from the group consisting of ($C_3$–$C_{10}$) cycloalkyl, ($C_3$–$C_{10}$) cycloalkyl independently substituted with one or more $Y^5$, 3–10 membered heterocycloalkyl and 3–10 membered heterocycloalkyl independently substituted with one or more $Y^5$;
$Ar^6$ is selected from the group consisting of ($C_5$–$C_{20}$) aryl, ($C_5$–$C_{20}$) aryl independently substituted with one or more $Y_6$, 5–20 membered heteroaryl and 5–20 membered heteroaryl independently substituted with one or more $Y^6$;
each $Y^5$ is independently selected from the group consisting of a lipophilic functional group, ($C_5$–$C_{20}$) aryl, ($C_6$–$C_{26}$) alkaryl, 5–20 membered heteroaryl and 6–26 membered alk-heteroaryl;
each $Y^6$ is independently selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', tetrazol-5-yl, —NR'—C(O)—OR', —C(NR'R')=NR', —S(O)—R', —S(O)—R", and —NR'—C(S)—NR'R'; and R' and R" are as previously defined for structure (II), with the proviso that when g and h is 1, i is 0, and $Ar^6$ is phenyl, then Z is other than $C_3$–$C_7$-cycloalkyl, $C_3$–$C_7$-cycloalkyl-lower alkyl, N-lower alkyl-piperazino-lower alkyl, (morpholino, thiomorpholino, piperidino, pyrrolidino, piperidyl or N-lower alkylpiperidyl)-lower alkyl.

In another embodiment, the compounds of the invention are N' substituted urea-arylsulfonylamino hydroxamic acids having the structural formula (IV):

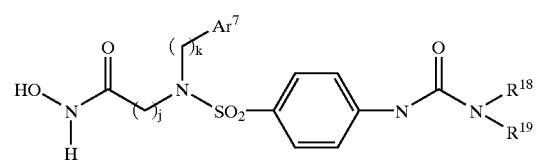

(IV)

or pharmaceutically acceptable salts thereof, wherein:
j is an integer from 1 to 4;
k is an integer from 0 to 4;
$Ar^7$ is selected from the group consisting of ($C_5$–$C_{20}$) aryl, ($C_5$–$C_{20}$) aryl independently substituted with one or more $Y^7$, 5–20 membered heteroaryl and 5–20 membered heteroaryl independently substituted with one or more $Y^7$;
$R^{18}$ and $R^{19}$ are each independently selected from the group consisting of hydrogen, ($C_1$–$C_8$) alkyl, ($C_2$–$C_8$) alkenyl, ($C_2$–$C_8$) alkynyl, ($C_3$–$C_{10}$) cycloalkyl, ($C_5$–$C_{20}$) aryl, ($C_5$–$C_{20}$) substituted aryl, ($C_6$–$C_{26}$) alkaryl, ($C_6$–$C_{26}$) substituted alkaryl, 5–20 membered heteroaryl, 5–20 membered substituted heteroaryl, 6–26 membered alk-heteroaryl, and 6–26 membered substituted alk-heteroaryl; and
each $Y^7$ is independently selected from the group consisting of an electron-donating functional group, an electron-withdrawing functional group, and a lipophilic functional group.

In another embodiment, the compounds of the present invention are substituted urea compounds having the structural formula (V):

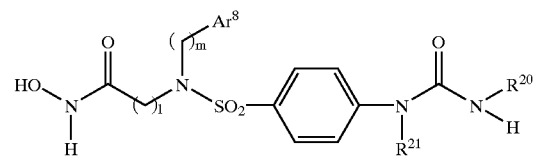

(V)

or pharmaceutically acceptable salts thereof, wherein:
l is an integer from 1 to 4;
m is an integer from 0 to 4;
$Ar^8$ is selected from the group consisting of ($C_5$–$C_{20}$) aryl, ($C_5$–$C_{20}$) aryl independently substituted with one or more $Y^8$, 5–20 membered heteroaryl and 5–20 membered heteroaryl independently substituted with one or more $Y^8$;
$R^{20}$ is selected from the group consisting of hydrogen, ($C_1$–$C_8$) alkyl, ($C_2$–$C_8$) alkenyl, ($C_2$–$C_8$) alkynyl, ($C_3$–$C_{10}$) cycloalkyl, ($C_5$–$C_{20}$) aryl, ($C_5$–$C_{20}$) substituted aryl, ($C_6$–$C_{26}$) alkaryl, ($C_6$–$C_{26}$) substituted alkaryl, 5–20 membered heteroaryl, 5–20 membered substituted heteroaryl, 6–26 membered alk-heteroaryl, and 6–26 membered substituted alk-heteroaryl;

$R^{21}$ is independently selected from the group consisting of hydrogen, ($C_1$–$C_8$) alkyl, ($C_2$–$C_8$) alkenyl, and ($C_2$–$C_8$) alkynyl; and each $Y^8$ is independently selected from the group consisting of an electron-donating functional group, an electron-withdrawing functional group, and a lipophilic functional group.

In another embodiment, the compounds of the present invention are benzoyl substituted hydroxamic acids having the structural formula (VI):

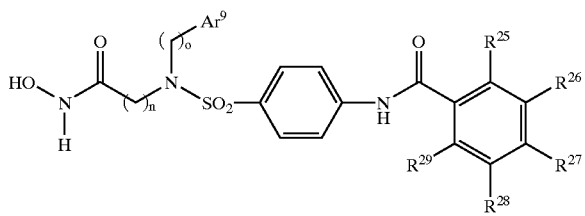

(VI)

or pharmaceutically acceptable salts thereof, wherein:

n is an integer from 1 to 4;

o is an integer from 0 to 4;

$Ar^9$ is selected from the group consisting of ($C_5$–$C_{20}$) aryl, ($C_5$–$C_{20}$) aryl independently substituted with one or more $Y^9$, 5–20 membered heteroaryl and 5–20 membered heteroaryl independently substituted with one or more $Y^9$; and each $R^{25}$, $R^{26}$, $R^{27}$, $R^{28}$, $R^{29}$ and $Y^9$ is independently selected from the group consisting of an electron-donating functional group, an electron-withdrawing functional group, and a lipophilic functional group.

In a final embodiment, the compounds of the invention are benzylsulfonyl substituted hydroxamic acids having the structural formula (VII):

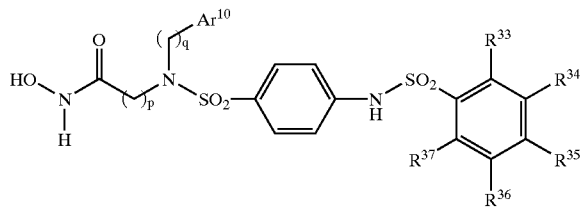

(VII)

or pharmaceutically acceptable salts thereof, wherein:

p is an integer from 1 to 4;

q is an integer from 0 to 4;

$Ar^{10}$ is selected from the group consisting of ($C_5$–$C_{20}$) aryl, ($C_5$–$C_{20}$) aryl independently substituted with one or more $Y^8$, 5–20 membered heteroaryl and 5–20 membered heteroaryl independently substituted with one or more $Y^9$; and each $R^{33}$, $R^{34}$, $R^{35}$, $R^{36}$, $R^{37}$ and $Y^{10}$ is independently selected from the group consisting of an electron-donating functional group, an electron-withdrawing functional group, and a lipophilic functional group.

In another aspect, the present invention provides pharmaceutical compositions comprising a therapeutically effective amount of one or more of the above-described compounds and a pharmaceutically acceptable carrier, diluent or excipient. Such a composition can be used in the methods of the invention to inhibit, regulate or modulate the production or maturation of collagen by inhibiting C-proteinase activity and to treat or prevent a variety of collagen-related disorders.

In yet another aspect, the invention provides methods of inhibiting C-proteinase activity. The method involves contacting the enzyme C-proteinase, or an active fragment or derivative thereof, with an amount of a compound or composition according to the invention effective to block collagen production. Methods of inhibiting C-proteinase in vivo can be used to inhibit, regulate or modulate collagen production or maturation as a therapeutic approach towards the treatment or prevention of disorders related to, or associated with, unregulated collagen production or maturation.

In a final aspect, the present invention provides methods for the treatment or prevention of disorders related to, or associated with, inappropriate or unregulated collagen production or maturation. The method involves administering to an animal subject, including a human, an amount of a compound according to the invention, or a pharmaceutical composition thereof, effective to treat or prevent the particular collagen-related disorder.

Disorders which can be treated or prevented according to the methods of the invention include, but are not limited to, rheumatoid arthritis, scleroderma, pathological fibrosis or scarring.

4. DEFINITIONS

As used herein, the following terms shall have the following meanings:

"C-proteinase:" refers to an enzyme capable of processing collagen molecules, derivatives or fragments of collagen molecules or precursors of collagen molecules, collagen derivatives or collagen fragments by cleaving the amino acid sequence —Ala↓Asp-Asp—, —Gly↓Asp-Glu— and/or —Ala↓Asp-Gln— at the position marked with "↓". The term "C-proteinase" includes human C-proteinase as well as derivatives, analogs, fragments and variants thereof capable of processing collagen molecules as described above.

"Alkyl:" refers to a saturated branched, straight chain or cyclic hydrocarbon radical. Typical alkyl groups include, but are not limited to, methyl, ethyl, propyl, isopropyl, cyclopropyl, butyl, isobutyl, t-butyl, cyclobutyl, pentyl, isopentyl, cyclopentyl, hexyl, cyclohexyl and the like. In preferred embodiments, the alkyl groups are ($C_1$–$C_8$) alkyl, more preferably ($C_1$–$C_6$) alkyl and most preferably ($C_1$–$C_3$) alkyl.

"Alkenyl:" refers to an unsaturated branched, straight chain or cyclic hydrocarbon radical having at least one carbon-carbon double bond. The radical may be in either the cis or trans conformation about the double bond(s). Typical alkenyl groups include, but are not limited to, ethenyl, vinylidene, propenyl, propylidene, isopropenyl, isopropylidene, butenyl, butenylidene, isobutenyl, tert-butenyl, cyclobutenyl, pentenyl, isopentenyl, cyclopentenyl, hexenyl, cyclohexenyl and the like. In preferred embodiments, the alkenyl group is ($C_2$–$C_8$) alkenyl, more preferably ($C_2$–$C_6$) alkenyl and most preferably ($C_2$–$C_3$) alkenyl.

"Alkynyl:" refers to an unsaturated branched, straight chain or cyclic hydrocarbon radical having at least one carbon-carbon triple bond. Typical alkynyl groups include, but are not limited to, ethynyl, propynyl, butynyl, isobutynyl, pentynyl, hexynyl and the like. In preferred embodiments, the alkynyl group is ($C_2$–$C_8$) alkynyl, more preferably ($C_2$–$C_6$) and most preferably ($C_2$–$C_3$) alkynyl.

"Cycloalkyl:" refers to a cyclic or polycyclic saturated or unsaturated hydrocarbon radical. Typical cycloalkyl groups include, but are not limited to, cyclopropanyl, cyclobutanyl, cyclopentanyl, cyclohexanyl and higher cycloalkyls, adamantyl, cubanyl, prismanyl and higher polycylicalkyls, etc. In preferred embodiments, the cycloalkyl is ($C_3$–$C_{10}$) cycloalkyl. Particularly preferred cycloalkyls are cyclohexanyl and adamantyl.

"Heterocycloalkyl:" refers to a cycloalkyl moiety wherein one of the ring carbon atoms is replaced with another atom such as N, P, O, S, As, Ge, Se, Si, Te, etc. Typical heterocycloalkyls include, but are not limited to, imidazolidyl, piperazyl, piperidyl, pyrazolidyl, pyrrolidyl, quinuclidyl, etc. In preferred embodiments, the cycloheteroalkyl is 5–10 membered. Particularly preferred cycloheteroalkyls are morpholino, tetrahydrofuryl, and pyrrolidyl.

"Substituted Cycloalkyl or Cylcoheteroalkyl:" refers to a cycloalkyl or cycloheteroalkyl radical wherein one or more hydrogen atoms are each independently replaced with another substituent. Typical substituents include, but are not limited to, —R, —OR, —SR, —NRR, —CN, —NO$_2$, —C(O)R, —C(O)OR, —C(O)NRR, —C(NRR)=NR, —C(O)NROR, —C(NRR)=NOR, —NR—C(O)R, -tetrazol-5-yl, —NR—SO$_2$—R, —NR—C(O)—NRR, —NR—C(O)—OR, -halogen and -trihalomethyl where each R is independently —H, ($C_1$–$C_8$) alkyl, ($C_2$–$C_8$) alkenyl, ($C_2$–$C_8$) alkynyl, ($C_5$–$C_{20}$) aryl, ($C_6$–$C_{26}$) alkaryl, 5–20 membered heteroaryl, and 6–26 membered alk-heteroaryl as defined herein.

"Aryl:" refers to an unsaturated cyclic hydrocarbon radical having a conjugated n electron system. Typical aryl groups include, but are not limited to, penta-2,4-dienyl, phenyl, naphthyl, aceanthrylyl, acenaphthyl, anthracyl, azulenyl, chrysenyl, indacenyl, indanyl, ovalenyl, perylenyl, phenanthrenyl, phenalenyl, picenyl, pyrenyl, pyranthrenyl, rubicenyl and the like. In preferred embodiments, the aryl group is ($C_5$–$C_{20}$) aryl, more preferably ($C_5$–$C_{10}$) aryl and most preferably phenyl.

"Substituted Aryl:" refers to an aryl radical wherein one or more hydrogen atoms are each independently replaced with another substituent. Typical substituents include, but are not limited to, —R, —OR, —SR, —NRR, —CN, —NO$_2$, —C(O)R, —C(O)OR, —C(O)NRR, —C(NRR)=NR, —C(O)NROR, —C(NRR)=NOR, —NR—C(O)R, —NR—C(O)—NRR, —NR—C(O)—OR, —NR—SO$_2$—R, -tetrazol-5-yl, -halogen and -trihalomethyl where each R is independently —H($C_1$–$C_8$) alkyl, ($C_2$–$C_8$) alkenyl, ($C_2$–$C_8$) alkynyl, ($C_5$–$C_{20}$) aryl, ($C_6$–$C_{26}$) alkaryl, heteroaryl and alk-heteroaryl as defined herein.

"Alkaryl:" refers to a straight-chain ($C_1$–$C_8$) alkyl, ($C_2$–$C_8$) alkenyl or ($C_2$–$C_8$) alkynyl group wherein one of the hydrogen atoms bonded to the terminal carbon is replaced with an ($C_5$–$C_{20}$) aryl moiety. Alkaryl also refers to a branched-chain alkyl, alkenyl or alkynyl group wherein one of the hydrogen atoms bonded to a terminal carbon is replaced with an aryl moiety. Typical alkaryl groups include, but are not limited to, benzyl, benzylidene, benzylidyne, benzenobenzyl, naphthalenobenzyl and the like. In preferred embodiments, the alkaryl group is ($C_6$–$C_{26}$) alkaryl, i.e., the alkyl, alkenyl or alkynyl moiety of the alkaryl group is ($C_1$–$C_6$) and the aryl moiety is ($C_5$–$C_{20}$). In particularly preferred embodiments the alkaryl group is ($C_6$–$C_{13}$), i.e., the alkyl, alkenyl or alkynyl moiety of the alkaryl group is ($C_1$–$C_3$) and the aryl moiety is ($C_5$–$C_{10}$).

"Substituted Alkaryl:" refers to an alkaryl radical wherein one or more hydrogen atoms on the aryl moiety are each independently replaced with another substituent. Typical substituents include, but are not limited to, —OR, —SR, —NRR, —CN, —NO$_2$, —C(O)R, —C(O)OR, —C(O)NRR, —C(S)NRR, —C(NRR)NR, —NR—C(O)R, —C(NRR)=NOR, —C(O)NROR, —NR—C(O)—NRR, -halogen and -trihalomethyl, where each R is independently —H, alkyl, alkenyl, alkynyl, aryl, alkaryl, heteroaryl or alk-heteroaryl as defined herein.

"Heteroaryl:" refers to an aryl moiety wherein one or more carbon atoms has been replaced with another atom, such as N, P, O, S, As, Ge, Se, Si, Te, etc. Typical heteroaryl groups include, but are not limited to acridarsine, acridine, arsanthridine, arsindole, arsindoline, benzodioxole, benzothiadiazole, carbazole, β-carboline, chromane, chromene, cinnoline, furan, imidazole, indazole, indole, isoindole, indolizine, isoarsindole, isoarsinoline, isobenzofuran, isochromane, isochromene, isoindole, isophosphoindole, isophosphinoline, isoquinoline, isothiazole, isoxazole, naphthyridine, perimidine, phenanthridine, phenanthroline, phenazine, phosphoindole, phosphinoline, phthalazine, piazthiole, pteridine, purine, pyran, pyrazine, pyrazole, pyridazine, pyridine, pyrimidine, pyrrole, pyrrolizine, quinazoline, quinoline, quinolizine, quinoxaline, selenophene, tellurophene, thiazopyrrolizine, thiophene and xanthene. In preferred embodiments, the heteroaryl group is a 5–20 membered heteroaryl, with 5–10 membered heteroaryl being particularly preferred.

"Substituted Heteroaryl:" refers to a heteroaryl radical wherein one or more hydrogen atoms are each independently replaced with another substituent. Typical substituents include, but are not limited to, —R, —OR, —SR, —NRR, —CN, —NO$_2$, —C(O)R, —C(O)OR, —C(O)NRR, —C(NRR)=NR, —C(O)NROR, —C(NRR)=NOR, —NR—C(O)R, —NR—C(O)—NRR, —NR—C(O)—OR, —NR—SO$_2$—R, -tetrazol-5-yl, -halogen and -trihalomethyl where each R is independently —H, alkyl, alkenyl, alkynyl, aryl, alkaryl, heteroaryl and alk-heteroaryl as defined herein.

"Alk-heteroaryl:" refers to a straight-chain alkyl, alkenyl or alkynyl group where one of the hydrogen atoms bonded to a terminal carbon atom is replaced with a heteroaryl moiety. In preferred embodiments, the alkheteroaryl group is a 6–26 membered alkheteroaryl, i.e., the alkyl, alkenyl or alkynyl moiety of the alk-heteroaryl is ($C_1$–$C_6$) and the heteroaryl moiety is a 5–20-membered heteroaryl. In particularly preferred embodiments, the alk-heteroaryl is a 6–13 membered alk-heteroaryl, i.e., the alkyl, alkenyl or alkynyl moiety is ($C_1$–$C_3$) and the heteroaryl moiety is a 5–10 membered heteroaryl.

"Substituted Alk-heteroaryl:" refers to an alk-heteroaryl radical wherein one or more hydrogens on the heteroaryl moiety are each independently replaced with another substituent. Typical substituents include, but are not limited to, —OR, —SR, —NRR, —CN, —NO$_2$, —C(O)R, —C(O)OR, —C(O)NRR, —C(S)NRR, —C(NRR)=NR, —NR—C(O)—NRR, —NR—C(O)—OR, —NR—SO$_2$—R, -tetrazol-5-yl, -halogen and -trihalomethyl, where each R is independently —H, alkyl, alkenyl, alkynyl, aryl, alkaryl, heteroaryl or alk-heteroaryl as defined herein.

"Electron-donating functional group" An electron-donating functional group is any functional group that produces an inductive field effect by presenting a partial negative charge to the parent group that the functional group is attached to. As used herein, representative electron-donating groups include, but are not limited to, —Cl, —R, —OR, —SR, and —NRR, where each R is independently —H, $(C_1–C_8)$ alkyl, $(C_2–C_8)$ alkenyl or $(C_2–C_8)$ alkynyl.

"Electron-withdrawing functional group" An electron-withdrawing functional group is any functional group that produces an inductive field effect by presenting a partial positive charge to the parent group that the functional group is attached to. As used herein, representative electron-withdrawing functional groups include, but are not limited to, —F, —NO, —NO$_2$, —CN, -trihalomethyl, —SO$_2$NHR, —SO$_2$R, and —S(O)R, where each R is independently —H, $(C_1–C_8)$ alkyl, $(C_2–C_8)$ alkenyl or $(C_2–C_8)$ alkynyl.

"Lower Alkyl" defines branched or unbranched organic compounds with up to and including 7, preferably up to and including 4 and advantageously one or two carbon atoms.

"A lower alkyl group" is branched or unbranched and contains 1 to 7 carbon atoms, preferably 1–4 carbon atoms, and represents for example methyl, ethyl, propyl, butyl, isopropyl, isobutyl and the like.

"Carbocylic aryl" represents monocyclic or bicyclic aryl, for example phenyl or phenyl mono-, di- or tri-substituted by one, two or three radicals selected from lower alkyl, lower alkoxy, hydroxy, halogen, cyano and trifluoromethyl or phenyl disubstituted on adjacent carbon atoms by lower alkylenedioxy, such as methylenedioxy; or 1- or 2-naphthyl. Preferred is phenyl or phenyl monosubstituted by lower alkoxy, halogen or trifluoromethyl.

"Heterocyclic aryl" represents monocyclic or bicyclic heteroaryl, for example pyridyl, quinolyl, isoquinolyl, benzothienyl, benzofuranyl, benzopyranyl, benzothiopyranyl, furanyl, pyrrolyl, thiazolyl, oxazolyl, isoxazolyl, triazolyl, tetrazolyl, pyrrazolyl, imidazolyl, thienyl, or any said radical substituted by lower alkyl or halogen. Pyridyl represents 2-, 3- or 4-pyridyl, advantageously 2- or 3-pyridyl. Thienyl represents 2- or 3-thienyl, advantageously 2-thienyl. Quinolyl represents preferably 2-, 3- or 4-quinolyl, advantageously 2-quinolyl. Isoquionolyl represents preferably 1-, 3- or 4-isoquinolyl. Benzopyranyl, benzothiopyranyl represents preferably 3-benzopyranyl or 3-benzothiopyranyl, respectively. Thiazolyl represents preferably 2- or 4-thiazolyl, advantageously 4-thiazolyl. Triazolyl is preferably 1-, 2- or 5-(1,2,4-triazolyl). Tetrazolyl is preferably 5-tetrazolyl. Imidazolyl is preferably 4-imidazolyl.

"Biaryl" is preferably carbocyclic biaryl, e.g. biphenyl, namely 2, 3 or 4-biphenyl, advantageously 4-biphenyl, each optionally substituted by e.g. lower alkyl, lower alkoxy, halogen, trifluoromethyl or cyano.

"$C_3–C_7$-cycloalkyl" represents a saturated cyclic hydrocarbon optionally substituted by lower alkyl which contains 3 to 7 ring carbons and is advantageously cyclopentyl or cyclohexyl optionally substituted by lower alkyl.

"Carbocyclic aryl-lower alkyl" represents preferably straight chain or branched aryl-$C_1–C_4$ alkyl in which carbocyclic aryl has meaning as defined above, e.g. benzyl or phenyl-(ethyl, propyl or butyl), each unsubstituted or substituted on the phenyl ring as defined under carbocyclic aryl above, advantageously optionally substituted benzyl.

"Heterocyclic aryl-lower alkyl" represents preferably straight chain or branched heterocyclic aryl-$C_1–C_4$-alkyl in which heterocyclic aryl has meaning as defined above, e.g. 2-, 3-, or 4-pyridylmethyl or (2-, 3-, or 4-pyridyl)-(ethyl, propyl or butyl); or 2- or 3-thienylmethyl or (2- or 3-thienyl)-(ethyl, propyl or butyl); 2-, 3-, or 4-quinolylmethyl or (2-, 3- or 4-quinolyl)-(ethyl, propyl or butyl); or 2- or 4-thiazolylmethyl or (2- or 4-thiazolyl)-(ethyl, propyl or butyl); and the like.

"Cycloalkyl-lower alkyl" represents preferably (cyclopentyl- or cyclohexyl)-(methyl or ethyl), and the like.

"Biaryl-lower alkyl" represents preferably 4-biphenylyl-(methyl or ethyl) and the like.

5. DETAILED DESCRIPTION OF THE INVENTION

The present invention provides a novel class of organic compounds capable of inhibiting the enzyme C-proteinase, pharmaceutical compositions comprising one or more of such compounds, and methods of using the compounds to inhibit, regulate or modulate collagen formation or maturation as a therapeutic approach towards the treatment or prevention of diseases related to, or associated with, unregulated collagen production or maturation.

5.1 The Compounds

In one embodiment, compounds which are capable of inhibiting C-proteinase according to the invention, and which can therefore be used in methods to inhibit, modulate or regulate collagen production or maturation or to treat or prevent diseases related to, or associated with, unregulated collagen production or maturation are generally N-aryl substituted arylsulfonylamino hydroxamic acids having the structural formula (I):

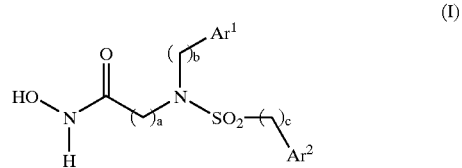

or pharmaceutically acceptable salts thereof, wherein:
a is an integer from 1 to 4;
b is an integer from 0 to 4;
c is an integer from 0 to 4;
Ar$^1$ is selected from the group consisting of $(C_5–C_{20})$ aryl, $(C_5–C_{20})$ aryl independently substituted with one or more Y$^1$, 5–20 membered heteroaryl and 5–20 membered heteroaryl independently substituted with one or more Y$^2$;
Ar$^2$ is selected from the group consisting of $(C_5–C_{20})$ aryl, $(C_5–C_{20})$ aryl independently substituted with one or more Y$^2$, 5–20 membered heteroaryl, and 5–20 membered heteroaryl independently substituted with one or more Y$^2$;
each Y$^1$ is independently selected from the group consisting of an electron-donating functional group, an electron-withdrawing functional group, and a lipophilic functional group; and
each Y$^2$ is independently selected from the group consisting of a functional group having an acidic hydrogen, a functional group capable of participating in a hydrogen bond, a polar functional group, an electron-withdrawing functional group, an electron-donating functional group, and a lipophilic functional group;
with the provisos that:
(i) when a and b are each one, c is zero and Ar$^2$ is 4'-methoxyphenyl, then Arl is other than phenyl, 4'-flourophenyl, 4'-chlorophenyl, 4'-trifluoromethylphenyl or 4'-methoxyphenyl; (ii) when a and b are each one, c is zero and $Ar^2$ is phenyl, then $Ar^1$ is other than 4'-chlorophenyl;

(iii) when a is two, b and c are each zero and $Ar^1$ is phenyl, then $Ar^2$ is other than 41-chlorophenyl or 4'-bromophenyl; and (iv) when a and b are each one, c is zero then $Ar^1$ is other than carbocyclic aryl-lower alkyl, carbocyclic aryl, heterocyclic aryl, biaryl, biaryl-lower alkyl, heterocyclic aryl-lower alkyl, or (N-aryl-lower alkylpiperazino)-lower alkyl, wherein, in proviso (iv), aryl represents monocyclic or bicyclic aryl, carbocyclic aryl represents monocyclic or bicyclic carbocyclic aryl and heterocyclic aryl represents monocyclic or bicyclic heterocyclic aryl.

Typical electron-donating functional groups that are independently selected for $Y^1$ and $Y^2$ in compounds of formula (I) include, but are not limited to, —Cl, —R, —OR, —SR, —NRR, where each R is independently —H, $(C_1-C_8)$ alkyl, $(C_2-C_8)$ alkenyl or $(C_2-C_8)$ alkynyl. Particularly preferred electron-donating groups are —Cl, and —$OCH_3$.

Functional groups having an acidic hydrogen that are suitable for $Y^2$ in compounds of formula (I) include, but are not limited to, —COOH, —$SO_3H$, —P(O) $(OH)_2$, —C(O)—NH—OH,

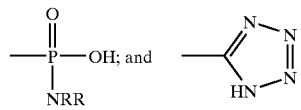

where each R is independently H, $(C_1-C_8)$ alkyl, $(C_2-C_8)$ alkenyl, $(C_2-C_8)$ alkynyl, $(C_5-C_{20})$ aryl, $(C_6-C_{26})$ alkaryl, 5–20 membered heteroaryl, and 6–26 membered alk-heteroaryl as defined herein. Functional groups capable of participating in a hydrogen bond that are suitable for $Y^2$ in compounds of formula (I) include both hydrogen-donating groups and hydrogen accepting groups. Typical hydrogen donating groups independently selected for $Y^2$ include, but are not limited to, —C(NHR)=N—OH, —NH—C(O)R, —NH—C(O)—NRR, —C(S)NHR, —C(O)NHR, —$CO_2H$, —$NH_2$, —C(NHR)=NR, —NH—C(O)—OR, —NH—$SO_2$—R, —NH—C(S)—NRR where each R is independently —H, $(C_1-C_8)$ alkyl, $(C_2-C_8)$ alkenyl, $(C_2-C_8)$ alkynyl, $(C_5-C_{20})$ aryl, $(C_6-C_{26})$ alkaryl, 5–20 membered heteroaryl, and 6–26 membered alk-heteroaryl as defined herein. Typical hydrogen accepting groups selected for $Y^2$ include, but are not limited to, —$CO_2R$, $SO_2R$, —OR, SR, C(O)—R, —C(O)NRR, —C(S)NRR, —NH—C(O)R, —NR—C(O)—NRR, —NR—C(S)—NRR, and —S(O)—R where each R is independently —H, $(C_1-C_8)$ alkyl, $(C_2-C_8)$ alkenyl, $(C_2-C_8)$ alkynyl, $(C_5-C_{20})$ aryl, $(C_6-C_{26})$ alkaryl, 5–20 membered heteroaryl and 6–26 membered alk-heteroaryl as defined herein. Typical polar functional groups selected for $Y^2$ in compounds of formula (I) include, but are not limited to —C≡N, —OR, and —SR where R is independently —H, $(C_1-C_8)$ alkyl, $(C_2-C_8)$ alkenyl, $(C_2-C_8)$ alkynyl, $(C_5-C_{20})$ aryl, $(C-C_{26})$ alkaryl, 5–20 membered heteroaryl and 6–26 membered alk-heteroaryl as defined herein.

Typical electron-withdrawing functional groups that independently selected for $Y^1$ and $Y^2$ in compounds of formula (I) include, but are not limited to —F, —NO, —$NO_2$, —CN, -trihalomethyl, and —$SO_2NHR$; where each R is independently H, $(C_1-C_8)$ alkyl, $(C_2-C_8)$ alkenyl, $(C_2-C_8)$ alkynyl, $(C_5-C_{20})$ aryl, $(C_6-C_{26})$ alkaryl, 5–20 membered heteroaryl and 6–26 membered alk-heteroaryl as defined herein. Furthermore, groups such as —$SO_2R$ and —S(O)R may be selected for $Y^2$.

Typical lipophilic functional groups that are selected for $Y^1$ and $Y^2$ include, but are not limited to n-butyl, alkoxy such as butoxy, and halogen.

One group of preferred compounds according to structure (I) are those compounds wherein $Ar^1$ is selected from the group consisting of $(C_5-C_{20})$ aryl and $(C_5-C_{20})$ aryl independently substituted with one or more $Y^1$ and $Ar^2$ is selected from the group consisting of $(C_5-C_{20})$ aryl and $(C_5-C_{20})$ aryl independently substituted with one or more $Y^2$. Particularly preferred compounds according this aspect of the invention are those compounds having the structural formula (Ia):

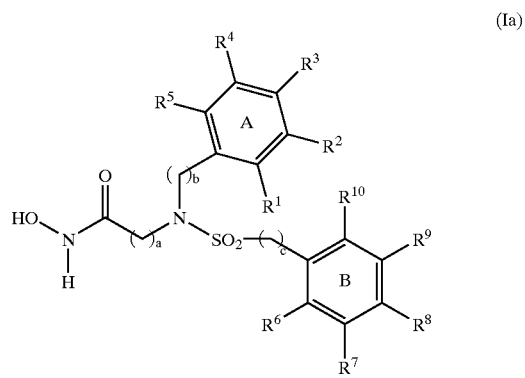

(Ia)

or pharmaceutically acceptable salts thereof, wherein:

a is an integer from 1 to 4;

b is an integer from 0 to 4;

c is an integer from 0 to 4;

$R^1$, $R^2$, $R^3$, $R^4$ and $R^5$ are each independently selected from the group consisting of —H, an electron-donating functional group, an electron-withdrawing functional group, and a lipophilic functional group;

$R^6$, $R^7$, $R^8$, $R^9$ and $R^{10}$ are each independently selected from the group consisting of —H, a functional group having an acidic hydrogen, a functional group capable of participating in a hydrogen bond (e.g., a hydrogen-donating or a hydrogen-accepting functional group), a polar functional group, an electron-withdrawing functional group, an electron-donating functional group, and a lipophilic functional group;

with the provisos that
  (i) when a and b are each one, c is other than zero; and
  (ii) when a is two, b and c are each zero and $R^1$, $R^2$, $R^4$, $R^5$, $R^6$, $R^7$, $R^9$ and $R^{10}$ are each —H, then $R^8$ is other than —F or —Cl.

Electron-donating functional groups useful for substituting the A-phenyl ring of compounds according to structure (Ia) include —R, —Cl, —OR, —SR, and —NRR, where each R is independently —H, $(C_1-C_8)$ alkyl, $(C_2-C_8)$ alkenyl or $(C_2-C_8)$ alkynyl. Particularly preferred electron-donating groups are —Cl and —$OCH_3$.

Functional groups having an acidic hydrogen useful for substituting the B-phenyl ring of compounds according to structure (Ia) include —COOH, —$SO_3H$, —P(O) $(OH)_2$, —C(O)—NH—OH,

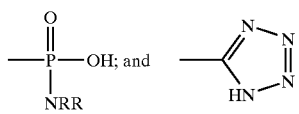

where each R is independently —H, $(C_1-C_8)$ alkyl, $(C_2-C_8)$ alkenyl, $(C_2-C_8)$ alkynyl, $(C_5-C_{20})$ aryl, $(C_6-C_{20})$ alkaryl, 5–20 membered heteroaryl and 6–26 membered alkheteroaryl as defined herein; and COOH is particularly preferred. Hydrogen-donating/accepting functional groups useful for substituting the B-phenyl ring of compounds according to structure (Ia) include —C(NHR)=N—OH, —NH—C(O)R, —NH—C(O)—NRR, —C(S)NHR, —C(O)NHR, —CO$_2$H, —NH$_2$, —C(NHR)=NR, —NH—(CO)—OR and —NH—SO$_2$—R, with —NH—C(O)—NRR being particularly preferred. Polar functional groups useful for substituting the B-phenyl ring of compounds according to structure (Ia) include —C≡N, —OR, and, —SR, with —OR being particularly preferred. Electron-withdrawing functional groups useful for substituting the B-phenyl ring of compounds according to structure (Ia) include —SO$_2$R, —S(O)R, —NO$_2$, and —CF$_3$, with —SO$_2$R being particularly preferred.

One group of preferred compounds according to structure (Ia) are those compounds wherein the A- and/or B-phenyl rings are either unsubstituted or mono-substituted. When mono-substituted, the A-phenyl ring may be substituted at either the ortho, meta or para position; however, para-substitution is preferred. When mono-substituted, the B-phenyl ring may also be substituted at the ortho, meta or para position, with para-substitution being preferred.

Another group of preferred compounds according to structure (Ia) are those compounds wherein the A-phenyl ring is di-substituted (preferably at the meta- and para-positions) and/or the B-phenyl ring is either unsubstituted or mono-substituted (preferably at the para-position).

Another group of preferred compounds according to structure (Ia) are those compounds having the structural formula (Ia')

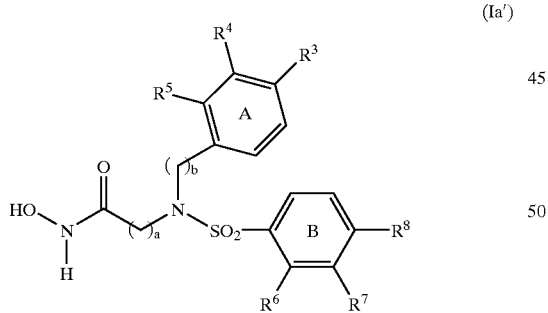

(Ia')

or pharmaceutically acceptable salts thereof, wherein:

a is an integer from 1 to 4;

b is an integer from 0 to 4;

$R^3$, $R^4$ and $R^5$ are each independently selected from the group consisting of —H, an electron-donating functional group, an electron-withdrawing functional group and a lipophilic functional group; and $R^6$, $R^7$ and $R^8$ are each independently selected from the group consisting of —H, a functional group having an acidic hydrogen, a functional group capable of participating in a hydrogen bond (e.g., a hydrogen-donating or a hydrogen-accepting functional group), a polar functional group, an electron-withdrawing functional group, an electron-donating functional group, and a lipophilic functional group; with the provisos that (i) when a is 1, b is other than 1; and (ii) when a is two and b is zero and $R^3$, $R^4$, $R^5$, $R^6$, $R^7$ are each —H, then $R^8$ is other than —F or —Cl.

One group of preferred compounds according to structure (Ia') are those compounds wherein:

a is an integer from 1 to 3;

b is an integer from 0 to 2;

$R^3$ and $R^4$ are each independently selected from the group consisting of —H, halogen (preferably —F or —Cl), —OR and trihalomethyl (preferably —CF$_3$);

$R^5$ is selected from the group consisting of —H and —OR (preferably —H);

$R^6$ is selected from the group consisting of —H, —C(O)OR, —C(NH$_2$)=NOH and —SO$_2$R;

$R^7$ is selected from the group consisting of —H and —C(NH$_2$)=NOH; and/or $R^8$ is selected from the group consisting of —H, —OR, —NO$_2$, —C(O)OR, —SO$_2$R and —C(NH$_2$)=NOH; and each R is independently selected from the group consisting of —H and $(C_1-C_3)$ alkyl (preferably methyl), $(C_2-C_3)$ alkenyl and $(C_1-C_3)$ alkynyl;

with the provisos that (i) when a is 1, b is other than 1; and (ii) when a is two and b is zero and $R^3$, $R^4$, $R^5$, $R^6$, $R^7$ are each —H, then Re is other than —F or —Cl.

Particularly preferred compounds according to structure (Ia') are as follows:

| Compound (FG) | a | b | $R^3$ | $R^4$ | $R^5$ | $R^6$ | $R^7$ | $R^8$ |
|---|---|---|---|---|---|---|---|---|
| 121 | 2 | 1 | —H | —H | —H | —H | —H | —OMe |
| 122 | 3 | 1 | —H | —H | —H | —H | —H | —OMe |
| 123 | 1 | 0 | —H | —H | —H | —H | —H | —OMe |
| 124 | 2 | 0 | —H | —H | —H | —H | —H | —OMe |
| 125 | 3 | 0 | —H | —H | —H | —H | —H | —OMe |
| 126 | 2 | 2 | —H | —H | —H | —H | —H | —OMe |

-continued

| Compound (FG) | a | b | R³ | R⁴ | R⁵ | R⁶ | R⁷ | R⁸ |
|---|---|---|---|---|---|---|---|---|
| 128 | 1 | 2 | —H | —H | —H | —H | —H | —OMe |
| 134 | 3 | 2 | —H | —H | —H | —H | —H | —OMe |
| 202 | 1 | 0 | —OMe | —H | —H | —H | —H | —OMe |
| 204 | 1 | 2 | —OMe | —H | —H | —H | —H | —OMe |
| 206 | 2 | 2 | —OMe | —H | —H | —H | —H | —OMe |
| 208 | 2 | 0 | —OMe | —H | —H | —H | —H | —OMe |
| 1268 | 2 | 2 | —H | —H | —H | —H | —H | —NO₂ |
| 1300 | 2 | 2 | —Cl | —H | —H | —H | H | —OMe |
| 1301 | 2 | 2 | —OMe | —OMe | —H | —H | —H | —OMe |
| 1405 | 2 | 2 | —H | —H | —OMe | —H | —H | —C(O)OH |
| 1455 | 2 | 2 | —OMe | —H | —H | —H | —H | —C(NH₂)=NOH |
| 1456 | 2 | 2 | —OMe | —H | —H | —H | —C(NH₂)=NOH | —H |
| 1459 | 2 | 2 | —OMe | —H | —H | —C(NH₂)=NOH | —H | —H |
| 1460 | 2 | 2 | —OMe | —H | —H | —H | —H | —SO₂Me |
| 1465 | 2 | 2 | —OMe | —H | —H | —SO₂Me | —H | —H |
| 1468 | 2 | 2 | —OMe | —H | —H | —C(O)OMe | —H | —H |
| 1474 | 2 | 1 | —C₅H₁₁ | —H | —H | —H | —H | —C(NH₂)=NOH |

In another preferred embodiment of the compounds of structure (I), $Ar^1$ is $(C_1-C_6)$ alkoxyphenyl (particularly 4'-$(C_1-C_6)$ alkoxyphenyl). Particularly preferred compounds according to this aspect of the invention are those compounds having the structural formula (Ib):

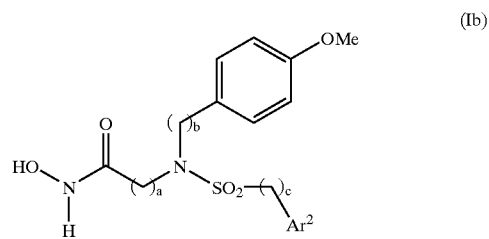

(Ib)

or pharmaceutically acceptable salts thereof, wherein:

a, b, c and $Ar^2$ are as previously defined for structure (I).

One group of preferred compounds according to structure (Ib) are those compounds wherein:

a, b and c are as previously defined for structure (I);

$Ar^2$ is selected from the group consisting of $(C_5-C_{10})$ aryl, $(C_5-C_{10})$ aryl mono-substituted with $Y^2$, 5–10 membered heteroaryl and 5–10 membered heteroaryl mono-substituted with $Y^2$;

each $Y^2$ is independently selected from the group consisting of —R, —OR, —SR, —NRR, —NO₂, —CN, halogen, —NR—C(O)—NRR, tetrazole, trihalomethyl, —C(O)R, —C(O)OR, —C(O)NRR, —C(NRR)=NOR, —C(O)NROR and —SO₂R; and each R is independently selected from the group consisting of —H, $(C_1-C_8)$ alkyl, $(C_2-C_8)$ alkenyl or $(C_2-C_8)$ alkynyl, with the provisos that when a and b is 1 then c is other than 0;

Another preferred group of compounds according to structure (Ib) are those compounds wherein:

a, b and c are as previously defined for structure (I);

$Ar^2$ is selected from the group consisting of phenyl, phenyl momo-substituted with $Y^2$, thienyl and thienyl mono-substituted with $Y^2$;

each $Y^2$ is independently selected from the group consisting of —OR, —NRR, —NO₂, —NR—C(O)—NRR, tetrazole, —CN, halogen, thrihalomethyl, —C(O)R, —C(O)OR, —C(O)NRR, —C(NH₂)=NOH, —C(O)NHOR and —SO₂R; and each R is independently selected from the group consisting of $(C_1-C_8)$ alkyl, $(C_2-C_8)$ alkenyl and $(C_2-C_8)$ alkynyl.

Particularly preferred compounds according to structure (Ib) are as follows:

| Compound (FG) | a | b | c | Ar² |
|---|---|---|---|---|
| 202 | 1 | 0 | 0 | phenyl-OMe (para) |
| 204 | 1 | 2 | 0 | phenyl-OMe (para) |
| 206 | 2 | 2 | 0 | phenyl-OMe (para) |
| 208 | 2 | 0 | 0 | phenyl-OMe (para) |
| 1455 | 2 | 2 | 0 | phenyl-C(=NOH)NH₂ (para) |
| 1456 | 2 | 2 | 0 | phenyl-C(=NOH)NH₂ (meta) |

-continued

| Compound (FG) | a | b | c | Ar² |
|---|---|---|---|---|
| 1459 | 2 | 2 | 0 | (2-methylphenyl with HON=C(NH)- group) |
| 1460 | 2 | 2 | 0 | (4-SO₂Me phenyl) |
| 1465 | 2 | 2 | 0 | (2-(MeO₂S)phenyl) |
| 1468 | 2 | 2 | 0 | (2-methylphenyl with C(O)OMe) |
| 1471 | 2 | 2 | 0 | (5-substituted thiophene-2-C(O)NHOH) |
| 1489 | 2 | 2 | 0 | (2-methylphenyl with C(O)OH) |

In still another preferred embodiment of the compounds of structure (I), Ar² is mono- or di-substituted phenyl. Particularly preferred compounds according to this aspect of the invention are those compounds having the structural formula (Ic):

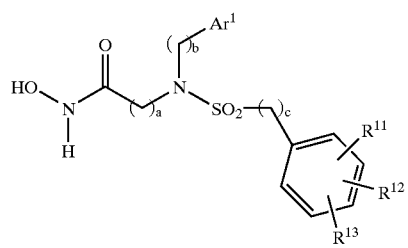

(Ic)

or pharmaceutically acceptable salts thereof, wherein:
Ar¹, a, b and c are as previously defined for structure (I);
$R^{11}$, $R^{12}$ and $R^{13}$ are each independently selected from the group consisting of —R, —OR, —SR, —NRR, —NO₂, —CN, halogen, trihalomethyl, —C(O)R, —C(O)OR, —C(O)NRR, —C(NRR)=NOR, —NR—C(O)R, —NR—C(O)—NRR, —NR—C(O)—OR, tetrazol-5-yl, —NR—SO₂—R, and —SO₂R; and
each R is independently selected from the group consisting of —H, ($C_1$-$C_8$) alkyl, ($C_2$-$C_8$) alkenyl and ($C_2$-$C_8$) alkynyl.

One preferred embodiment of the compounds of structure (Ic) are those compounds wherein at least two of $R^{11}$, $R^{12}$ and $R^{13}$ are —H:

Another preferred embodiment of the compounds of structure (Ic) are those compounds according to structure (Ic'):

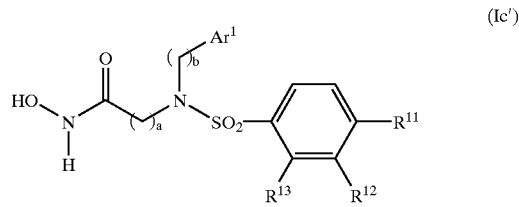

(Ic')

and pharmaceutically acceptable salts thereof, wherein:
a, b, Ar¹, $R^{11}$, $R^{12}$ and $R^{13}$ are as previously defined for structure (Ic).

One particularly preferred group of compounds according to structure (Ic') are those compounds wherein:
a, b and c are as previously defined for structure (I);
Ar¹ is selected from the group consisting of phenyl, pyridinyl, 1,3-benzodioxolyl, 1,4-benzodioxanyl, thienyl and the above-described heteroaryl groups which are independently substituted (preferably mono-substituted) with one or more $Y^1$ groups;
$R^{11}$, $R^{12}$ and $R^{13}$ are each independently selected from the group consisting of —H, —OR, —C(O)R, —C(O)OR, —C(O)NRR, —C(NH₂)NOH, —NH—C(O)R, —NR—C(O)—NRR, —NR—C(O)—OR, —NR—SO₂—R, tetrazol-5-yl and —SO₂R; and
each R is independently selected from the group consisting of hydrogen, ($C_1$-$C_3$) alkyl (preferably methyl), ($C_2$-$C_3$) alkenyl and ($C_2$-$C_3$) alkynyl.

Another particularly preferred group of compounds according to structure (Ic') are as follows:

| Compound (FG) | a | b | Ar¹ | $R^{11}$ | $R^{12}$ | $R^{13}$ |
|---|---|---|---|---|---|---|
| 1132 | 2 | 2 | pyrid-2-yl | —OMe | —H | —H |
| 1374 | 2 | 1 | 1,4-benzodioxan-2-yl | —OMe | —H | —H |
| 1273 | 2 | 1 | 1,3-benzodioxol-5-yl | —OMe | —H | —H |
| 1357 | 2 | 1 | 1,3-benzodioxol-5-yl | —NH—C(O)Me | —H | —H |

-continued

| Compound (FG) | a | b | Ar¹ | R¹¹ | R¹² | R¹³ |
|---|---|---|---|---|---|---|
| 1372 | 2 | 1 | 1,3-benzodioxol-5-yl | —O(nBu) | —H | —H |
| 1410 | 2 | 1 | 1,3-benzodioxol-5-yl | —OMe | —OMe | —H |
| 1464 | 2 | 1 | 1,3-benzodioxol-5-yl | —SO₂Me | —H | —H |
| 1369 | 2 | 1 | 1,3-benzodioxol-5-yl | —C(NH₂)=NOH | —H | —H |
| 1458 | 2 | 1 | 1,3-benzodioxol-5-yl | —H | —C(NH₂)=NOH | —H |
| 1414 | 2 | 2 | thien-2-yl | —H | —H | —H |
| 1416 | 2 | 2 | thien-2-yl | —O(nBu) | —H | —H |
| 1411 | 2 | 2 | thien-2-yl | —NH—C(O)Me | —H | —H |
| 1463 | 2 | 2 | thien-2-yl | —SO₂Me | —H | —H |
| 1457 | 2 | 2 | thien-2-yl | —H | —C(NH₂)=NOH | —H |
| 1409 | 2 | 2 | thien-2-yl | —C(NH₂)=NOH | —H | —H |
| 121 | 2 | 1 | phenyl | —OMe | —H | —H |
| 122 | 3 | 1 | phenyl | —OMe | —H | —H |
| 123 | 1 | 0 | phenyl | —OMe | —H | —H |
| 124 | 2 | 0 | phenyl | —OMe | —H | —H |
| 125 | 3 | 0 | phenyl | —OMe | —H | —H |
| 126 | 2 | 2 | phenyl | —OMe | —H | —H |
| 128 | 1 | 2 | phenyl | —OMe | —H | —H |
| 134 | 3 | 2 | phenyl | —OMe | —H | —H |
| 202 | 1 | 0 | 4'-methoxyphenyl | —OMe | —H | —H |
| 204 | 1 | 2 | 4'-methoxyphenyl | —OMe | —H | —H |
| 206 | 2 | 2 | 4'-methoxyphenyl | —OMe | —H | —H |
| 208 | 2 | 0 | 4'-methoxyphenyl | —OMe | —H | —H |
| 1300 | 2 | 2 | 4'-chlorophenyl | —OMe | —H | —H |
| 1405 | 2 | 2 | 2'-methoxyphenyl | —COOH | —H | —H |
| 1455 | 2 | 2 | 4'-methoxyphenyl | —C(NH₂)=NOH | —H | —H |
| 1456 | 2 | 2 | 4'-methoxyphenyl | —H | —C(NH₂)=NOH | —H |
| 1460 | 2 | 2 | 4'-methoxyphenyl | —SO₂Me | —H | —H |
| 1268 | 2 | 2 | phenyl | —NO₂ | —H | —H |
| 1459 | 2 | 2 | 4'-methoxyphenyl | —H | —H | —C(NH₂)=NOH |
| 1465 | 2 | 2 | 4'-methoxyphenyl | —H | —H | —SO₂Me |
| 1468 | 2 | 2 | 4'-methoxyphenyl | —H | —H | —C(O)Me |

In another embodiment, the compounds that are capable of inhibiting c-proteinase according to the invention, and which can therefore be used in methods to inhibit, modulate or regulate collagen production or maturation or to treat diseases related to, or associated with, unregulated collagen production or maturation are generally N-aryl substituted arylsulfonylamino hydroxamic acids having the structural formula (II):

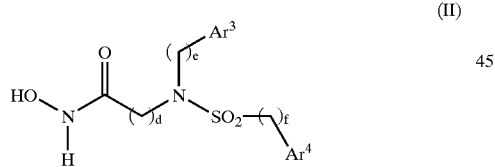

(II)

or pharmaceutically acceptable salts thereof, wherein:
  d is an integer from 1 to 4;
  e is an integer from 0 to 4;
  f is an integer from 0 to 4;
  Ar³ is selected from the group consisting of ($C_5$–$C_{20}$) aryl, ($C_5$–$C_{20}$) aryl independently substituted with one or more $Y^3$, 5–20 membered heteroaryl and 5–20 membered heteroaryl independently substituted with one or more $Y^3$;
  Ar⁴ is selected from the group consisting of ($C_5$–$C_{20}$) aryl, ($C_5$–$C_{20}$) aryl independently substituted with one or more $Y^4$, 5–20 membered heteroaryl and 5–20 membered heteroaryl independently substituted with one or more $Y^4$;
  each $Y^3$ is independently selected from the group consisting of —SO₂NH₂, —R', —OR', —SR', —NR'R', —NO₂, —CN, -halogen and trihalomethyl;
  each $Y^4$ is independently selected from the group consisting of —R', —OR', —OR", —SR', —SR", —NR'R', —NO₂, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO₂R', —SO₂R", —NR'—SO₂—R', —NR'—C(O)—NR'R', tetrazol-5-yl, —NR'—C(O)—OR', —C(NR'R')=NR', —S(O)—R', —S(O)—R", and —NR'—C(S)—NR'R';
  each R' is independently selected from the group consisting of —H, ($C_1$–$C_8$) alkyl, ($C_2$–$C_8$) alkenyl and ($C_2$–$C_8$) alkynyl; and
  each R" is independently selected from the group consisting of ($C_5$–$C_{20}$) aryl and ($C_5$–$C_{20}$) aryl independently substituted with one or more —OR', —SR', —NR'R', —NO₂, —CN, halogen or trihalomethyl groups,
  with the provisos that:
  (i) when d and e are each one, f is zero and Ar⁴ is 4'-methoxyphenyl, then Ar³ is other than phenyl, 4'-fluorophenyl, 4'-chlorophenyl, 4'-trifluoromethylphenyl or 4'-methoxyphenyl;
  (ii) when d and e are each one, f is zero and Ar⁴ is phenyl, then Ar³ is other than 4'-chlorophenyl;
  (iii) when d is two, d and e are each zero and Ar³ is phenyl, then Ar⁴ is other than 4'-chlorophenyl or 4'-bromophenyl; and
  (iv) when d and e are each one, f is zero then Ar³ is other than carbocyclic aryl-lower alkyl, carbocyclic aryl, heterocyclic aryl, biaryl, biaryl-lower alkyl, heterocyclic aryl-lower alkyl, or (N-aryl-lower alkylpiperazino)-lower alkyl
  wherein, in proviso (iv), aryl represents monocyclic or bicyclic aryl, carbocyclic aryl represents monocyclic or bicyclic carbocyclic aryl and heterocyclic aryl represents monocyclic or bicyclic heterocyclic aryl.

In one group of preferred compounds according to structure (II), Ar$^3$ is thienyl. Particularly preferred compounds according to this aspect of the invention are those compounds having the structural formula (IIa):

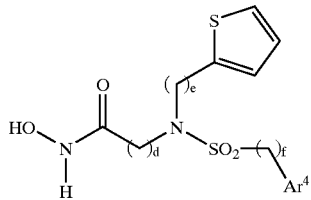

(IIa)

or pharmaceutically acceptable salts thereof, wherein d, e, f and Ar$^4$ are as previously defined for structure (II).

One group of preferred compounds according to structure (IIa) are those compounds wherein:

d, e and f are as previously defined for structure (II);
Ar$^4$ is selected from the group consisting of phenyl, phenyl independently mono- or di-substituted with Y$^4$, 5–10 membered heteroaryl and 5–10 membered heteroaryl independently mono- or di-substituted with Y$^4$;
each Y$^4$ is independently selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', tetrazol-5-yl, —NR'—C(O)—OR', —C(NR'R')=NR', —S(O)—R', —S(O)—R", —NR'—C(S)—NR'R';
each R' is independently selected from the group consisting of —H, (C$_1$-C$_8$) alkyl, (C$_2$-C$_8$) alkenyl and (C$_2$-C$_8$) alkynyl; and
each R" is independently selected from the group consisting of phenyl and phenyl independently mono- or di-substituted with halogen, —NR'R', —NO$_2$ or —CN.

Another group of preferred compounds according to structure (IIa) are those compounds wherein d is two, e is two and/or f is zero.

Another group of preferred compounds according to structure (IIa) are those compounds wherein Ar$^4$ is selected from the group consisting of thienyl (preferably thien-2-yl), 2,1,3-benzothiadiazolyl (also known as piazthiolyl) (preferably 2,1,3-benzothiadiazol-5-yl or piathiol-5-yl), imidazolyl (preferably imidazol-4-yl), 1,7-thiazopyrrolizinyl (preferably 1,7-thiazopyrrolizin-5-yl) and the above-described heteroaryl groups which are independently substituted (preferably mono-substituted) with one or more Y$^4$ groups. Particularly preferred compounds according to this aspect of the invention are as follows:

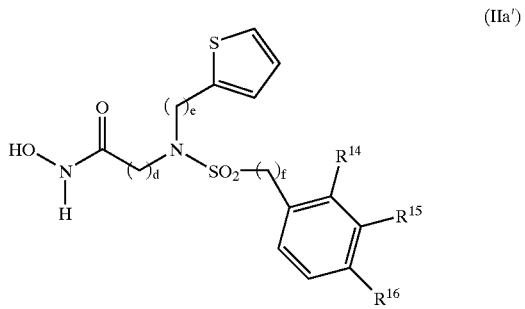

| Compound (FG) | d | e | f | Ar$^4$ |
|---|---|---|---|---|
| 1420 | 2 | 2 | 0 | |
| 1421 | 2 | 2 | 0 | |
| 1423 | 2 | 2 | 0 | |
| 1425 | 2 | 2 | 0 | |
| 1472 | 2 | 2 | 0 | |

Another group of preferred compounds according to structure (IIa) are those compounds wherein Ar$^4$ is selected from the group consisting of phenyl and phenyl independently mono-, di- or tri-substituted with Y$^4$. One group of preferred compounds according to this aspect of the invention are those compounds having the structural formula (IIa'):

(IIa')

or pharmaceutically acceptable salts thereof, wherein:
d, e, and f are as previously defined for structure (IIa);
R$^{14}$, R$^{15}$ and R$^{16}$ are each independently selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', tetrazol-5-yl, and —NR'—C(O)—OR';
each R' is independently selected from the group consisting of —H, (C$_1$-C$_8$) alkyl, (C$_2$-C$_8$) alkenyl and (C$_2$-C$_8$) alkynyl; and
R" is selected from the group consisting of phenyl and phenyl independently mono-, di-substituted or tri-substituted with halogen or —CN, with the proviso that when d and e are each one, f is other than zero.

One group of preferred compounds according to structure (IIa') are those compounds wherein d is two, e is two and/or f is zero.

Another group of preferred compounds according to structure (IIa') are those compounds wherein at least two of $R^{14}$, $R^{15}$ and $R^{16}$ are —H.

Still another group of preferred compounds according to structure (IIa') are as follows:

| Compound (FG) | d | e | f | $R^{14}$ | $R^{15}$ | $R^{16}$ |
|---|---|---|---|---|---|---|
| 1302 | 2 | 2 | 0 | —H | —H | —OMe |
| 1407 | 2 | 2 | 0 | —H | —H | —C(O)OH |
| 1408 | 2 | 2 | 0 | —H | —C(O)OH | —H |
| 1409 | 2 | 2 | 0 | —H | —H | —C(NH$_2$)=NOH |
| 1411 | 2 | 2 | 0 | —H | —H | —NH—C(O)Me |
| 1414 | 2 | 2 | 1 | —H | —H | —H |
| 1415 | 2 | 2 | 0 | —H | —OMe | —OMe |
| 1416 | 2 | 2 | 0 | —H | —H | —O(nBu) |
| 1418 | 2 | 2 | 0 | —H | —H | 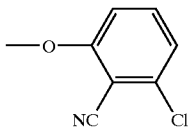 |
| 1422 | 2 | 2 | 0 | —H | —H | —CF$_3$ |
| 1424 | 2 | 2 | 0 | —H | —H | —OCF$_3$ |
| 1457 | 2 | 2 | 0 | —H | —C(NH$_2$)=NOH | —H |
| 1461 | 2 | 2 | 0 | —C(NH$_2$)=NOH | —H | —H |
| 1463 | 2 | 2 | 0 | —H | —H | —SO$_2$Me |
| 1466 | 2 | 2 | 0 | —SO$_2$Me | —H | —H |
| 1469 | 2 | 2 | 0 | —C(O)OMe | —H | —H |

Another group of preferred compounds according to structure (II) are those compounds wherein $Ar^3$ is thienyl and $Ar^4$ is thienyl or thienyl independently substituted with one or more $Y^4$. Particularly preferred compounds according to this aspect of the invention are compounds having the structural formulae (IIb) and (IIb'):

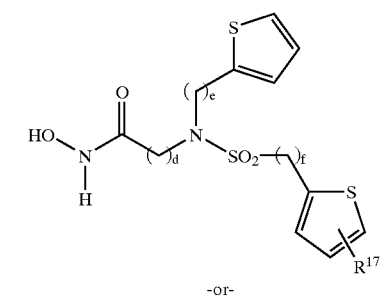

(IIb)

-or-

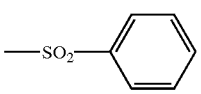

(IIb')

or pharmaceutically acceptable salts thereof, wherein:

d, e and f are as previously defined for structure (II);

$R^{17}$ is selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR° C(O)R', —SO$_2$R', —SO$_2$R", —NR'—SO$_2$—R', —NR'—C(O)—NR'R', tetrazol-5-yl, and —NR'—C(O)—OR';

R' is selected from the group consisting of —H, (C$_1$–C$_8$) alkyl, (C$_2$–C$_8$) alkenyl and (C$_2$–C$_8$) alkynyl; and R" is (C$_5$–C$_{10}$) aryl.

One group of preferred compounds according to structures (IIb) and (IIb') are those compounds wherein d is two, e two and/or f is zero.

Another group of preferred compounds according to structures (IIb) and (IIb') are as follows:

| Compound (FG) | d | e | f | $R^{17}$ |
|---|---|---|---|---|
| 1417 | 2 | 2 | 0 | —Br |
| 1419 | 2 | 2 | 0 | —SO$_2$—phenyl |
| 1425 | 2 | 2 | 0 | —H |
| 1472 | 2 | 2 | 0 | —C(O)NHOH |

Another group of preferred compounds according to structure (II) are those compounds wherein $Ar^3$ is benzodioxole. Particularly preferred compounds according to this aspect of the invention are compounds having the structural formula (IIc):

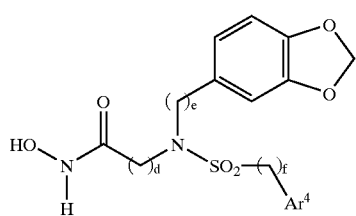
(IIc)

or pharmaceutically acceptable salts thereof, wherein d, e, f, and $Ar^4$ are as previously defined for structure (II).

One group of preferred compounds according to structure (IIc) are those compounds wherein:

d, e and f are as previously defined for structure (I);

$Ar^4$ is selected from the group consisting of phenyl, phenyl independently mono- or di-substituted with $Y^4$, 5–10 membered heteroaryl and 5–10 membered heteroaryl mono- or di-substituted with $Y^4$; and $Y^4$ is as previously defined for structure (II).

Another group of preferred compounds according to structure (IIc) are those compounds wherein d is two, e is one and/or f is zero.

Another group of preferred compounds according to structure (IIc) are those compounds wherein $Ar^4$ is selected from the group consisting of thienyl (preferably thien-2-yl), 2,1,3-benzothiadiazolyl (also known as piazthiolyl) (preferably 2,1,3-benzothiadiazol-5-yl or piathiol-5-yl), imidazolyl (preferably imidazol-4-yl), 1,7-thiazopyrrolizinyl (preferably 1,7-thiazopyrrolizin-5-yl) and the above-described heteroaryl groups which are independently mono- or di-substituted (preferably mono-substituted) with one or more $Y^4$ groups. Particularly preferred compounds of structure (IIc) according to this aspect of the invention are as follows:

| Compound (FG) | d | e | f | $Ar^4$ |
|---|---|---|---|---|
| 1367 | 2 | 1 | 0 | |
| 1361 | 2 | 1 | 0 | |
| 1362 | 2 | 1 | 0 | |
| 1363 | 2 | 1 | 0 | |

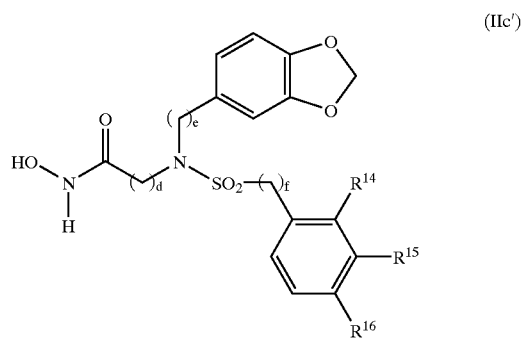

| Compound (FG) | d | e | f | $Ar^4$ |
|---|---|---|---|---|
| 1365 | 2 | 1 | 0 | |
| 1371 | 2 | 1 | 0 | |
| 1473 | 2 | 1 | 0 | |

Another group of preferred compounds according to structure (IIc) are those compounds wherein $Ar^4$ is selected from the group consisting of phenyl and phenyl independently mono-, di- or tri-substituted with $Y^4$. One group of preferred compounds according to this aspect of the invention are those compounds having the structural formula (IIc'):

(IIc')

or pharmaceutically acceptable salts thereof, wherein:

d, e, f, $R^{14}$, $R^{15}$ and $R^{16}$ are as previously defined for structure (IIa').

One group of preferred compounds according to structure (IIc') are those compounds wherein d is two, e is one and/or f is zero.

Another group of preferred compounds according to structure (IIc') are those compounds wherein at least two of $R^{14}$, $R^{15}$ and $R^{14}$ are —H.

Yet another group of preferred compounds according to structure (IIc') are as follows:

| Compound (FG) | d | e | f | R¹⁴ | R¹⁵ | R¹⁶ |
|---|---|---|---|---|---|---|
| 1273 | 2 | 1 | 0 | —H | —H | —OMe |
| 1370 | 2 | 1 | 0 | —H | —H | —C(O)OH |
| 1373 | 2 | 1 | 0 | —H | —C(O)OH | —H |
| 1369 | 2 | 1 | 0 | —H | —H | —C(NH₂)=NOH |
| 1357 | 2 | 1 | 0 | —H | —H | —NH—C(O)Me |
| 1360 | 2 | 1 | 1 | —H | —H | —H |
| 1410 | 2 | 1 | 0 | —H | —OMe | —OMe |
| 1372 | 2 | 1 | 0 | —H | —H | —O(nBu) |
| 1368 | 2 | 1 | 0 | —H | —H | 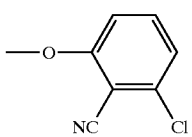 |
| 1364 | 2 | 1 | 0 | —H | —H | —CF₃ |
| 1366 | 2 | 1 | 0 | —H | —H | —OCF₃ |
| 1458 | 2 | 1 | 0 | —H | —C(NH₂)=NOH | —H |
| 1462 | 2 | 1 | 0 | —C(NH₂)=NOH | —H | —H |
| 1464 | 2 | 1 | 0 | —H | —H | —SO₂Me |
| 1467 | 2 | 1 | 0 | —SO₂Me | —H | —H |
| 1470 | 2 | 1 | 0 | —C(O)OMe | —H | —H |

Still another group of preferred compounds according to structure (II) are those compounds wherein $Ar^3$ is benzodioxole and $AR^4$ is thienyl or thienyl independently substituted with one or more $Y^4$. Particularly preferred compounds according to this aspect of the invention are compounds having the structural formulae (IId) and (IId'):

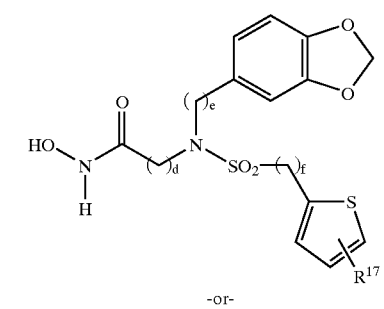

(IId)

-or-

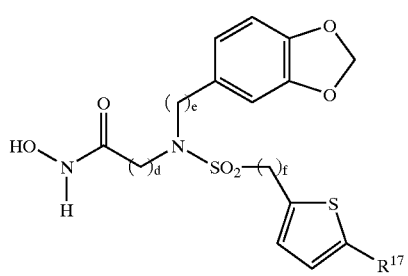

(IId')

or pharmaceutically acceptable salts thereof, wherein:
   d, e, f are as previously defined for structures (IIb) and (IIb');
   each $R^{17}$ is independently selected from the group consisting of —R', —OR', —OR", —SR', —SR", —NR'R', —NO₂, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO₂R', —SO₂R", —NR'—SO₂—R', —NR'—C(O)—NR'R', tetrazol-5-yl, and —NR'—C(O)—OR';

each R' is independently selected from the group consisting of —H, (C₁–C₈) alkyl, (C₂–C₈) alkenyl and (C₂–C₈) alkynyl; and R" is selected from the group consisting of phenyl and phenyl independently mono-, di-substituted or tri-substituted with halogen or —CN.

One preferred group of compounds according to structures (IId) and (IId') are those compounds where d is two, e is one and/or f is zero.

Another group of preferred compounds according to structures (IId) and (IId') are as follows:

| Compound (FG) | d | e | f | R¹⁷ |
|---|---|---|---|---|
| 1367 | 2 | 1 | 0 | —Br |
| 1361 | 2 | 1 | 0 | 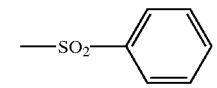 |
| 1371 | 2 | 1 | 0 | —H |
| 1473 | 2 | 1 | 0 | —C(O)NHOH |

In another embodiment, the compounds which are capable of inhibiting C-proteinase according to the invention, and which can therefore be used in methods to inhibit, modulate or regulate collagen production or maturation or to treat diseases related to, or associated with, unregulated collagen production or maturation are generally N-cycloalkyl or N-heterocycloalkyl substituted arylsulfonylamino hydroxamic acids having the structural formula (III):

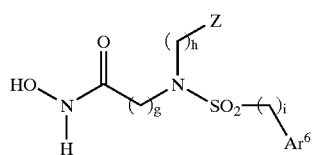

(III)

or pharmaceutically acceptable salts thereof, wherein:

g is an integer from 1 to 4;

h is an integer from 0 to 4;

i is an integer from 0 to 4;

Z is selected from the group consisting of $(C_3-C_{10})$ cycloalkyl, $(C_3-C_{10})$ cycloalkyl independently substituted with one or more $Y^5$, 3–10 membered heterocycloalkyl and 3–10 membered heterocycloalkyl independently substituted with one or more $Y^5$;

$Ar^6$ is selected from the group consisting of $(C_5-C_{20})$ aryl, $(C_5-C_{20})$ aryl independently substituted with one or more $Y^6$, 5–20 membered heteroaryl and 5–20 membered heteroaryl independently substituted with one or more $Y^6$;

each $Y^5$ is independently selected from the group consisting of a lipophilic functional group, $(C_5-C_{20})$ aryl, $(C_6-C_{26})$ alkaryl, 5–20 membered heteroaryl and 6–26 membered alk-heteroaryl;

each $Y^6$ is independently selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', tetrazol-5-yl, —NR'—C(O)—OR', —C(NR'R')=NR', —S(O)—R', —S(O)—R", and —NR'—C(S)—NR'R'; and R' and R" are as previously defined for structure (II), with the proviso that when g and h are 1, i is 0, and $Ar^6$ is phenyl, then Z is other than $C_3$–$C_7$-cycloalkyl, $C_3$–$C_7$-cycloalkyl-lower alkyl, N-lower alkyl-piperazino-lower alkyl, (morpholino, thiomorpholino, piperidino, pyrrolidino, piperidyl or N-lower alkylpiperidyl)-lower alkyl.

One group of preferred compounds according to structure (III) are those compounds wherein g is two and/or i is zero.

Another group of preferred compounds according to structure (III) are those compounds wherein:

Z is adamantyl, cyclohexyl, morpholino, tetrahydrofuranyl, piperidyl and piperidyl mono-substituted with $Y^5$;

$Ar^6$ is selected from the group consisting of phenyl and phenyl mono-substituted with $Y^6$; and $Y^5$ is —(CH$_2$)$_n$-phenyl, where n is an integer from 0 to 3.

Another group of preferred compounds according to structure (III) are those compounds wherein $Ar^6$ is $(C_1-C_6)$ alkoxyphenyl. Particularly preferred compounds according to this aspect of the invention are those compounds having the structural formula (IIIa):

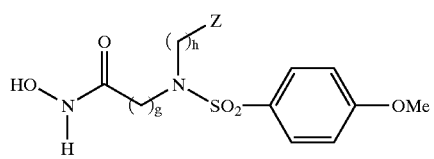

(IIIa)

or pharmaceutically acceptable salts thereof, wherein:

g, h and Z are as previously defined for structure (III).

Particularly preferred compounds according to structure (IIIa) are as follows:

| Compound (FG) | g | h | Z |
|---|---|---|---|
| 1131 | 2 | 2 | morpholino |
| 1306 | 2 | 1 | cyclohexyl |
| 1335 | 2 | 0 | adamantyl |
| 1379 | 2 | 0 | N-benzylpiperidyl |
| 1380 | 2 | 1 | tetrahydrofuranyl |

In another embodiment, the compounds that are capable of inhibiting C-proteinase according to the invention, and which can therefore be used in methods to inhibit, modulate or regulate collagen production or maturation or to treat diseases related to, or associated with, unregulated collagen production or maturation are generally N' substituted urea-arylsulfonylamino hydroxamic acids having the structural formula (IV):

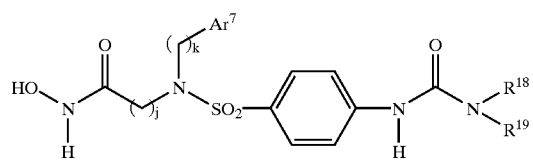

(IV)

or pharmaceutically acceptable salts thereof, wherein:

j is an integer from 1 to 4;

k is an integer from 0 to 4;

$Ar^7$ is selected from the group consisting of $(C_5-C_{20})$ aryl, $(C_5-C_{20})$ aryl independently substituted with one or more $Y^7$, 5–20 membered heteroaryl and 5–20 membered heteroaryl independently substituted with one or more $Y^7$;

$R^{18}$ and $R^{19}$ are each independently selected from the group consisting of hydrogen, ($C_1$–$C_8$) alkyl, ($C_2$–$C_8$) alkenyl, ($C_2$–$C_8$) alkynyl, ($C_3$–$C_{10}$) cycloalkyl, ($C_5$–$C_{20}$) aryl, ($C_5$–$C_{20}$) substituted aryl, ($C_6$–$C_{26}$) alkaryl, ($C_6$–$C_{26}$) substituted alkaryl, 5–20 membered heteroaryl, 5–20 membered substituted heteroaryl, 6–26 membered alk-heteroaryl, and 6–26 membered substituted alk-heteroaryl;

each $Y^7$ is independently selected from the group consisting of an electron-donating functional group, an electron-withdrawing functional group, and a lipophilic functional group.

Typical electron-donating functional groups that are independently selected for $Y^1$ in compounds of formula (IV) include, but are not limited to —Cl, —R, —OR, —SR, and —NRR; where each R is independently —H, ($C_1$–$C_8$) alkyl, ($C_2$–$C_8$) alkenyl or ($C_2$–$C_8$) alkynyl. Particularly preferred electron-donating groups are —Cl and —OCH$_3$.

Typical electron-withdrawing functional groups that are independently selected for $Y^7$ in compounds of formula (IV) include, but are not limited to —F, —NO, —NO$_2$, —CN, -trihalomethyl or —SO$_2$NHR; where R is —H, ($C_1$–$C_8$) alkyl, ($C_2$–$C_8$) alkenyl, ($C_2$–$C_8$) alkynyl, ($C_5$–$C_{20}$) aryl, ($C_6$–$C_{20}$) alkaryl, 5–20 membered heteroaryl and 6–26 membered alk-heteroaryl as defined herein.

Typical lipophilic functional groups that are selected for $Y^7$ include, but are not limited to n-butyl, alkoxy such as butoxy, and bromo.

One group of preferred compounds according to structure (IV) are those compounds wherein Ar$^7$ is ($C_5$–$C_{20}$) aryl or ($C_5$–$C_{20}$) aryl independently substituted with one or more $Y^1$ as defined in formula (IV). Particularly preferred compounds according to this aspect of the invention are those compounds having the structural formula (IVa):

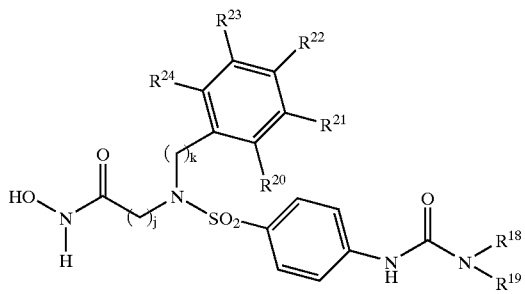

(IVa)

or pharmaceutically acceptable salts thereof, wherein:
j, k, $R^{18}$ and $R^{19}$ are as defined in formula (IV);
$R^{20}$, $R^{21}$, $R^{22}$, $R^{23}$, $R^{24}$ are independently selected from the group consisting of an electron-donating functional group, an electron-withdrawing functional group, and a lipophilic functional group.

Typical electron-donating functional groups that are independently selected for compounds of formula (IVa) include, but are not limited to —Cl, —R, —OR, —SR, —NRR, and where each R is independently —H, ($C_2$–$C_8$) alkyl, ($C_2$–$C_8$) alkenyl or ($C_2$–$C_8$) alkynyl. Particularly preferred electron-donating groups are —Cl and —OCH$_3$.

Typical electron-withdrawing functional groups that are independently selected for $Y^7$ in compounds of formula (IV) include, but are not limited to —NO, —NO$_2$, —CN, -trihalomethyl; and —SO$_2$NHR; where R is independently H, ($C_1$–$C_8$) alkyl, ($C_2$–$C_8$) alkenyl, ($C_2$–$C_8$) alkynyl, ($C_5$–$C_{20}$) aryl, ($C_6$–$C_{26}$) alkaryl, 5–20 membered heteroaryl and 6–26 membered alk-heteroaryl as defined herein.

Typical lipophilic functional groups that are selected for $Y^7$ include, but are not limited to n-butyl, alkoxy such as butoxy, and bromo.

Another group of preferred compounds according to structure (IV) are those compounds wherein Ar$^7$ is phenyl independently substituted with one or more $Y^7$ as defined in formula (IV). Particularly preferred compounds according to this aspect of the invention are those compounds having the structural formula (IVb):

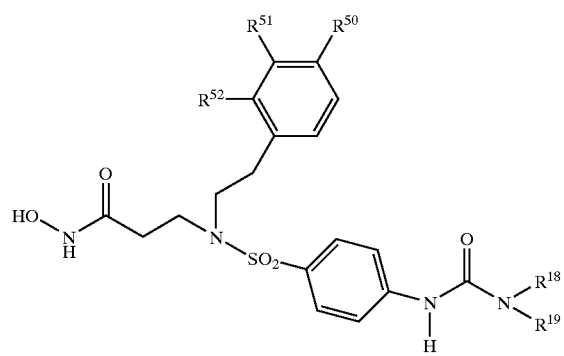

(IVb)

or pharmaceutically acceptable salts thereof, wherein:
$R^{18}$ and $R^{19}$ are as defined in formula (IV);
$R^{50}$, $R^{51}$ and $R^{52}$ are each independently selected from the group consisting of —H, —R, —OR, —SR, —NRR, —NO$_2$, —CN, halogen, trihalomethyl, —C(O)R, —C(O)OR, —C(O)NRR, —C(NRR)=NOR, —C(O)NROR, —SO$_2$NRR, and —NRSO$_2$R; and
each R is independently selected from the group consisting of ($C_1$–$C_8$) alkyl, ($C_2$–$C_8$) alkenyl and ($C_2$–$C_8$) alkynyl. Particularly preferred compounds according to structure (IVb) are as follows:

| Compound (FG) | $R^{18}$ | $R^{19}$ | $R^{50}$ | $R^{51}$ | $R^{52}$ |
|---|---|---|---|---|---|
| 1730 | 4-chlorophenyl | —H | —OMe | —H | —H |
| 1731 | —CH$_2$-phenyl | —H | —OMe | —H | —H |
| 1732 | —CH$_2$—CH$_2$-phenyl | —H | —OMe | —H | —H |
| 1733 | —Me | —H | —OMe | —H | —H |
| 1858 | (benzodioxole-CH$_2$) | —H | —OMe | —H | —H |
| 1891 | —Ph | —H | —OMe | —H | —H |
| 1894 | —CH$_2$-(4-fluorophenyl) | —H | —OMe | —H | —H |
| 1895 | -phenyl | —Ph | —OMe | —H | —H |
| 1896 | -4-biphenyl | —H | —OMe | —H | —H |
| 1943 | (benzodioxole-CH$_2$) | —H | —H | —H | —OMe |
| 1944 | (benzodioxole-CH$_2$) | —H | —H | —OMe | —H |

In another embodiment, the compounds that are capable of inhibiting C-proteinase according to the invention, and which can therefore be used in methods to inhibit, modulate or regulate collagen production or maturation or to treat diseases related to, or associated with, unregulated collagen production or maturation are urea-hydroxamic acids having the structural formula (V):

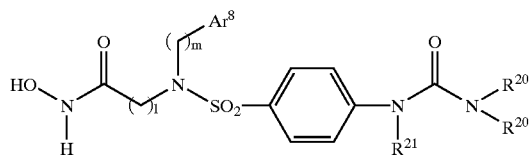

(V)

or pharmaceutically acceptable salts thereof, wherein:
l is an integer from 1 to 4;
m is an integer from 0 to 4;
$Ar^8$ is selected from the group consisting of $(C_5-C_{20})$ aryl, $(C_5-C_{20})$ aryl independently substituted with one or more $Y^8$, 5–20 membered heteroaryl and 5–20 membered heteroaryl independently substituted with one or more $Y^8$;
each $R^{20}$ is independently selected from the group consisting of hydrogen, $(C_1-C_8)$ alkyl, $(C_2-C_8)$ alkenyl, $(C_2-C_8)$ alkynyl, $(C_3-C_{10})$ cycloalkyl, $(C_5-C_{20})$ aryl, $(C_5-C_{20})$ substituted aryl, $(C_6-C_{26})$ alkaryl, $(C_6-C_{26})$ substituted alkaryl, 5–20 membered heteroaryl, 5–20 membered substituted heteroaryl, 6–26 membered alk-heteroaryl, and 6–26 membered substituted alk-heteroaryl;
$R^{21}$ is independently selected from the group consisting of hydrogen, $(C_1-C_8)$ alkyl, $(C_2-C_8)$ alkenyl, and $(C_2-C_8)$ alkynyl; and
each $Y^8$ is independently selected from the group consisting of an electron-donating functional group, an electron-withdrawing functional group, and a lipophilic functional group.

Typical electron-donating functional groups that are independently selected for $Y^7$ in compounds of formula (V) include, but are not limited to —Cl, —R, —OR, —SR, and —NRR; where each R is independently —H, $(C_1-C_8)$ alkyl, $(C_2-C_8)$ alkenyl or $(C_2-C_8)$ alkynyl. Particularly preferred electron-donating groups are —Cl and —OCH$_3$.

Typical electron-withdrawing functional groups that are independently selected for $Y^7$ in compounds of formula (V) include, but are not limited to —F, —NO, —NO$_2$, —CN, -trihalomethyl, —SO$_2$NHR; where R is independently —H, $(C_1-C_8)$ alkyl, $(C_2-C_8)$ alkenyl, $(C_2-C_8)$ alkynyl, $(C_5-C_{20})$ aryl, $(C_6-C_{26})$ alkaryl, 5–20 membered heteroaryl and 6–26 membered alk-heteroaryl as defined herein.

Typical lipophilic functional groups that are selected for $Y^7$ in compounds of formula (V) include, but are not limited to n-butyl, alkoxy such as butoxy, and bromo.

In another embodiment, the compounds that are capable of inhibiting C-proteinase according to the invention, and which can therefore be used in methods to inhibit, modulate or regulate collagen production or maturation or to treat diseases related to, or associated with, unregulated collagen production or maturation are benzoyl substituted hydroxamic acids having the structural formula (VI):

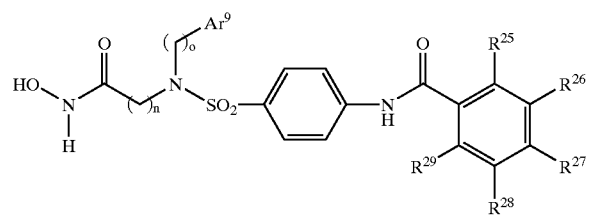

(VI)

or pharmaceutically acceptable salts thereof, wherein:
n is an integer from 1 to 4;
o is an integer from 0 to 4;
$Ar^9$ is selected from the group consisting of $(C_5-C_{20})$ aryl, $(C_5-C_{20})$ aryl independently substituted with one or more $Y^9$, 5–20 membered heteroaryl and 5–20 membered heteroaryl independently substituted with one or more $Y^9$; and
each $R^{25}$, $R^{26}$, $R^{27}$, $R^{28}$, $R^{29}$ and $Y^9$ is independently selected from the group consisting of an electron-donating functional group, an electron-withdrawing functional group, and a lipophilic functional group.

Typical electron-donating functional groups that are independently selected for $Y^9$ in compounds of formula (VI) include, but are not limited to —Cl, —R, —OR, —SR, and —NRR, where each R is independently —H, $(C_1-C_8)$ alkyl, $(C_2-C_8)$ alkenyl or $(C_2-C_8)$ alkynyl. Particularly preferred electron-donating groups are —Cl and —OCH$_3$.

Typical electron-withdrawing functional groups that are independently selected for $Y^9$ in compounds of formula (VI) include, but are not limited to —F, —NO, —NO$_2$, —CN, -trihalomethyl, and —SO$_2$NHR, where R is independently H, $(C_1-C_8)$ alkyl, $(C_2-C_8)$ alkenyl, $(C_2-C_8)$ alkynyl, $(C_5-C_{20})$ aryl, $(C_6-C_{26})$ alkaryl, 5–20 membered heteroaryl and 6–26 membered alk-heteroaryl as defined herein.

Typical lipophilic functional groups that are selected for $Y^9$ include, but are not limited to n-butyl, alkoxy such as butoxy, and bromo.

Another group of preferred compounds according to structure (VI) are those compounds wherein $Ar^9$ is phenyl independently substituted with one or more $Y^8$ as defined in formula (VI). Particularly preferred compounds according to this aspect of the invention are those compounds having the structural formula (VIa):

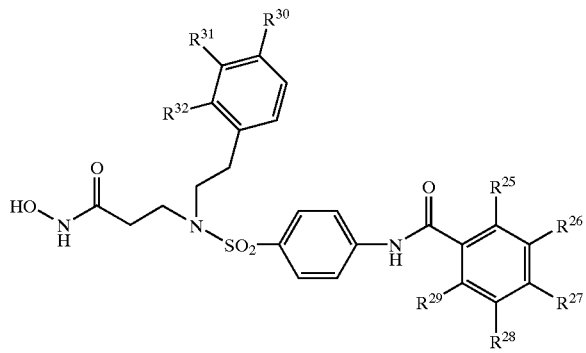

(VIa)

or pharmaceutically acceptable salts thereof, wherein:
$R^{25}$, $R^{26}$, $R^{27}$, $R^{28}$, $R^{29}$ are as defined in formula (VI);
$R^{30}$, $R^{31}$ and $R^{32}$ are each independently selected from the group consisting of —H, —R, —OR, —SR, —NRR, —$NO_2$, —CN, halogen, trihalomethyl, —C(O)R, —C(O)OR, —C(O)NRR, —C(NRR)=NOR, —C(O)NROR, —$SO_2$NRR, and —$NRSO_2R$; and each R is independently selected from the group consisting of ($C_1$–$C_8$) alkyl, ($C_2$–$C_8$) alkenyl and ($C_2$–$C_8$) alkynyl. A particularly preferred compound according to structure (VIa) is FG 2032:

(FG 2032)

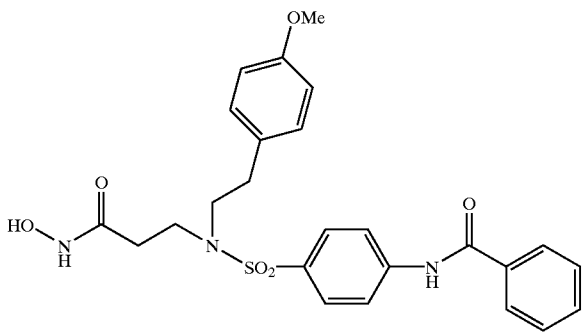

In a final embodiment, the compounds that are capable of inhibiting C-proteinase according to the invention, and which can therefore be used in methods to inhibit, modulate or regulate collagen production or maturation or to treat diseases related to, or associated with, unregulated collagen production or maturation are benzylsulfonyl substituted hydroxamic acids having the structural formula (VII):

(VII)

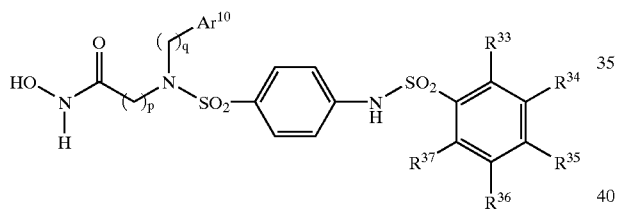

or pharmaceutically acceptable salts thereof, wherein:
p is an integer from 1 to 4;
q is an integer from 0 to 4;
$Ar^{10}$ is selected from the group consisting of ($C_5$–$C_{20}$) aryl, ($C_5$–$C_{20}$) aryl independently substituted with one or more $Y^{10}$, 5–20 membered heteroaryl and 5–20 membered heteroaryl independently substituted with one or more $Y^{10}$; and
each $R^{33}$, $R^{34}$, $R^{35}$, $R^{36}$, $R^{37}$ and $Y^{10}$ is independently selected from the group consisting of an electron-donating functional group, an electron-withdrawing functional group, and a lipophilic functional group.

Typical electron-donating functional groups that are independently selected for $Y^{10}$ in compounds of formula (VII) include, but are not limited to —Cl, —R, —OR, —SR, —NRR, and where each R is independently —H, ($C_1$–$C_8$) alkyl, ($C_2$–$C_8$) alkenyl or ($C_2$–$C_8$) alkynyl. Particularly preferred electron-donating groups are —Cl and —$OCH_3$.

Typical electron-withdrawing functional groups that are independently selected for $Y^{10}$ in compounds of formula (VII) include, but are not limited to —F, —NO, —$NO_2$, —CN, -trihalomethyl, and —$SO_2$NHR; where R is independently H, ($C_1$–$C_8$) alkyl, ($C_2$–$C_8$) alkenyl, ($C_2$–$C_8$) alkynyl, ($C_5$–$C_{20}$) aryl, ($C_6$–$C_{26}$) alkaryl, 5–20 membered heteroaryl and 6–26 membered alk-heteroaryl as defined herein.

Typical lipophilic functional groups that are selected for $Y^{10}$ include, but are not limited to n-butyl, alkoxy such as butoxy, and bromo. A group of preferred compounds according to structure (VII) are those compounds wherein $Ar^{10}$ is phenyl independently substituted with one or more $Y^{10}$ as defined in formula (VII). Particularly preferred compounds according to this aspect of the invention are those compounds having the structural formula (VIIa):

(VIIa)

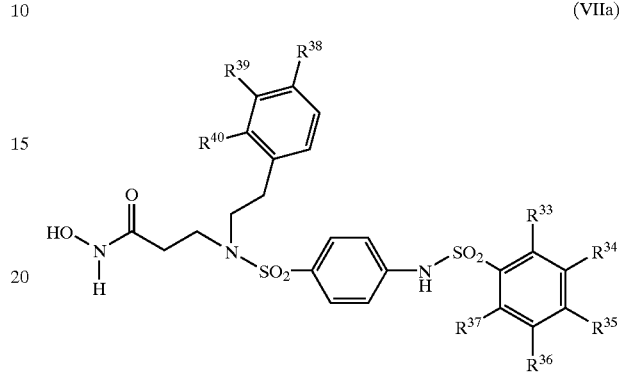

or pharmaceutically acceptable salts thereof, wherein:
$R^{33}$, $R^{34}$, $R^{35}$, $R^{36}$, $R^{37}$ are as defined in formula (VII);
$R^{38}$, $R^{39}$ and $R^{40}$ are independently selected from the group consisting of —H, —R, —OR, —SR, —NRR, —$NO_2$, —CN, halogen, trihalomethyl, —C(O)R, —C(O)OR, —C(O)NRR, —C(NRR)=NOR, —C(O)NROR, —$SO_2$NRR, and —$NRSO_2R$; and each R is independently selected from the group consisting of ($C_1$–$C_8$) alkyl, ($C_2$–$C_8$) alkenyl and ($C_2$–$C_8$) alkynyl. Particularly preferred compounds according to structure (VIIa) is FG 2033:

(FG 2033)

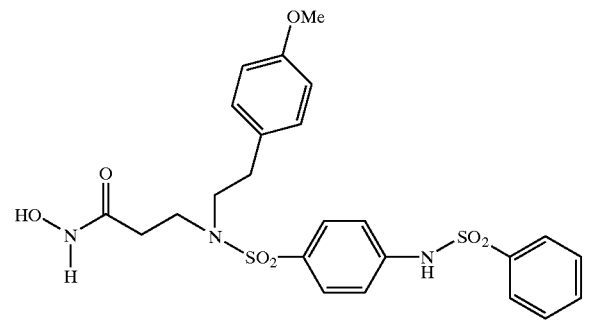

The chemical structural formulae referred to herein may exhibit the phenomena of tautomerism, conformational isomerism, geometric isomerism and/or stereo isomerism. As the formulae drawings within this specification can only represent one of the possible tautomeric, conformational isomeric, geometric isomeric or stereo isomeric forms, it should be understood that the invention encompasses any tautomeric, conformational isomeric, geometric isomeric or stereo isomeric forms which exhibit biological or pharmacological activity as defined herein.

The compounds of the invention may be in the form of free acids, free bases or pharmaceutically effective acid addition or base addition salts. Such acid addition salts can be readily prepared by treating a compound with a pharmaceutically acceptable acid. Pharmaceutically acceptable acids include, by way of example and not limitation, inorganic acids such as hydrohalic acids (hydrochloric, hydrobromic, etc.), sulfuric acid, nitric acid, phosphoric acid, etc.; and organic acids such as acetic acid, propanoic acid, 2-hydroxyacetic acid, 2-hydroxypropanoic acid, 2-oxopropanoic acid, propandioic acid, butandioic acid, etc. Conversely, the acid addition salt can be converted into the free base form by treatment with alkali. Appropriate base addition salts can be readily prepared by treating a compound with a pharmaceutically acceptable base.

In addition to the above compounds and their pharmaceutically acceptable salts, the invention is further directed, where applicable, to solvated as well as unsolvated forms of the compounds (e.g. hydrated forms) exhibiting biological or pharmacological activity as defined herein.

5.2 Methods of Making the Compounds

The compounds of the invention may be prepared by any process known to be applicable to the preparation of chemical compounds. Suitable processes are well-known in the art. See e.g., Tamura et al., 1998, *J. Med. Chem.* 41:640–649; MacPherson et al., 1997, *J. Med. Chem.* 40:2525–2532; and WO96/27583. Preferred processes are illustrated by the representative examples. Necessary starting materials may be obtained commercially or by standard procedures of organic chemistry.

By way of example, the compounds of the invention can be conveniently prepared by schemes (I) thru (XV) below:

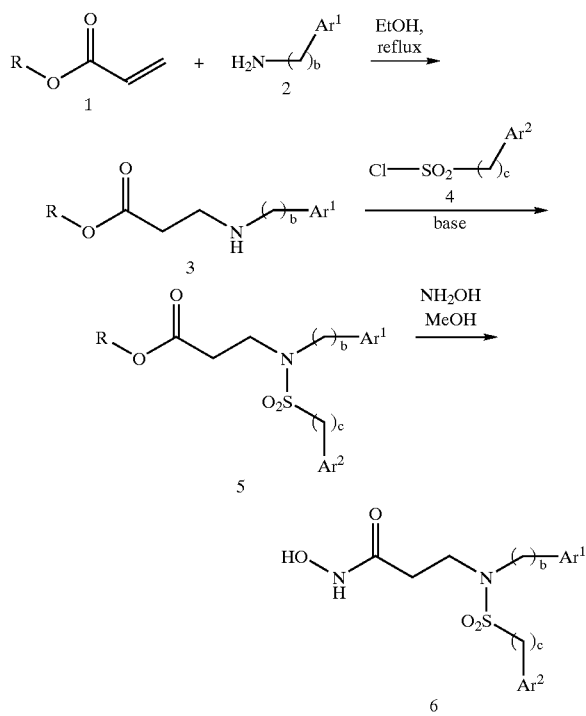

SCHEME (I)

In Scheme (I),
b is an integer from 0 to 4;
c is an integer from 0 to 4;
$Ar^1$ is selected from the group consisting of ($C_5$–$C_{20}$) aryl, ($C_5$–$C_{20}$) aryl independently substituted with one or more $Y^1$, 5–20 membered heteroaryl and 5–20 membered heteroaryl independently substituted with one or more $Y^1$;

$Ar^2$ is selected from the group consisting of ($C_5$–$C_{20}$) aryl, ($C_5$–$C_{20}$) aryl independently substituted with one or more $Y^2$, 5–20 membered heteroaryl and 5–20 membered heteroaryl independently substituted with one or more $Y^2$;

each $Y^1$ is independently selected from the group consisting of an electron-donating functional group, an electron-withdrawing functional group, and a lipophilic functional group;

each $Y^2$ is independently selected from the group consisting of a functional group having an acidic hydrogen, a functional group capable of participating in a hydrogen bond, a polar functional group, an electron-withdrawing functional group, an electron-donating functional group, and a lipophilic functional group; and R is methyl or ethyl.

According to Scheme (I), methyl acrylate or ethyl acrylate 1 is added to a solution of a primary amine 2 in ethanol. The mixture is heated to reflux (ca. 90° C.) for 20 h and then concentrated. The residue 3 is dissolved in methylene chloride (2.8 mL/mmol), followed by the addition of sulfonyl chloride 4 (1 eq.) and Amberlyst (A-21) weakly basic ion exchange resin (0.8 g/mmol). The mixture is vortexed overnight at room temperature (ca. 18 h), monitored by TLC by observing the disappearance of sulfonyl chloride. The reaction mixture is filtered and concentrated to yield residue 5. To 5 is added 2 equivalents of freshly prepared neutralized $NH_2OH$ (1 M in methanol). The mixture is vortexed overnight (monitored by TLC), concentrated, followed by work up procedure and/or chromatographic purification to afford 6. Two work up procedures are set up depending upon the feature of the product.

Hydrophobic compounds 6 are treated with 1 N HCl solution and extracted with ethyl acetate. The organic layer is dried over $MgSO_4$, filtered, and concentrated. The residue is then triturated with ether to remove undesired products which are discarded. The solid is collected and dried in vacco.

Hydrophilic compounds 6 are triturated with ethyl acetate twice. Ethyl acetate is decanted and discarded. The residue is treated with water, neutralized by 1 N HCl solution to pH=7–8, and extracted with 10/1 ethyl acetate/methanol. The combined organic layers is washed with brine, dried over magnesium sulfate, filtered, and concentrated. The residue is triturated in ether, which is discarded, and dried in vacco to furnish the product as a white solid.

In the case that a solid product formed during the work up process, the solid is collected, washed with ethyl acetate and dried in vacco. In the case that TLC indicates low purity of the desired product, purification is conducted using silica gel chromatography and/or recrystallization.

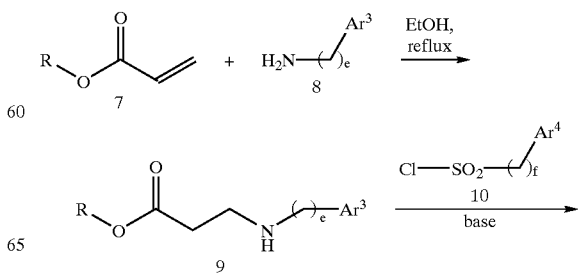

SCHEME (II)

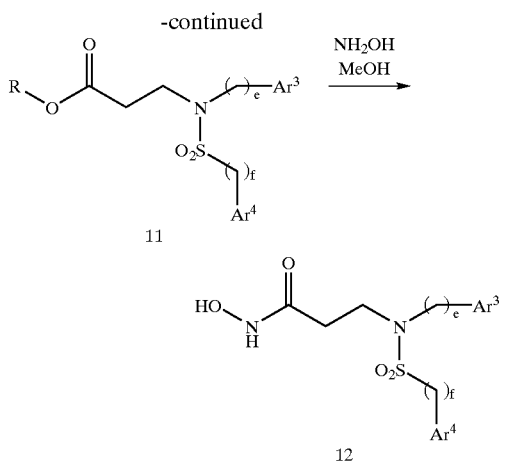

In Scheme (II), e is an integer from 0 to 4;

f is an integer from 0 to 4;

Ar$^3$ is selected from the group consisting of $(C_5-C_{20})$ aryl, $(C_5-C_{20})$ aryl independently substituted with one or more Y$^3$, 5–20 membered heteroaryl and 5–20 membered heteroaryl independently substituted with one or more Y$^3$;

Ar$^4$ is selected from the group consisting of $(C_5-C_{20})$ aryl, $(C_5-C_{20})$ aryl independently substituted with one or more Y$^4$, 5–20 membered heteroaryl and 5–20 membered heteroaryl independently substituted with one or more Y$^4$;

each Y$^3$ is independently selected from the group consisting of —R', —OR', —SR', —NR'R', —NO$_2$, —CN, -halogen and trihalomethyl;

each Y$^4$ is independently selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', tetrazol-5-yl, —NR'—C(O)—OR', —C(NR'R')=NR', —S(O)—R', —S(O)—R", —NR'—C(S)—NR'R';

each R' is independently selected from the group consisting of —H, $(C_1-C_8)$ alkyl, $(C_2-C_8)$ alkenyl and $(C_2-C_8)$ alkynyl;

each R" is independently selected from the group consisting of $(C_5-C_{20})$ aryl and $(C_5-C_{20})$ aryl independently substituted with one or more —OR', —SR', —NR'R', —NO$_2$, —CN, halogen or trihalomethyl groups; and R is methyl or ethyl.

According to Scheme (II), methyl acrylate or ethyl acrylate 7 is added to a solution of a primary amine 8 in ethanol. The mixture is heated to reflux (ca. 90° C.) for 20 h and then concentrated. The residue 9 is dissolved in methylene chloride (2.8 mL/mmol), followed by the addition of sulfonyl chloride 10 (1 eq.) and Amberlyst (A-21) weakly basic ion exchange resin (0.8 g/mmol). The mixture is vortexed overnight at room temperature (ca. 18 h), monitored by TLC by observing the disappearance of sulfonyl chloride. The reaction mixture is filtered and concentrated to yield residue 11. To 11 is added 2 equivalents of freshly prepared neutralized NH$_2$OH (1 M in methanol). The mixture is vortexed overnight (monitored by TLC), concentrated, followed by a work up procedure and/or chromatographic purification to afford 12. The work up procedure used depended upon the hydrophobicity of the product:

Hydrophobic compounds 12 are treated with 1 N HCl solution and extracted with ethyl acetate. The organic layer is dried over MgSO$_4$, filtered, and concentrated. The residue is then triturated with ether to remove undesired products which are discarded. The solid is collected and dried in vacco.

Hydrophilic compounds 12 are triturated with ethyl acetate twice. Ethyl acetate is decanted and discarded. The residue is treated with water, neutralized by 1 N HCl solution to pH=7–8, and extracted with 10/1 ethyl acetate/methanol. The combined organic layers is washed with brine, dried over magnesium sulfate, filtered, and concentrated. The residue is triturated in ether, which is discarded, and dried in vacco to furnish the product as a white solid.

In the case that solid product formed during work up process, the solid is collected, washed with ethyl acetate and dried in vacco. In the case that TLC indicates low purity of the desired product, purification is conducted using silica gel chromatography and/or recrystallization.

SCHEME (III)

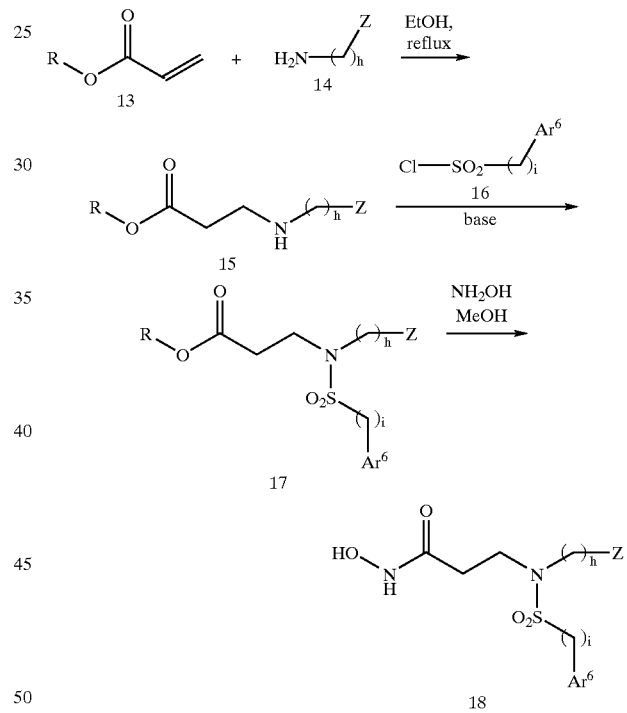

In Scheme (III)

h is an integer from 0 to 4;

i is an integer from 0 to 4;

Z is selected from the group consisting of $(C_3-C_{10})$ cycloalkyl, $(C_3-C_{10})$ cycloalkyl independently substituted with one or more Y$^5$, 3–10 membered heterocycloalkyl and 3–10 membered heterocycloalkyl independently substituted with one or more Y$^5$;

Ar$^6$ is selected from the group consisting of $(C_5-C_{20})$ aryl, $(C_5-C_{20})$ aryl independently substituted with one or more Y$^6$, 5–20 membered heteroaryl and 5–20 membered heteroaryl independently substituted with one or more Y$^6$;

each Y$^5$ is independently selected from the group consisting of a lipophilic functional group, $(C_5-C_{20})$ aryl, ($C_6$–$C_{26}$) alkaryl, 5–20 membered heteroaryl and 6–26 membered alk-heteroaryl;

each $Y^6$ is independently selected from the group consisting of —R', —OR', —OR", —SR', —SR", —NR'R', —$NO_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —$SO_2$R', —$SO_2$R", —NR'—$SO_2$—R', —NR'—C(O)—NR'R', tetrazol-5-yl, —NR'—C(O)—OR', —C(NR'R')=NR', —S(O)—R', —S(O)—R", —NR'—C(S)—NR'R';

—R' and R" are as previously defined for Scheme (II); and

R is methyl or ethyl.

According to Scheme (III), methyl acrylate or ethyl acrylate 13 is added to a solution of a primary amine 14 in ethanol. The mixture is heated to reflux (ca. 90° C.) for 20 h and then concentrated. The residue 15 is dissolved in methylene chloride (2.8 mL/mmol), followed by the addition of sulfonyl chloride 16 (1 eq.) and Amberlyst (A-21) weakly basic ion exchange resin (0.8 g/mmol). The mixture is vortexed overnight at room temperature (ca. 18 h), monitored by TLC by observing the disappearance of sulfonyl chloride. The reaction mixture is filtered and concentrated to yield residue 17. To 17 is added 2 equivalents of freshly prepared neutralized $NH_2OH$ (1 M in methanol). The mixture is vortexed overnight (monitored by TLC), concentrated, followed by work up procedure and/or chromatographic purification to afford 18. The work up procedure used depended upon the hydrophobicity of the product:

Hydrophobic compounds 18 are treated with 1 N HCl solution and extracted with ethyl acetate. The organic layer is dried over $MgSO_4$, filtered, and concentrated. The residue is then triturated with ether to remove undesired products which are discarded. The solid is collected and dried in vacco.

Hydrophilic compounds 18 are triturated with ethyl acetate twice. Ethyl acetate is decanted and discarded. The residue is treated with water, neutralized by 1 N HCl solution to pH=7–8, and extracted with 10/1 ethyl acetate/methanol. The combined organic layers is washed with brine, dried over magnesium sulfate, filtered, and concentrated. The residue is triturated in ether, which is discarded, and dried in vacco to furnish the product as a white solid.

In the case that solid product formed during work up process, the solid is collected, washed with ethyl acetate and dried in vacco. In the case that TLC indicates low purity of the desired product, purification is conducted using silica gel chromatography and/or recrystallization.

SCHEME (IV)

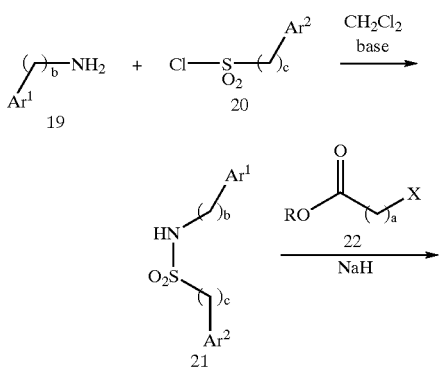

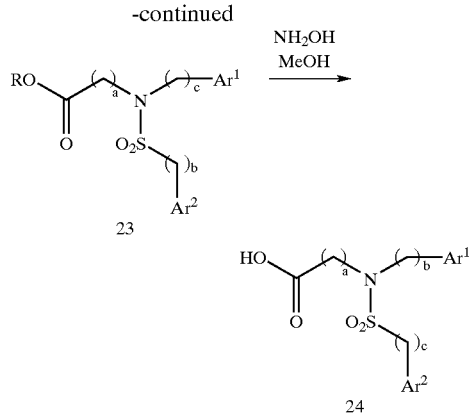

In Scheme (IV), a is an integer from 1 to 4;

b is an integer from 0 to 4;

c is an integer from 0 to 4;

$Ar^1$ is selected from the group consisting of ($C_5$–$C_{20}$) aryl, ($C_5$–$C_{20}$) aryl independently substituted with one or more $Y^1$, 5–20 membered heteroaryl and 5–20 membered heteroaryl independently substituted with one or more $Y^1$;

$Ar^2$ is selected from the group consisting of ($C_5$–$C_{20}$) aryl, ($C_5$–$C_{20}$) aryl independently substituted with one or more $Y^2$, 5–20 membered heteroaryl and 5–20 membered heteroaryl independently substituted with one or more $Y^2$;

each $Y^1$ is independently selected from the group consisting of an electron-donating functional group, an electron-accepting functional group, and a lipophilic functional group;

each $Y^2$ is independently selected from the group consisting of a functional group having an acidic hydrogen, a functional group capable of participating in a hydrogen bond, a polar functional group, an electron-withdrawing functional group, an electron-donating functional group, and a lipophilic functional group;

R is methyl or ethyl; and

X is chloro or bromo.

According to Scheme (IV), a primary amine 19 is dissolved in methylene chloride, followed by the addition of sulfonyl chloride 20 and Amberlyst weakly basic ion exchange resin to yield compound 21. Compound 21 is dissolved in dry DMF and stirred under argon. To this mixture is added sodium hydride 60% suspended in mineral oil and the resulting mixture stirred. To this mixture is added compound 22 to yield compound 23 after silica gel chromatography. To compound 23 is added freshly prepared $NH_2OH$ (1 M in methanol). The mixture is stirred to afford compound 24. Depending on the chemical properties of compound 24, it is worked up as follows.

Hydrophobic compounds 24 are treated with a HCl solution and extracted with ethyl acetate. The organic layer is dried over $MgSO_4$, filtered, and concentrated. The residue is then triturated with ether to remove undesired products which are discarded. The solid is collected and dried in vacco.

Hydrophilic compounds 24 are triturated with ethyl acetate twice. Ethyl acetate is decanted and discarded. The residue is treated with water, neutralized by 1 N HCl solution to pH=7–8, and extracted with 10/1 ethyl acetate/methanol. The combined organic layers is washed with brine, dried over magnesium sulfate, filtered, and concentrated. The residue is triturated in ether, which is discarded, and dried in vacco to furnish the product as a white solid.

SCHEME (V)

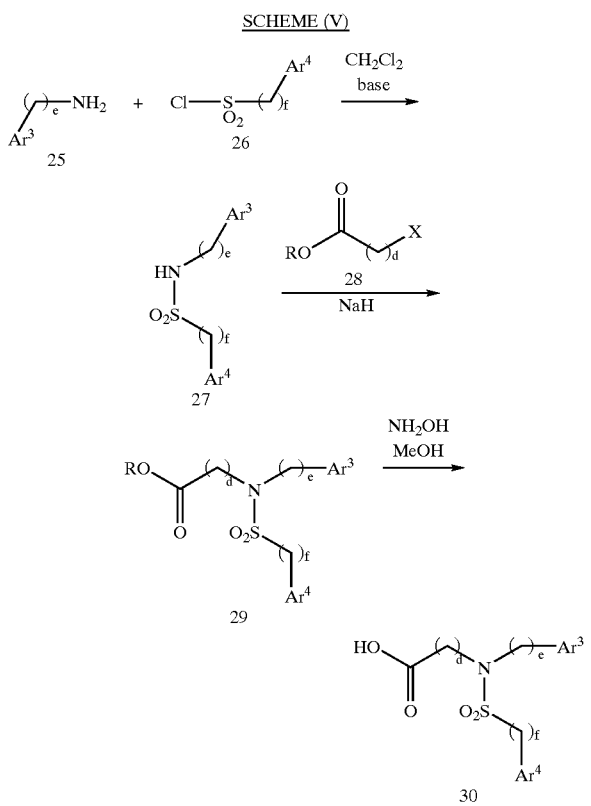

In Scheme (V), d is an integer from 1 to 4;
e is an integer from 0 to 4;
f is an integer from 0 to 4;
$Ar^3$ is selected from the group consisting of $(C_5-C_{20})$ aryl, $(C_5-C_{20})$ aryl independently substituted with one or more $Y^3$, 5–20 membered heteroaryl and 5–20 membered heteroaryl independently substituted with one or more $Y^3$;
$Ar^4$ is selected from the group consisting of $(C_1-C_{20})$ aryl, $(C_5-C_{20})$ aryl independently substituted with one or more $Y^4$, 5–20 membered heteroaryl and 5–20 membered heteroaryl independently substituted with one or more $Y^4$;
each $Y^3$ is independently selected from the group consisting of —R', —OR', —SR', —NR'R', —NO$_2$, —CN, -halogen and trihalomethyl;
each $Y^4$ is independently selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', tetrazol-5-yl, —NR'—C(O)—OR', —C(NR'R')=NR', —S(O)—R', —S(O)—R", —NR'—C(S)—NR'R';
each R' is independently selected from the group consisting of —H, $(C_1-C_8)$ alkyl, $(C_2-C_8)$ alkenyl and $(C_2-C_8)$ alkynyl;
each R" is independently selected from the group consisting of $(C_5-C_{20})$ aryl and $(C_5-C_{20})$ aryl independently substituted with one or more —OR', —SR', —NR'R', —NO$_2$, —CN, halogen or trihalomethyl groups;
R is methyl or ethyl; and
X is chloro or bromo.

According to Scheme (V), a primary amine 25 is dissolved in methylene chloride, followed by the addition of sulfonyl chloride 26 and Amberlyst weakly basic ion exchange resin to yield compound 27. Compound 27 is dissolved in dry DMF and stirred under argon. To this mixture is added sodium hydride 60% suspended in mineral oil and the resulting mixture stirred. To this mixture is added compound 28 to yield compound 29 after silica gel chromatography. To compound 29 is added freshly prepared NH$_2$OH (1 M in methanol). The mixture is stirred to afford compound 30. Depending on the chemical properties of compound 30, it is worked up as follows:

Hydrophobic compounds 30 are treated with a HCl solution and extracted with ethyl acetate. The organic layer is dried over MgSO$_4$, filtered, and concentrated. The residue is then triturated with ether to remove undesired products which are discarded. The solid is collected and dried in vacco.

Hydrophilic compounds 30 are triturated with ethyl acetate twice. Ethyl acetate is decanted and discarded. The residue is treated with water, neutralized by 1 N HCl solution to pH=7–8, and extracted with 10/1 ethyl acetate/methanol. The combined organic layers is washed with brine, dried over magnesium sulfate, filtered, and concentrated. The residue is triturated in ether, which is discarded, and dried in vacco to furnish the product as a white solid.

SCHEME (VI)

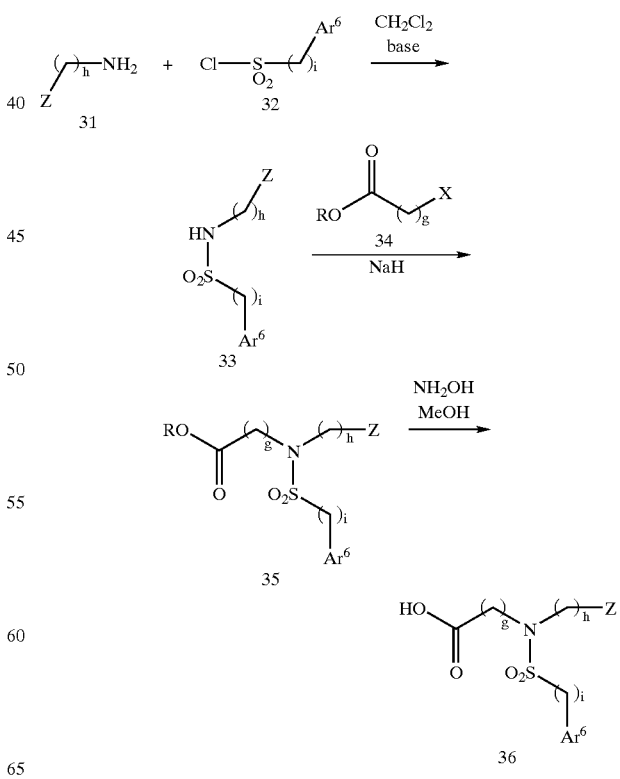

47

In Scheme (VI), g is an integer from 1 to 4;

h is an integer from 0 to 4;

i is an integer from 0 to 4;

Z is selected from the group consisting of $(C_3-C_{10})$ cycloalkyl, $(C_3-C_{10})$ cycloalkyl independently substituted with one or more $Y^5$, 3–10 membered heterocycloalkyl and 3–10 membered heterocycloalkyl independently substituted with one or more $Y^5$;

$Ar^6$ is selected from the group consisting of $(C_5-C_{20})$ aryl, $(C_5-C_{20})$ aryl independently substituted with one or more $Y^6$, 5–20 membered heteroaryl and 5–20 membered heteroaryl independently substituted with one or more $Y^6$;

each $Y^5$ is independently selected from the group consisting of a lipophilic functional group, $(C_5-C_{20})$ aryl, $C_5-C_{26}$) alkaryl, 5–20 membered heteroaryl and 6–26 membered alk-heteroaryl;

each $Y^6$ is independently selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', tetrazol-5-yl, —NR'—C(O)—OR', —C(NR'R')=NR', —S(O)—R', —S(O)—R", —NR'—C(S)—NR'R';

each R' is independently selected from the group consisting of —H, $(C_1-C_8)$ alkyl, $(C_2-C_8)$ alkenyl and $(C_2-C_8)$ alkynyl;

each R" is independently selected from the group consisting of $(C_5-C_{20})$ aryl and $(C_5-C_{20})$ aryl independently substituted with one or more —OR', —SR', —NR'R', —NO$_2$, —CN, halogen or trihalomethyl groups;

R is methyl or ethyl; and

X is chloro or bromo.

According to Scheme (VI), a primary amine 31 is dissolved in methylene chloride, followed by the addition of sulfonyl chloride 32 and Amberlyst weakly basic ion exchange resin to yield compound 33. Compound 33 is dissolved in dry DMF and stirred under argon. To this mixture is added sodium hydride 60% suspended in mineral oil and the resulting mixture stirred. To this mixture is added compound 34 to yield compound 35 after silica gel chromatography. To compound 35 is added freshly prepared NH$_2$OH (1 M in methanol). The mixture is stirred to afford compound 36. Depending on the chemical properties of compound 36, it is worked up as follows.

Hydrophobic compounds 36 are treated with a HCl solution and extracted with ethyl acetate. The organic layer is dried over MgSO$_4$, filtered, and concentrated. The residue is then triturated with ether to remove undesired products which are discarded. The solid is collected and dried in vacco.

Hydrophilic compounds 36 are triturated with ethyl acetate twice. Ethyl acetate is decanted and discarded. The residue is treated with water, neutralized by 1 N HCl solution to pH 7–8, and extracted with 10/1 ethyl acetate/methanol. The combined organic layers is washed with brine, dried over magnesium sulfate, filtered, and concentrated. The residue is triturated in ether, which is discarded, and dried in vacco to furnish the product as a white solid.

48

SCHEME (VII)

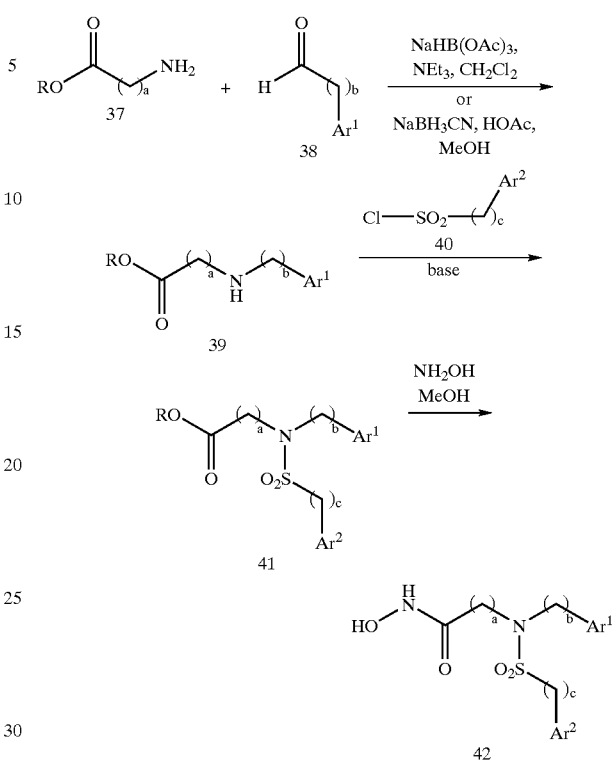

In Scheme (VII), a is an integer from 1 to 2;

b is an integer from 0 to 4;

c is an integer from 0 to 4;

$Ar^1$ is selected from the group consisting of $(C_5-C_{20})$ aryl, $(C_5-C_{20})$ aryl independently substituted with one or more $Y^1$, 5–20 membered heteroaryl and 5–20 membered heteroaryl independently substituted with one or more $Y^1$;

$Ar^2$ is selected from the group consisting of $(C_5-C_{20})$ aryl, $(C_5-C_{20})$ aryl independently substituted with one or more $Y^2$, 5–20 membered heteroaryl and 5–20 membered heteroaryl independently substituted with one or more $Y^2$;

each $Y^1$ is independently selected from the group consisting of an electron-donating functional group, an electron-withdrawing functional group, and a lipophilic functional group;

each $Y^2$ is independently selected from the group consisting of a functional group having an acidic hydrogen, a functional group capable of participating in a hydrogen bond, a polar functional group, an electron-withdrawing functional group, an electron-donating functional group, and a lipophilic functional group; and R is methyl or ethyl.

According to Scheme (VII), to a solution of compound 37 in anhydrous methylene chloride at room temperature is added triethyl amine and compound 38. After the mixture is stirred, sodium triacetoxyborohydride is added and the reaction mixture is stirred for additional period of time to yield compound 39. To compound 39 is added compound 40 and triethyl amine. The resulting mixture is stirred and then quenched with citric acid yielding compound 41. To compound 41 in methanol is added freshly prepared NH$_2$OH solution. The mixture is stirred and concentrated to yield compound 42.

SCHEME (VIII)

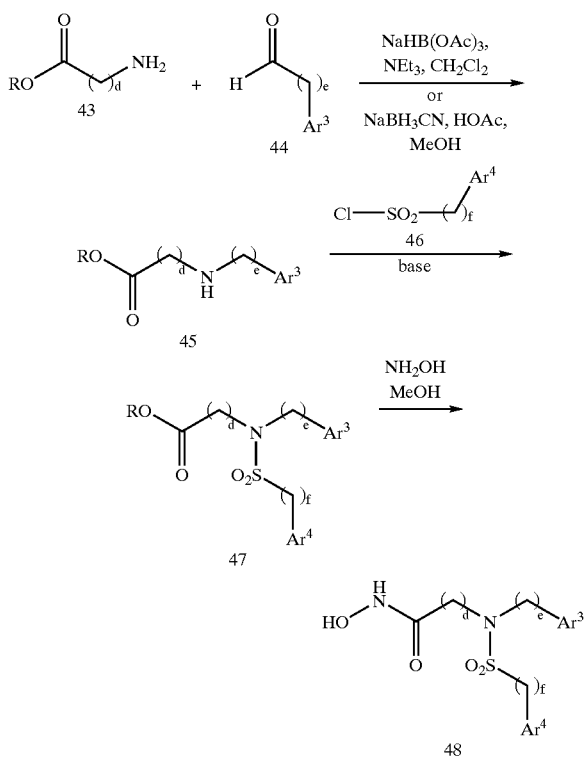

In Scheme (VIII), d is an integer from 1 to 4;

e is an integer from 0 to 4;

f is an integer from 0 to 4;

$Ar^3$ is selected from the group consisting of ($C_5$–$C_{20}$) aryl, ($C_5$–$C_{20}$) aryl independently substituted with one or more $Y^3$, 5–20 membered heteroaryl and 5–20 membered heteroaryl independently substituted with one or more $Y^3$;

$Ar^4$ is selected from the group consisting of ($C_5$–$C_{20}$) aryl, ($C_5$–$C_{20}$) aryl independently substituted with one or more $Y^4$, 5–20 membered heteroaryl and 5–20 membered heteroaryl independently substituted with one or more $Y^4$;

each $Y^3$ is independently selected from the group consisting of —R', —OR', —SR', —NR'R', —NO$_2$, —CN, -halogen and trihalomethyl;

each $Y^4$ is independently selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', tetrazol-5-yl, —NR'—C(O)—OR', —C(NR'R')=NR', —S(O)—R', —S(O)—R", —NR'—C(S)—NR'R';

each R' is independently selected from the group consisting of —H, ($C_1$–$C_8$) alkyl, ($C_2$–$C_8$) alkenyl and ($C_2$–$C_8$) alkynyl;

each R" is independently selected from the group consisting of ($C_5$–$C_{20}$) aryl and ($C_5$–$C_{20}$) aryl independently substituted with one or more —OR', —SR', —NR'R', —NO$_2$, —CN, halogen or trihalomethyl groups; and R is methyl or ethyl.

According to Scheme (VIII), to a solution of compound 43 in anhydrous methylene chloride at room temperature is added triethyl amine and compound 44. After the mixture is stirred, sodium triacetoxyborohydride is added and the reaction mixture is stirred for additional period of time to yield compound 45. To compound 45 is added compound 46 and triethyl amine. The resulting mixture is stirred and then quenched with citric acid yielding compound 47. To compound 47 in methanol is added freshly prepared NH$_2$OH solution. The mixture is stirred and concentrated to yield compound 48.

SCHEME (IX)

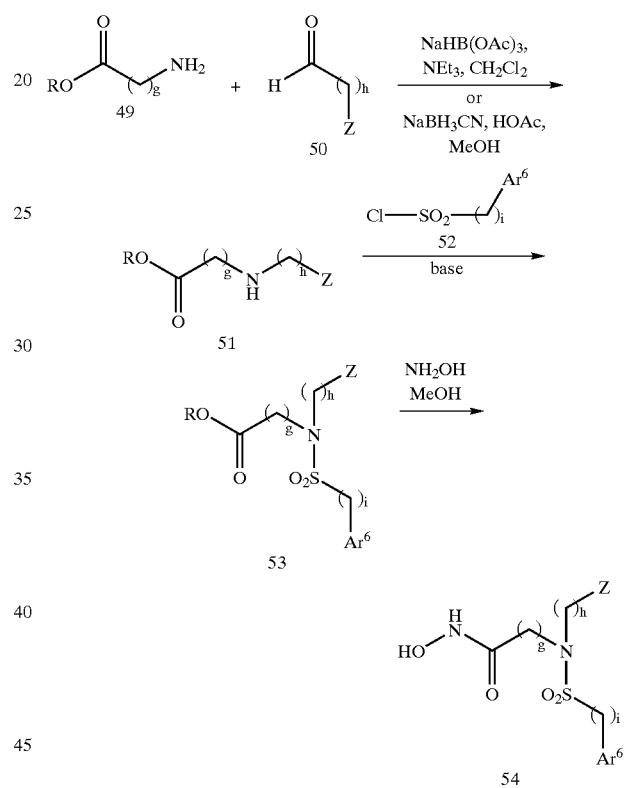

In scheme (IX), g is an integer from 1 to 4;

h is an integer from 0 to 4;

i is an integer from 0 to 4;

Z is selected from the group consisting of ($C_3$–$C_{10}$) cycloalkyl, ($C_3$–$C_{10}$) cycloalkyl independently substituted with one or more $Y^5$, 3–10 membered heterocycloalkyl and 3–10 membered heterocycloalkyl independently substituted with one or more $Y^5$;

$Ar^6$ is selected from the group consisting of ($C_5$–$C_{20}$) aryl, ($C_5$–$C_{20}$) aryl independently substituted with one or more $Y^6$, 5–20 membered heteroaryl and 5–20 membered heteroaryl independently substituted with one or more $Y^6$;

each $Y^5$ is independently selected from the group consisting of a lipophilic functional group, ($C_5$–$C_{20}$) aryl, ($C_6$–$C_{26}$) alkaryl, 5–20 membered heteroaryl and 6–26 membered alk-heteroaryl;

each $Y^6$ is independently selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')═NOR', —NR'—C(O)R', —SO$_2$R', —SO$_2$R", —NR'—SO$_2$—R', —NR'—C(O)—NR'R', tetrazol-5-yl, —NR'—C(O)—OR', —C(NR'R')═NR', —S(O)—R', —S(O)—R", and —NR'—C(S)—NR'R';

- each R' is independently selected from the group consisting of —H, (C$_1$–C$_8$) alkyl, (C$_2$–C$_8$) alkenyl and (C$_2$–C$_8$) alkynyl;
- each R" is independently selected from the group consisting of (C$_5$–C$_{20}$) aryl and (C$_5$–C$_{20}$) aryl independently substituted with one or more —OR', —SR', —NR'R', —NO$_2$, —CN, halogen or trihalomethyl groups; and
- R is methyl or ethyl.

According to scheme (IX), to a solution of compound 49 in anhydrous methylene chloride at room temperature is added triethyl amine and compound 50. After the mixture is stirred, sodium triacetoxyborohydride is added and the reaction mixture is stirred for additional period of time to yield compound 51. To compound 51 is added compound 52 and triethyl amine. The resulting mixture is stirred and then quenched with citric acid yielding compound 53. To compound 53 in methanol is added freshly prepared NH$_2$OH solution. The mixture is stirred and concentrated to yield compound 54.

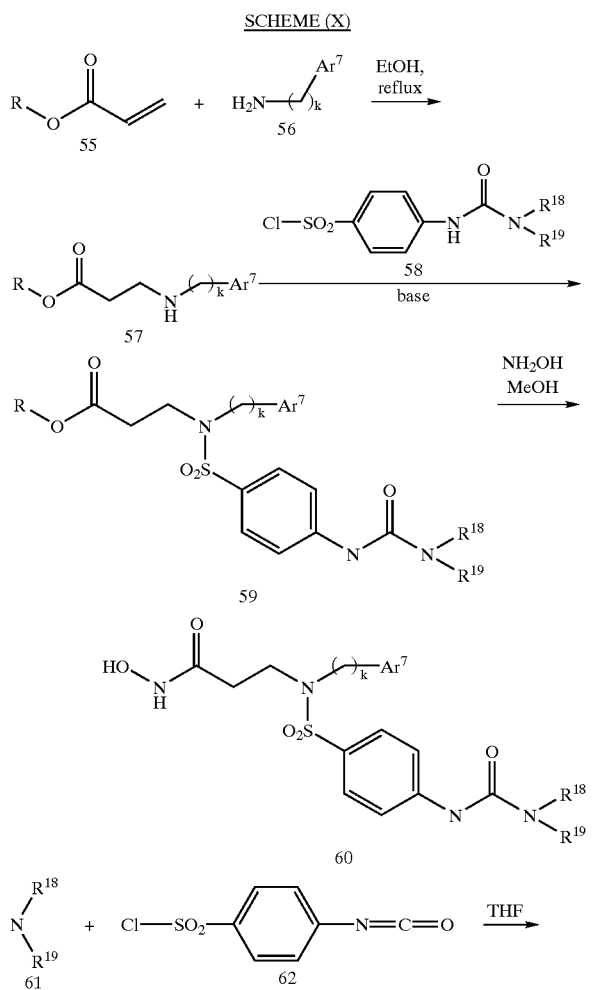

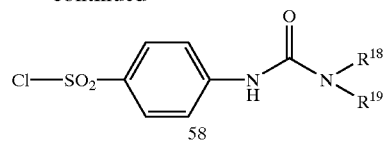

In Scheme (X), k is an integer from 0 to 4;

Ar$^7$ is selected from the group consisting of (C$_5$–C$_{20}$) aryl, (C$_5$–C$_{20}$) aryl independently substituted with one or more Y$^7$, 5–20 membered heteroaryl and 5–20 membered heteroaryl independently substituted with one or more Y$^7$ R$^{18}$ and R$^{19}$ are independently selected from the group consisting of hydrogen, (C$_1$–C$_8$) alkyl, (C$_2$–C$_8$) alkenyl, (C$_2$–C$_8$) alkynyl, (C$_3$–C$_{10}$) cycloalkyl, (C$_5$–C$_{20}$) aryl, (C$_5$–C$_{20}$) substituted aryl, (C$_1$–C$_{26}$) alkaryl, (C$_6$–C$_{26}$) substituted alkaryl, 6–20 membered heteroaryl, 5–20 membered substituted heteroaryl, 6–26 membered alk-heteroaryl, and 6–26 membered substituted alk-heteroaryl; and each Y$^7$ is independently selected from the group consisting of an electron-donating functional group, an electron-withdrawing functional group, and a lipophilic functional group.

Typical electron-donating functional groups that are independently selected for Y$^7$ in compounds of formula (IV) include, but are not limited to —Cl, —R, —OR, —SR, —NRR, and where each R is independently —H, (C$_1$–C$_8$) alkyl, (C$_2$–C$_8$) alkenyl or (C$_2$–C$_8$) alkynyl. Particularly preferred electron-donating groups are —Cl and —OCH$_3$.

Typical electron-withdrawing functional groups that are independently selected for Y$^7$ in compounds of formula (IV) include, but are not limited to —F, —NO, —NO$_2$, —CN, -trihalomethyl, —SO$_2$NHR; where R is independently H, (C$_1$–C$_8$) alkyl, (C$_2$–C$_8$) alkenyl, (C$_2$–C$_8$) alkynyl, (C$_5$–C$_{20}$) aryl, (C$_6$–C$_{26}$) alkaryl, 5–20 membered heteroaryl and 6–26 membered alk-heteroaryl as defined herein.

Typical lipophilic functional groups that are selected for Y$^7$ include, but are not limited to n-butyl, alkoxy such as butoxy, and bromo; and R is methyl or ethyl.

According to Scheme (X), methyl acrylate or ethyl acrylate 55 is added to a solution of a primary amine 56 in ethanol. The mixture is heated to reflux (ca. 90° C.) for 20 h and then concentrated. The residue 57 is dissolved in methylene chloride, followed by the addition of 4-(3-substituted-ureido)benzenesulfonyl chloride 58 (1 eq.) and Amberlyst (A-21) weakly basic ion exchange resin (0.8 g/mmol). The mixture is vortexed overnight at room temperature (ca. 18 h), monitored by TLC by observing the disappearance of sulfonyl chloride. The reaction mixture is filtered and concentrated to yield residue 59. To 59 is added 2 equivalents of freshly prepared neutralized NH$_2$OH (1 M in methanol). The mixture is vortexed overnight (monitored by TLC), concentrated, followed by work up procedure and/or chromatographic purification to afford 60. Two work up procedures are set up depending upon the feature of the product.

Hydrophobic compounds 60 are treated with 1 N HCl solution and extracted with ethyl acetate. The organic layer is dried over MgSO$_4$, filtered, and concentrated. The residue is then triturated with ether to remove undesired products which are discarded. The solid is collected and dried in vacco.

Hydrophilic compounds 60 are triturated with ethyl acetate twice. Ethyl acetate is decanted and discarded. The residue is treated with water, neutralized by 1 N HCl solution to pH=7–8, and extracted with 10/1 ethyl acetate/methanol. The combined organic layers is washed with brine, dried over magnesium sulfate, filtered, and concentrated. The residue is triturated in ether, which is discarded, and dried in vacco to furnish the product as a white solid.

In the case that solid product formed during work up process, the solid is collected, washed with ethyl acetate and dried in vacco. In the case that TLC indicates low purity of the desired product, purification is conducted using silica gel chromatography and/or recrystallization.

Compound 58 is prepared by the following method: To a solution of primary or secondary amine 61 (0.5 mmol) in THF (1 mL) at 0° C. was added 4-(chlorosulfonyl)phenyl isocyanate 62 (0.5 mmol). After stirring at 0° C. for 2 h, the mixture was concentrated to afford 4-(3-substituted-ureido) benzenesulfonyl chloride 58.

SCHEME (XI)

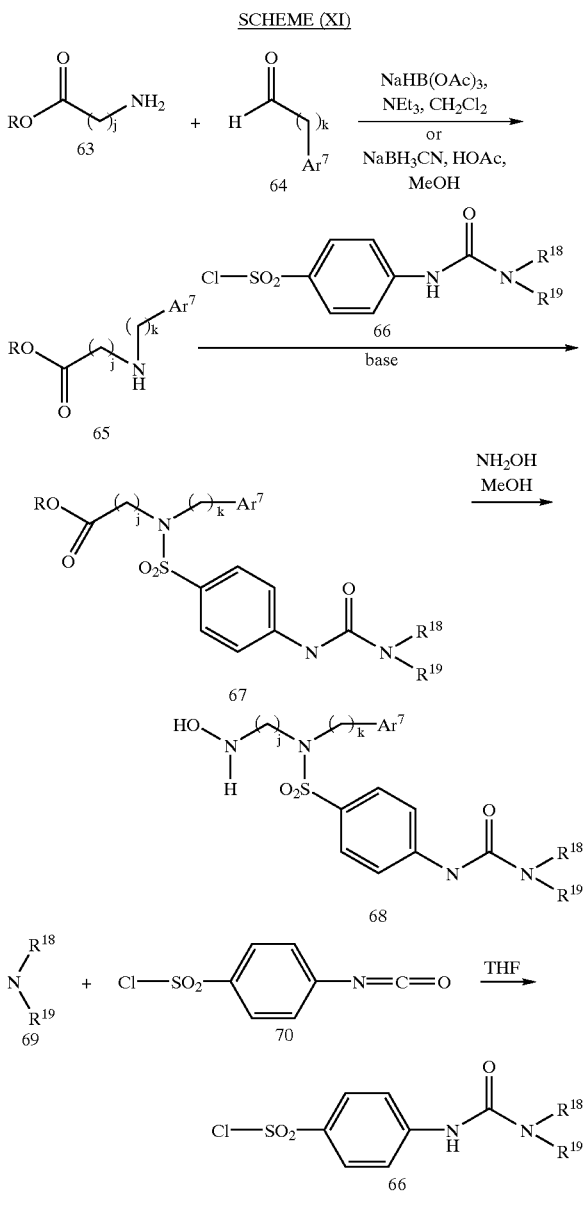

In Scheme (XI), j is an integer from 1 to 4;

k is an integer from 0 to 4;

$Ar^7$ is selected from the group consisting of ($C_5$–$C_{20}$) aryl, ($C_5$–$C_{20}$) aryl independently substituted with one or more $Y^7$, 5–20 membered heteroaryl and 5–20 membered heteroaryl independently substituted with one or more $Y^7$;

$R^{18}$ and $R^{19}$ are independently selected from the group consisting of hydrogen, ($C_1$–$C_8$) alkyl, ($C_2$–$C_8$) alkenyl, ($C_5$–$C_{20}$) alkynyl, ($C_3$–$C_{10}$) cycloalkyl, ($C_5$–$C_{20}$) aryl, ($C_5$–$C_{20}$) substituted aryl, ($C_6$–$C_{26}$) alkaryl, ($C_6$–$C_{26}$) substituted alkaryl, 5–20 membered heteroaryl, 5–20 membered substituted heteroaryl, 6–26 membered alk-heteroaryl; and 6–26 membered substituted alk-heteroaryl;

each $Y^7$ is independently selected from the group consisting of an electron-donating functional group, an electron-withdrawing functional group, and a lipophilic functional group; and R is methyl or ethyl.

Typical electron-donating functional groups that are independently selected for $Y^7$ in compounds of formula (IV) include, but are not limited to —Cl, —R, —OR, —SR, and —NRR; where each R is independently H, ($C_1$–$C_8$) alkyl, ($C_2$–$C_8$) alkenyl or ($C_2$–$C_8$) alkynyl. Particularly preferred electron-donating groups are —Cl and —OCH$_3$.

Typical electron-withdrawing functional groups that are independently selected for $Y^7$ in compounds of formula (IV) include, but are not limited to —F, —NO, —NO$_2$, —CN, -trihalomethyl, and —SO$_2$NHR; where R is independently H, ($C_1$–$C_8$) alkyl, ($C_2$–$C_8$) alkenyl, ($C_2$–$C_8$) alkynyl, ($C_5$–$C_{20}$) aryl, ($C_6$–$C_{26}$) alkaryl, 5–20 membered heteroaryl and 6–26 membered alk-heteroaryl as defined herein.

Typical lipophilic functional groups that are selected for $Y^7$ include, but are not limited to n-butyl, alkoxy such as butoxy, and bromo.

According to Scheme (XI), to a solution of compound 63 in anhydrous methylene chloride at room temperature is added triethyl amine and compound 64. After the mixture is stirred, sodium triacetoxyborohydride is added and the reaction mixture is stirred for additional period of time to yield compound 65. To compound 65 is added compound 66 and triethyl amine. The resulting mixture is stirred and then quenched with citric acid yielding compound 67. To compound 67 in methanol is added freshly prepared NH$_2$OH solution. The mixture is stirred and concentrated to yield compound 68.

Compound 66 is prepared by the following method. To a solution of primary or secondary amine 69 (0.5 mmol) in THF (1 mL) at 0° C. was added 4-(chlorosulfonyl)phenyl isocyanate 70 (0.5 mmol). After stirring at 0° C. for 2 h, the mixture was concentrated to afford 4-(3-substituted-ureido) benzenesulfonyl chloride 66.

SCHEME (XII)

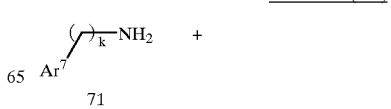

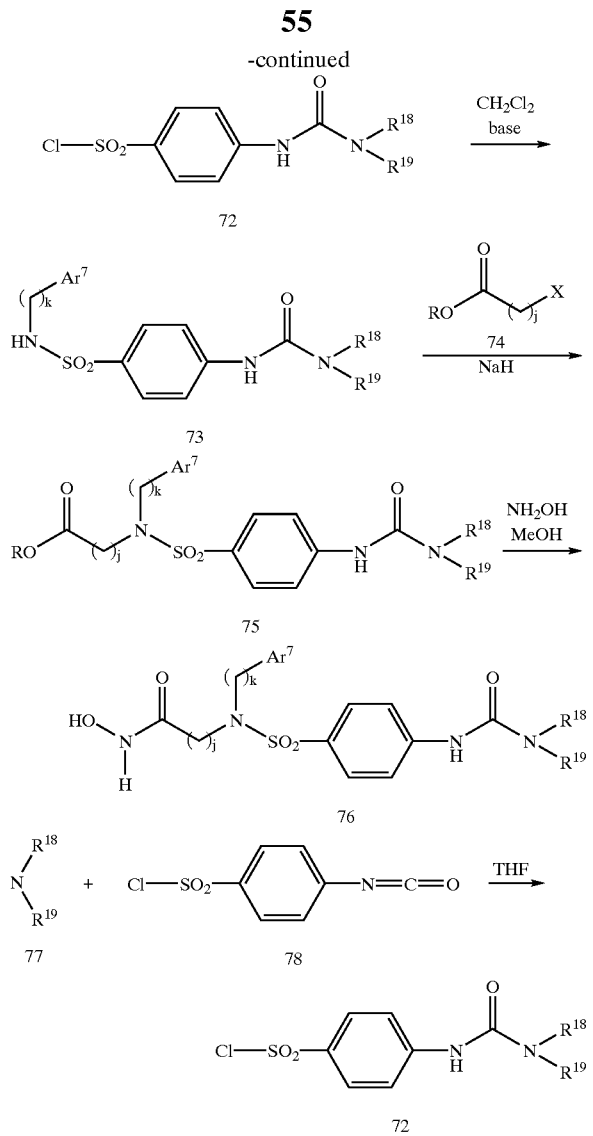

In Scheme (XII), j is an integer from 1 to 4;

k is an integer from 0 to 4;

$Ar^7$ is selected from the group consisting of $(C_5–C_{20})$ aryl, $(C_5–C_{20})$ aryl independently substituted with one or more $Y^7$, 5–20 membered heteroaryl and 5–20 membered heteroaryl independently substituted with one or more $Y^7$;

$R^{18}$ and $R^{19}$ are independently selected from the group consisting of hydrogen, $(C_1–C_8)$ alkyl, $(C_2–C_8)$ alkenyl, $(C_2–C_8)$ alkynyl, $(C_3–C_{10})$ cycloalkyl, $(C_5–C_{20})$ aryl, $(C_5–C_{20})$ substituted aryl, $(C_6–C_{26})$ alkaryl; $(C^6–C_{26})$ substituted alkaryl, 5–20 membered heteroaryl, 5–20 membered substituted heteroaryl, 6–26 membered alk-heteroaryl, and 6–26 membered substituted alk-heteroaryl;

each $Y^7$ is independently selected from the group consisting of an electron-donating functional group, an electron-withdrawing functional group, and a lipophilic functional group;

R is methyl or ethyl; and

X is chloro or bromo.

Typical electron-donating functional groups that are independently selected for $Y^7$ in compounds of formula (XII) include, but are not limited to —Cl, —R, —OR, —SR, and —NRR; where each R is independently H, $(C_1–C_8)$ alkyl, $(C_2–C_8)$ alkenyl or $(C_2–C_8)$ alkynyl. Particularly preferred electron-donating groups are —Cl and —OCH$_3$.

Typical electron-withdrawing functional groups that are independently selected for $Y^7$ in compounds of formula (XII) include, but are not limited to —F, —NO, —NO$_2$, —CN, -trihalomethyl, and —SO$_2$NR; where R is independently H, $(C_1–C_8)$ alkyl, $(C_2–C_8)$ alkenyl, $(C_2–C_8)$ alkynyl, $(C_5–C_{20})$ aryl, $(C_6–C_{26})$ alkaryl, 5–20 membered heteroaryl and 6–26 membered alk-heteroaryl as defined herein.

Typical lipophilic functional groups that are selected for $Y^7$ include, but are not limited to n-butyl, alkoxy such as butoxy, and bromo.

According to Scheme (XII), a primary amine 71 is dissolved in methylene chloride, followed by the addition of benzylsulfonyl chloride 72 and Amberlyst weakly basic ion exchange resin to yield compound 73. Compound 73 is dissolved in dry DMF and stirred under argon. To this mixture is added sodium hydride 60% suspended in mineral oil and the resulting mixture stirred. To this mixture is added compound 74 to yield compound 75 after silica gel chromatography. To compound 75 is added freshly prepared NH$_2$OH (1 M in methanol). The mixture is stirred to afford compound 76. Depending on the chemical properties of compound 76, it is worked up as follows:

Hydrophobic compounds 76 are treated with a HCl solution and extracted with ethyl acetate. The organic layer is dried over MgSO$_4$, filtered, and concentrated. The residue is then triturated with ether to remove undesired products which are discarded. The solid is collected and dried in vacco.

Hydrophilic compounds 76 are triturated with ethyl acetate twice. Ethyl acetate is decanted and discarded. The residue is treated with water, neutralized by 1 N HCl solution to pH=7–8, and extracted with 10/1 ethyl acetate/methanol. The combined organic layers is washed with brine, dried over magnesium sulfate, filtered, and concentrated. The residue is triturated in ether, which is discarded, and dried in vacco to furnish the product as a white solid.

Preparation of (compound 72) 4-(3-Substituted-ureido)-benzenesulfonyl Chloride: To a solution of primary or secondary amine 77 (0.5 mmol) in THF (1 mL) at 0° C. is added 4-(chlorosulfonyl)phenyl isocyanate 78 (0.5 mmol). After stirring at 0° C. for 2 h, the mixture was concentrated to afford 4-(3-substituted-ureido)benzenesulfonyl chloride 72.

SCHEME (XIII)

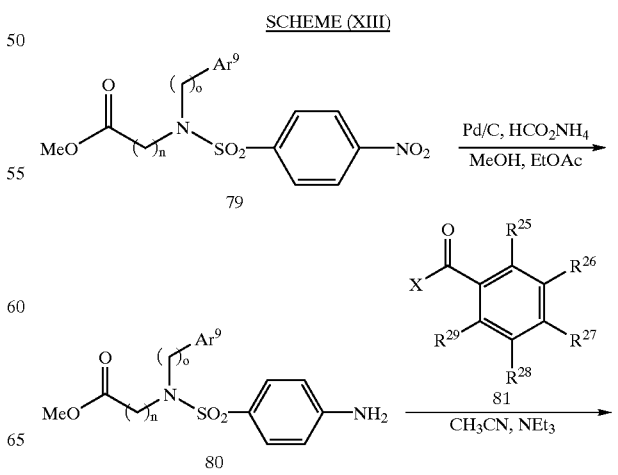

-continued

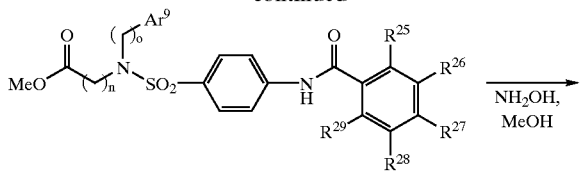
82

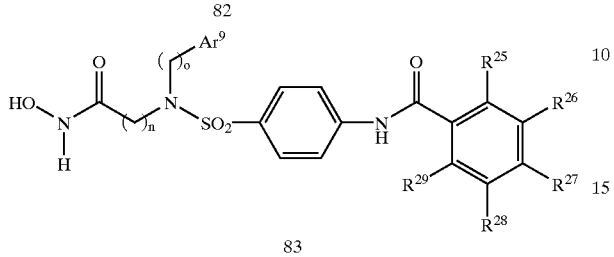
83

In Scheme (XIII),
n is an integer from 1 to 4;
o is an integer from 0 to 4;
$Ar^9$ is selected from the group consisting of $(C_5-C_{20})$ aryl, $(C_5-C_{20})$ aryl independently substituted with one or more $Y^9$, 5–20 membered heteroaryl and 5–20 membered heteroaryl independently substituted with one or more $Y^9$;
each $R^{25}$, $R^{26}$, $R^{27}$, $R^{28}$, $R^{29}$ and $Y^9$ is independently selected from the group consisting of an electron-donating functional group, an electron-withdrawing functional group, and a lipophilic functional group; and
X is chloro or bromo.

Typical electron-donating functional groups that are independently selected for $Y^9$ include, but are not limited to —Cl, —R, —OR, —SR, and —NRR; where each R is independently H, $(C_1-C_8)$ alkyl, $(C_2-C_8)$ alkenyl or $(C_2-C_8)$ alkynyl. Particularly preferred electron-donating groups are Cl and —OCH$_3$.

Typical electron-withdrawing functional groups that are independently selected for $Y^9$ include, but are not limited to —F, —NO, —NO$_2$, —CN, -trihalomethyl, and —SO$_2$NHR; where R is independently H, $(C_1-C_8)$ alkyl, $(C_2-C_8)$ alkenyl, $(C_2-C_8)$ alkynyl, $(C_5-C_{20})$ aryl, $(C_6-C_{26})$ alkaryl, 5–20 membered heteroaryl and 6–26 membered alkheteroaryl as defined herein.

Typical lipophilic functional groups that are selected for $Y^9$ include, but are not limited to n-butyl, alkoxy such as butoxy, and halogen.

According to scheme (XIII), to a solution of 79 in 5:1 methanol/ethyl acetate (4.2 mL/mmol) is added by portion palladium (10%) in charcoal solid (10% w/w), followed by ammonium formate (4 eq.). The resulting mixture is refluxed for 6 hours and filtered through a pad of celite. Filtrate is concentrated and partitioned between ethyl acetate and water. Organic layer is washed with brine, dried over sodium sulfate, filtered and concentrated to give 80. To a solution of 80 in acetonitrile (7.8 mL/mmol) is added the corresponding electrophile (1.1 eq.) substituted benzoyl halide 81 followed by triethyl amine (2 eq.). The mixture is stirred at room temperature for 5 hours and then partitioned between methylene chloride and 0.1 N hydrochloric acid aqueous solution. The acid layer is extracted with methylene chloride. Combined organic layers are washed with brine, dried over magnesium sulfate, filtered, and concentrated. The residue is then treated with 10 equivalents of freshly prepared neutralized NH$_2$OH (1 M in methanol). The mixture is stirred at room temperature for 5 hours and concentrated to yield residue 82. Residue 82 is partitioned between 10:1 ethyl acetate/methanol and 1 N hydrochloric acid aqueous solution. The organic layer is washed with brine, dried over magnesium sulfate, filtered, and concentrated to give the corresponding hydroxamic acid 83.

SCHEME (XIV)

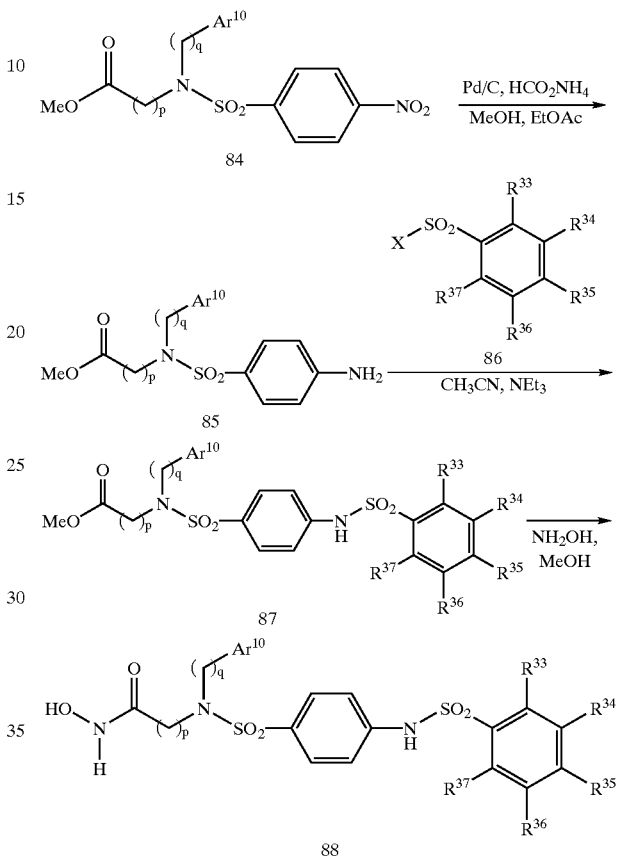

In Scheme (XIV),
p is an integer from 1 to 4;
q is an integer from 0 to 4;
$Ar^{10}$ is selected from the group consisting of $(C_5-C_{20})$ aryl, $(C_5-C_{20})$ aryl independently substituted with one or more $Y^8$, 5–20 membered heteroaryl and 5–20 membered heteroaryl independently substituted with one or more $Y^{10}$;
each $R^{33}$, $R^{34}$, $R^{35}$, $R^{36}$, $R^{37}$ and $Y^{10}$ is independently selected from the group consisting of an electron-donating functional group, an electron-withdrawing functional group, and a lipophilic functional group; and
X is chloro or bromo.

Typical electron-donating functional groups that are independently selected for $Y^{10}$ include, but are not limited to —Cl, —R, —OR, —SR, and —NRR, where each R is independently H, $(C_1-C_8)$ alkyl, $(C_2-C_8)$ alkenyl or $(C_2-C_8)$ alkynyl. Particularly preferred electron-donating groups are —Cl and —OCH$_3$.

Typical electron-withdrawing functional groups that are independently selected for $Y^{10}$ include, but are not limited to —F, —NO, —NO$_2$, —CN, -trihalomethyl, and —SO$_2$NHR; where R is independently H, $(C_1-C_8)$ alkyl, $(C_2-C_8)$ alkenyl, $(C_2-C_8)$ alkynyl, $(C_5-C_{20})$ aryl, $(C_6-C_{26})$ alkaryl, 5–20 membered heteroaryl and 6–26 membered alkheteroaryl as defined herein.

Typical lipophilic functional groups that are selected for $Y^{10}$ include, but are not limited to, n-butyl, alkoxy such as butoxy, and bromo.

According to scheme (XIV), to a solution of 84 in 5:1 methanol/ethyl acetate (4.2 mL/mmol) is added by portion palladium (10%) in charcoal solid (10% w/w), followed by ammonium formate (4 eq.). The resulting mixture is refluxed for 6 hours and filtered through a pad of celite. Filtrate is concentrated and partitioned between ethyl acetate and water. Organic layer is then washed with brine, dried over sodium sulfate, filtered and concentrated to give 85. To a solution of 85 in acetonitrile (7.8 mL/mmol) is added the corresponding electrophile (1.1 eq.) substituted benzenesulfonyl halide 86 followed by triethyl amine (2 eq.). The mixture is stirred at room temperature for 5 hours and then partitioned between methylene chloride and 0.1 N hydrochloric acid aqueous solution. The acid layer is extracted with methylene chloride. Combined organic layers are washed with brine, dried over magnesium sulfate, filtered, and concentrated to yield 87. Residue 87 is then treated with 10 equivalents of freshly prepared neutralized $NH_2OH$ (1 M in methanol). The mixture is stirred at room temperature for 5 hours and concentrated to yield residue 88. Residue 88 is partitioned between 10:1 ethyl acetate/methanol and 1 N hydrochloric acid aqueous solution. The organic layer is washed with brine, dried over magnesium sulfate, filtered, and concentrated to give isolated hydroxamic acid 88.

SCHEME (XV)

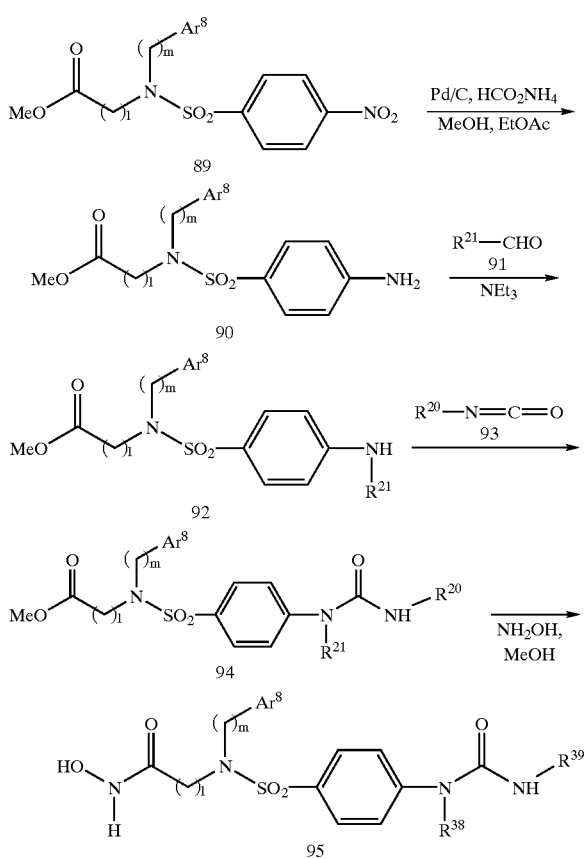

In Scheme (XV),
l is an integer from 1 to 4;
m is an integer from 0 to 4;
$Ar^8$ is selected from the group consisting of $(C_5-C_{20})$ aryl, $(C_5-C_{20})$ aryl independently substituted with one or more $Y^8$, 5–20 membered heteroaryl, and 5–20 membered heteroaryl independently substituted with one or more $Y^8$;

$R^{20}$ is independently selected from the group consisting of H, $(C_1-C_8)$ alkyl, $(C_2-C_8)$ alkenyl, and $(C_2-C_8)$ alkynyl; and $R^{21}$ is selected from the group consisting of hydrogen, $(C_1-C_8)$ alkyl, $(C_2-C_8)$ alkenyl, $(C_2-C_8)$ alkynyl, $(C_3-C_{10})$ cycloalkyl, $(C_5-C_{20})$ aryl, $(C_5-C_{20})$ substituted aryl, $(C_6-C_{26})$ alkaryl, $(C_6-C_{26})$ substituted alkaryl, 5–20 membered heteroaryl, 5–20 membered substituted heteroaryl, 6–26 membered alk-heteroaryl, and 6–26 membered substituted alk-heteroaryl.

According to Scheme (XV) to a solution of 89 in 5:1 methanol/ethyl acetate (4.2 mL/mmol) is added by portion palladium (10%) in charcoal solid (10% w/w), followed by ammonium formate (4 eq.). The resulting mixture is refluxed for 6 hours and filtered through a pad of celite. Filtrate is concentrated and partitioned between ethyl acetate and water. Organic layer is washed with brine, dried over sodium sulfate, filtered and concentrated to give 90. To a solution of 90 is added aldehyde 91 followed by triethyl amine to yield compound 92. To compound 92 is added compound 93 to yield compound 94. Compound 94 is treated with 10 equivalents of freshly prepared $NH_2OH$ (1 M in methanol). The mixture is stirred at room temperature for 5 hours and concentrated to yield residue 95.

5.3 Biological and Pharmacological Activity

An individual compound's relevant activity and potency as an inhibitor of C-proteinase, to regulate or modulate collagen production or maturation and/or to treat disorders associated with unregulated collagen production may be determined using available techniques.

Typically, active compounds of the invention will inhibit 50% of the activity of C-proteinase at concentrations in the range of 100 micromolar (µM) or less (i.e., those compounds exhibiting an $IC_{50}$ of 100 µM or less) using standard biochemical assays (Dickson, 1953, Biochem. J. 55:170–171; Knight et al., 1992, FEBS 296:263–266). Those of skill in the art will appreciate that compounds exhibiting lower inhibitory concentrations ($IC_{50}$s) are generally preferred for pharmacological applications; thus, preferably active compounds will exhibit $IC_{50}$s that are less than 10 µM, more preferably less than 1 µM, even more preferably less than 100 nanomolar (nM) and even more preferably less than about 10 nM or 1 nM. However, as compounds which exhibit $IC_{50}$s in the millimolar (mM) range can provide consequential pharmacological benefits, compounds which exhibit $IC_{50}$s as high as 1 mM to 10 mM are considered to possess biological or pharmacological activity.

Alternatively, an in vitro procollagen assay may be used to determine the level of activity and effect of different compounds of the present invention on C-proteinase activity. In the procollagen assay, about 125 ug radiolabeled ($^{14}$C) procollagen is added to 10 units/mL of chicken C-proteinase in a solution of 0.1 M Tris-HCl, 0.1 M NaCl, 0.02% Brij-35, and 5 mM $CaCl_2$ in a total volume of 10 µl. The reaction is allowed to proceed for 15 minutes at 35° C. and is stopped with one-half volume of 3× stop/loading buffer (30 mM EDTA, 30% glycerol, 6% SDS, 0.006% Bromophenolblue). Subsequently, the samples are heated to 100° C. for 4 minutes, and resolved by SDS-PAGE (Novex) using 6% polyacryleamide gels. The protein bands are detected by autoradiography. The amount of enzyme activity is based on the disappearance of the band corresponding to uncleaved procollagen. The $IC_{50}$ of inhibitors can be determined by plotting the % activity versus inhibitor concentration and estimating the inhibitor concentration which results in 50% activity.

5.4 Indications

Disorders associated with unregulated collagen production or maturation can be treated with the compounds and compositions of the present invention. While not intending to be bound by any particular theory, it is believed that when administered to an animal subject, including a human, the compounds of the invention inhibit C-proteinase in vivo, thereby effectively modulating, regulating or inhibiting collagen production or maturation. As a consequence, the compounds are able to treat or prevent disorders associated with unregulated collagen production or maturation.

Collagen-related disorders which can be treated or prevented according to the invention include pathological fibrosis or scarring, such as endocardial sclerosis, idiopathic interstitial fibrosis, interstitial pulmonary fibrosis, perimuscular fibrosis, Symmers' fibrosis, pericentral fibrosis, hepatitis, dermatofibroma, binary cirrhosis, alcoholic cirrhosis, acute pulmonary fibrosis, idiopathic pulmonary fibrosis, acute respiratory distress syndrome, kidney fibrosis/glomerulonephritis, kidney fibrosis/diabetic nephropathy, scleroderma/systemic, scleroderma/local, keloids, hypertrophic scars, severe joint adhesions/arthritis, myelofibrosis, corneal scarring, cystic fibrosis, muscular dystrophy (duchenne's), cardiac fibrosis, muscular fibrosis/retinal separation, esophageal stricture, payronles disease. Further, fibrotic disorders may be induced or initiated by surgery such as scar revision/plastic surgeries, glaucoma, cataract fibrosis, corneal scarring, joint adhesions, graft vs. host disease, tendon surgery, nerve entrapment, dupuytren's contracture, OB/GYN adhesions/fibrosis, pelvic adhesions, peridural fibrosis, restenosis. Still further fibrotic disorders may be induced by chemotherapy, including, for example lung fibrosis and the like.

5.5 Pharmaceutical Formulations and Routes of Administration

The compounds described herein, or pharmaceutically acceptable addition salts or hydrates thereof, can be delivered to a subject, including a human, using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, the compounds of the invention can be administered in cocktails containing agents used to treat the pain and other symptoms and side effects commonly associated with fibrotic disorders. The compounds can also be administered in cocktails containing other agents that are commonly used to treat fibrotic disorders.

The active compound(s) may be administered per se or in the form of a pharmaceutical composition containing the active compound(s) and one or more pharmaceutically acceptable carriers, excipients or diluents. Administered compounds may be enantiomerically pure, or may be mixtures of enantiomers. Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations previously described, the compounds may also be formulated as a depot preparation. Such long acting formulations may be administered by implantation or transcutaneous delivery (for example subcutaneously or intramuscularly), intramuscular injection or a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

5.5.1 Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the C-proteinase activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p. 1.

Dosage amount and interval may be adjusted individually to provide plasma levels of the active moiety which are sufficient to maintain the C-proteinase inhibiting effects, or minimal effective concentration (MEC). The MEC will vary for each compound but can be estimated from in vitro data; for example, the concentration necessary to achieve 50–90% inhibition of the C-proteinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

5.5.2 Packaging

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Suitable conditions indicated on the label may include treatment of arthritis or any other fibrotic disorder.

6. EXAMPLE

Compound Synthesis

The compounds of the present invention may be synthesized according to known techniques. The following represent preferred methods for synthesizing certain compounds of the invention.

6.1 Synthesis of N-Hydroxy-3-[(benzyl)-(4-methoxybenzenesulfonyl)-amino]-propionamide (FG 121)

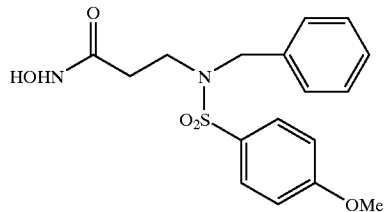

6.1.1 Ethyl 3-[(Benzyl)-(4-methoxybenzenesulfonyl)-amino]-propionate

Ethyl acrylate (1.05 g; 10 mmol) and benzylamine (1.10 g; 10 mmol) were dissolved in absolute ethanol and stirred 18 h at room temperature. The ethanol was removed under reduced pressure and the resulting oil dissolved CH$_2$Cl$_2$ (20 mL). p-Methoxybenzenesulfonyl chloride (2.10 g; 10 mmol) and triethylamine (1.05 g; 10 mmol) were added, and the resulting solution stirred at room temperature 5 h. The reaction was diluted with CH$_2$Cl$_2$ (30 mL) and washed with 1 N HCl (2×50 mL) and the aqueous layers back-extracted with fresh CH$_2$Cl$_2$ (50 mL). The organic layers were combined, dried over MgSO$_4$, filtered and evaporated. Preparative HPLC purification, eluting with a mixture of ethyl acetate/hexanes (35:65) gave 3.36 g (89%) of the title compound as a pale yellow oil. 300 MHz $^1$H-NMR (CDCl$_3$): δ 1.18 (t, 3H), 2.42 (m, 2H), 3.38 (m, 2H), 3.89 (s, 3H), 4.02 (m, 2H), 4.32 (s, 2H), 7.00 (m, 2H), 7.30 (m, 5H), 7.79 (m, 2H).

6.1.2 N-Hydroxy-3-[(benzyl)-(4-methoxybenzenesulfonyl)-amino]-propionamide

Freshly prepared hydroxylamine reagent (20 mL; 20 mmol) was added to ethyl 3-[(benzyl)-(4-methoxybenzenesulfonyl)-amino]-propionate (3.30 g; 8.8 mmol) and the resulting mixture stirred for 18 h at room temperature. The mixture was poured into 1 N HCl (100 mL) and extracted with CH$_2$Cl$_2$ (2×10 mL). The combined extracts were washed with saturated aqueous NaCl (1×10 mL), dried over MgSO$_4$, and evaporated under reduced pressure to give a crude gum. Trituration with diethyl ether afforded 2.33 g (68%) of the title compound as an off-white solid. 300 MHz $^1$H-NMR (DMSO-d$_6$): δ 2.06 (m, 2H), 3.25 (m, 2H), 3.87 (s, 3H), 4.33 (s, 2H), 7.16 (d, 2H), 7.20–7.42 (m, 5H), 7.80 (d, 2H), 8.70 (bs, 1H), 10.38 (s, 1H).

6.2 Synthesis of N-Benzyl-N-p-methohybenzene Sulfonyl-G-Amilobutyryl Hydroxamic Acid (FG 122)

6.2.1 N-Benzyl p-methoxybenzenesulfonamide

Benzylamine (3.75 g; 35 mmol), p-methoxybenzenesulfonyl chloride (6.20 g; 30 mmol), and triethylamine (3.20 g; 31 mmol) were dissolved in CH$_2$Cl$_2$ (50 mL) and the resulting solution stirred 20 h at room temperature. The solution was washed with 0.5 N HCl (2×50 mL) and the aqueous layers back-extracted with additional CH$_2$Cl$_2$ (50 mL). The combined organic layers were dried over MgSO$_4$, filtered, and evaporated to give 7.05 g (85%) of the title compound as a white solid. $^1$H-NMR (CDCl$_3$): δ 3.88 (s, 3H), 4.12 (d, 2H), 4.92 (t, 1H), 6.97 (d, 2H), 7.18–7.30 (m, 5H), 7.80 (d, 2H).

6.2.2 Ethyl N-Benzyl-p-methoxybenzenesulfonyl-γ-aminobutyrate

N-Benzyl p-methoxybenzenesulfonamide (2.77 g; 10 mmol) was dissolved in dry DMF (35 mL) and stirred under argon. Sodium hydride, 60% in mineral oil (0.55 g; 14 mmol), was added and the resulting mixture stirred at room temperature for 0.5 h. Ethyl 4-bromobutyrate (2.95 g; 15 mmol) and sodium iodide (250 mg) were added successively and the reaction heated to 90° C. for 6 h. After cooling to room temperature, the mixture was poured into diethyl ether (100 mL) and extracted with water (2×100 mL). The organic layer was dried over MgSO$_4$, filtered and evaporated to an oil. Preparative HPLC purification, eluting with a mixture of ethyl acetate/hexanes (35:65) gave 3.62 g (93%) of the title compound as an oil.
$^1$H-NMR (CDCl$_3$): δ 1.20 (t, 3H), 1.65 (m, 2H), 2.16 (t, 2H), 3.14 (m, 2H), 3.88 (s, 3H), 4.05 (m, 2H), 4.30 (s, 2H), 6.90 (m, 2H), 7.29 (m, 5H), 7.77 (m, 2H).

6.2.3 N-Benzyl-N-p-methoxybenzenesulfonyl-γ-aminobutyryl Hydroxamic Acid

Freshly prepared hydroxylamine reagent (20 mL; 20 mmol) was added to ethyl N-phenyl-N-p-methoxybenzenesulfonyl-β-alaninate (3.55 g; 9.1 mmol) and the resulting mixture stirred for 18 h at room temperature. The mixture was poured into 1 N HCl (100 mL) and extracted with CH$_2$Cl$_2$ (2×100 mL). The combined extracts were washed with saturated aqueous NaCl (1×100 mL), dried over MgSO$_4$, and evaporated under reduced pressure to give a crude gum. Trituration with diethyl ether afforded 1.83 g (55%) of the title compound as a tan solid.
$^1$H-NMR (DMSO-d$_6$): δ 1.46 (m, 2H), 1.77 (t, 2H) 3.03 (t, 2H), 3.86 (s, 3H), 4.28 (s, 2H), 7.12 (d, 2H), 7.38 (m, 5H), 7.80 (d, 2H), 8.66 (s, 1H), 10.22 (s, 1H).

6.3 Synthesis of N-Phenyl-N-p-methoxibenzene Sulfonyl-glycine Hydroxamic Acid (FG 123)

6.3.1 N-Phenyl-N-p-methoxybenzenesulfonyl-glycinate

N-Phenyl p-methoxybenzenesulfonamide aniline (2.80 g; 30 mmol), p-methoxybenzenesulfonyl chloride (6.20 g; 30 mmol), and triethylamine (3.20 g; 31 mmol) were dissolved in CH$_2$Cl$_2$ (50 mL) and the resulting solution stirred 18 h at room temperature. The solution was washed with 0.5 N HCl (2×50 mL) and the aqueous layers back-extracted with additional CH$_2$Cl$_2$ (50 mL). The combined organic layers were dried over MgSO$_4$, filtered and evaporated to give 6.66 g (84%) of the title compound as a thick oil that solidified upon standing.
$^1$H-NMR (CDCl$_3$): δ 3.79 (s, 3H), 6.87 (d, 2H), 7.10 (d, 2H), 7.21 (m, 3H), 7.75 (m, 2H).

6.3.2 Ethyl N-Phenyl-N-p-methoxybenzenesulfonyl-glycinate

N-Phenyl p-methoxybenzenesulfonamide (2.63 g; 10 mmol) was dissolved in dry THF (50 mL) and stirred under argon. Sodium hydride, 60% in mineral oil (0.55 g; 14 mmol), was added and the resulting mixture stirred at room temperature for 0.5 h. Ethyl bromoacetate (2.50 g; 15 mmol) and sodium iodide (200 mg) were added successively and the reaction stirred at room temperature for 72 h. The mixture was poured into diethyl ether (100 mL) and extracted with water (2×100 mL). The organic layer was dried over MgSO$_4$, filtered, and evaporated to a semi-solid. Preparative HPLC purification, eluting with a mixture of ethyl acetate/hexanes (35:65) gave 2.80 g (80%) of the title compound as a light yellow solid.
$^1$H-NMR (CDCl$_3$): δ 1.22 (t, 3H), 3.86 (s, 3H), 4.12 (m, 2H), 4.40 (s, 2H), 6.89 (m, 2H), 7.17–7.32 (m, 5H), 7.61 (d, 2H).

6.3.3 N-Phenyl-N-p-methoxybenzenesulfonyl-glycine Hydroxamic Acid

Freshly prepared hydroxylamine reagent (16 mL; 16 mmol) was added to ethyl N-phenyl-N-p-methoxybenzenesulfonyl-glycinate (2.80 g; 8.0 mmol) and the resulting mixture stirred for 6 h at room temperature. The mixture was poured into 1 N HCl (100 mL) and extracted with $CH_2Cl_2$ (2×100 mL). The combined extracts were washed with saturated aqueous NaCl (1×100 mL), dried over $MgSO_4$, and evaporated under reduced pressure to give crude product. Trituration with diethyl ether afforded 1.75 g (65%) of the title compound as a white solid.

$^1$H-NMR (DMSO-$d_6$): δ 3.83 (s, 3H), 4.13 (s, 2H), 7.03–7.15 (2 m, 4H), 7.30 (m, 3H), 7.54 (d, 2H), 8.89 (bs, 1H), 10.60 (s, 1H).

6.4 Synthesis of N-Hydroxy-3-[(phenyl)-(4-methoxybenzenesulfonyl)-amino]-propionamide (FG 124)

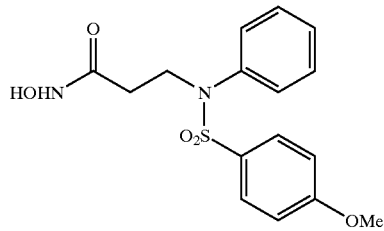

6.4.1 Ethyl 3-Phenylamino-propionate

Ethyl acrylate (2.05 g; 20 mmol) and aniline (1.85 g; 20 mmol) were added to a solution of concentrated HCl (1.5 mL) in absolute ethanol (20 mL) and the resulting mixture refluxed 20 h. The reaction was cooled to room temperature and then poured into 1 N NaOH (100 mL) and extracted with ethyl acetate (2×100 mL). The combined organic layers were washed with water (2×100 mL), dried over $MgSO_4$, filtered, and evaporated to give 2.85 g (80%) of the title compound as a light amber oil. 300 MHz $^1$H-NMR (CDCl$_3$): δ 1.27 (t, 3H), 2.61 (t, 2H), 3.46 (t, 2H), 4.16 (q, 2H), 6.63 (d, 2H), 6.72 (m, 1H), 7.17 (m, 2H).

6.4.2 Ethyl 3-[(Phenyl)-(4-methoxybenzenesulfonyl)-amino]-propionate

The crude oil of ethyl 3-phenylamino-propionate (1.78; 10 mmol) and p-methoxybenzenesulfonyl chloride (2.10 g; mmol) were dissolved in $CH_2Cl_2$ (20 mL). Triethylamine (1.05 g; 10 mmol) was added and the resulting mixture stirred at room temperature overnight. The reaction was diluted with $CH_2Cl_2$ (30 mL) and washed with 1 N HCl (2×50 mL) and the aqueous layers back-extracted with fresh $CH_2Cl_2$ (50 mL). The organic layers were combined, dried over $MgSO_4$, filtered and evaporated. Preparative HPLC purification, eluting with ethyl acetate/hexanes (35:65) gave 3.34 g (92%) of the title compound as a light yellow oil. 300 MHz $^1$H-NMR (CDCl$_3$): δ 1.19 (t, 3H), 2.53 (m, 2H), 3.84 (m, 2H), 3.86 (s, 3H), 4.05 (m, 2H), 6.91 (m, 2H), 7.03 (m, 2H), 7.29 (m, 3H), 7.53 (m, 2H).

6.4.3 N-Hydroxy-3-[(phenyl)-(4-methoxybenzenesulfonyl)-amino]-propionamide

Freshly prepared hydroxylamine reagent (20 mL; 20 mmol) was added to ethyl 3-[(phenyl)-(4-methoxybenzenesulfonyl)-amino]-propionate (3.30 g; 9.1 mmol) and the resulting mixture stirred for 18 h at room temperature. The mixture was poured into 1 N HCl (100 mL) and extracted with $CH_2Cl_2$ (2×100 mL). The combined extracts were washed with saturated aqueous NaCl (1×100 mL), dried over $MgSO_4$, and evaporated under reduced pressure to give a crude gum. Trituration with diethyl ether afforded 2.14 g (68%) of the title compound as an off-white solid. 300 MHz $^1$H-NMR (DMSO-$d_6$): δ 2.12 (t, 2H), 3.74 (t, 2H), 3.86 (s, 3H), 7.03 (d, 2H), 7.08 (d, 2H), 7.32 (m, 3H), 7.47 (d, 2H), 8.74 (s, 1H), 10.35 (s, 1H).

6.5 Synthesis of N-Phenyl-N-p-methoxybenzene Sulfonyl-G-aminobutyryl Hydroxamic Acid (FG 125)

6.5.1 Ethyl N-Phenyl-N-p-methoxybenzenesulfonyl-γ-aminobutyrate

N-Phenyl p-methoxybenzenesulfonamide (2.63 g; 10 mmol) was dissolved in dry DMF (35 mL) and stirred under argon. Sodium hydride, 60% in mineral oil (0.55 g; 14 mmol), was added and the resulting mixture stirred at room temperature for 0.5 h. Ethyl 4-bromobutyrate (2.95 g; 15 mmol) and sodium iodide (250 mg) were added successively and the reaction heated to 90° C. for 24 h. After cooling to room temperature, the mixture was poured into diethyl ether (100 mL) and extracted with water (2×100 mL). The organic layer was dried over $MgSO_4$, filtered and evaporated to a solid. Preparative HPLC purification, eluting with a mixture of ethyl acetate/hexanes (35:65) gave 3.56 g (91%) of the title compound as a white solid.

$^1$H-NMR (CDCl$_3$): δ 1.22 (t, 3H), 1.73 (m, 2H), 2.39 (t, 2H), 3.59 (t, 2H), 3.86 (s, 3H), 4.19 (m, 2H), 6.91 (m, 2H), 7.05 (m, 2H), 7.31 (m, 3H), 7.49 (m, 2H).

6.5.2 N-Phenyl-N-p-methoxybenzenesulfonyl-γ-aminobutyryl Hydroxamic Acid

Freshly prepared hydroxylamine reagent (20 mL; 20 mmol) was added to ethyl N-phenyl-N-p-methoxybenzenesulfonyl-b-alaninate (3.50 g; 9.0 mmol) and the resulting mixture stirred for 18 h at room temperature. The mixture was poured into 1 N HCl (100 mL) and extracted with $CH_2Cl_2$ (2×100 mL) The combined extracts were washed with saturated aqueous NaCl (1×100 mL), dried over $MgSO_4$, and evaporated under reduced pressure to give a crude gum. Trituration with diethyl ether afforded 2.25 g (69%) of the title compound as an off-white solid.

$^1$H-NMR (DMS0-$d_6$): δ 2.12 (t, 2H), 3.74 (t, 2H), 3.86 (s, 3H), 7.03 (d, 2H), 7.08 (d, 2H), 7.32 (m, 3H), 7.47 (d, 2H), 8.74 (s, 1H), 10.35 (s, 1H).

6.6 Synthesis of N-Hydroxy-3-[(phenethyl)-(4-methoxybenzenesulfonyl)-amino]-propionamide (FG 126)

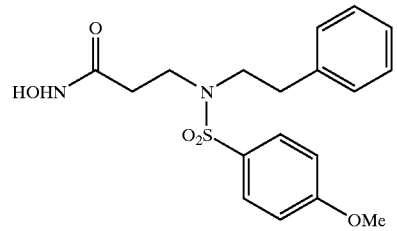

6.6.1 Ethyl 3-[(Phenethyl)-(4-methoxybenzenesulfonyl)-amino]-propionate

Ethyl acrylate (1.05 g; 10 mmol) and phenethylamine (1.21 g; 10 mmol) were dissolved in absolute ethanol and stirred 16 h at room temperature. The ethanol was removed under reduced pressure and the resulting oil dissolved $CH_2Cl_2$ (20 mL). p-Methoxybenzenesulfonyl chloride (2.10 g; 10 mmol) and triethylamine (1.05 g; 10 mmol) were added, and the resulting solution stirred at room temperature 20 h. The reaction was diluted with CH₂Cl₂ (30 mL) and washed with 1 N HCl (2×50 mL) and the aqueous layers back-extracted with fresh CH₂Cl₂ (50 mL). The organic layers were combined, dried over MgSO₄, filtered and evaporated. Preparative HPLC purification, eluting with a mixture of ethyl acetate/hexanes (35:65) gave 3.56 g (91%) of the title compound as a pale yellow oil. 300 MHz ¹H-NMR (CDCl₃): δ 1.26 (t, 3H), 2.58 (m, 2H), 2.86 (m, 2H), 3.34 (m, 2H), 3.44 (m, 2H), 3.86 (s, 3H), 4.13 (m, 2H), 6.95 (m, 2H), 7.15–7.32 (m, 5H), 7.73 (m, 2H).

6.6.2 N-Hydroxy-3-[(phenethyl)-(4-methoxybenzenesulfonyl)-amino]-propionamide

Freshly prepared hydroxylamine reagent (20 mL; 20 mmol) was added to ethyl 3-[(phenethyl)-(4-methoxybenzenesulfonyl)-amino]-propionate (3.30 g; 9.1 mmol) and the resulting mixture stirred for 18 h at room temperature. The mixture was poured into 1 N HCl (100 mL) and extracted with CH₂Cl₂ (2×100 mL). The combined extracts were washed with saturated aqueous NaCl (1×100 mL), dried over MgSO₄, and evaporated under reduced pressure to give a crude gum. Trituration with diethyl ether afforded 2.23 g (65%) of the title compound as an off-white solid. 300 MHz ¹H-NMR (DMSO-d₆): δ 2.23 (t, 2H), 2.74 (m, 2H), 3.23 (m, 2H), 3.34 (m, 2H), 3.83 (s, 3H), 7.11 (d, 2H), 7.15–7.34 (m, 5H), 7.72 (d, 2H), 8.78 (s, 1H), 10.50 (s, 1H).

6.7 Synthesis of N-(2-Phenyl)ethyl-N-4-methoxybenzenesulfonyl-glycine Hydroxamic Acid (FG 128)

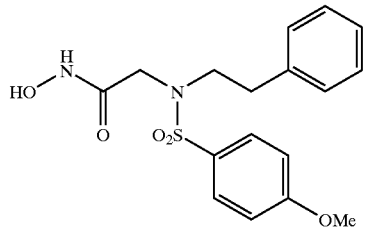

6.7.1 Ethyl-N-(2-phenyl)ethyl-N-4-methoxybenzene-sulfonyl-glycinate

Glycine ethyl ester hydrochloride (1.40 g; 10 mmol), phenylacetaldehyde (1.32 g; 10 mmol), and glacial acetic acid were added to methanol (20 mL) and the resulting solution cooled to 0° C. under argon. After 5 min, sodium cyanoborohydride (0.65 g; 10 mmol) was added in one portion. The reaction was stirred at 0° C. for 2 h and then stirred 16 h at room temperature. The reaction was quenched with the addition of 1 N HCl (30 mL) and the resulting mixture stirred for an additional 1 h. After the removal of methanol under reduced pressure, the remaining aqueous mixture was cooled in an ice bath and carefully basified to pH 10 with 45% (w/w) aqueous KOH, and then extracted with EtOAc (2×50 mL). The combined extracts were washed with solutions of water (50 mL) and saturated aqueous NaCl (50 mL), dried over MgSO₄, and evaporated to an oil. The crude material, p-methoxybenzenesulfonyl chloride (2.10 g; 10 mmol), and triethylamine (1.05 g; 10 mmol) were dissolved in CH₂Cl₂ (20 mL)and the resulting solution stirred at room temperature for 6 h. The reaction was diluted with CH₂Cl₂ (30 mL) and washed with 1 N HCl (2×50 mL) and the aqueous layers back-extracted with fresh CH₂Cl₂ (50 mL). The organic layers were combined, dried over MgSO₄, filtered and evaporated. Preparative HPLC purification, eluting with ethyl acetate/hexanes (35:65) gave 2.25 g (55%) of the title compound as a light yellow oil.

¹H-NMR (300 MHz, CDCl₃) δ 7.78 (m, 2H), 7.13–7.32 (m, 5H), 6.95 (m, 2H), 4.09 (m, 2H), 3.99 (s, 2H), 3.86 (s, 3H), 3.47 (m, 2H), 2.88 (m, 2H), 1.20 (t, 3H), 6.7.2 N-(2-Phenyl)ethyl-N-p-methoxybenzene-sulfonyl-glycine Hydroxamic acid Freshly prepared hydroxylamine reagent (12 mL; 12 mmol) was added to ethyl N-(2-phenyl)ethyl-N-p-methoxybenzenesulfonyl-glycinate (2.25 g; 5.5 mmol) and the resulting mixture stirred for 6 h at room temperature. The mixture was poured into 1 N HCl (100 mL) and extracted with CH₂Cl₂ (2×100 mL). The combined extracts were washed with saturated aqueous NaCl (1×100 mL), dried over MgSO₄, filtered, and evaporated under reduced pressure to give crude product. Trituration with diethyl ether afforded 1.50 g (75%) of the title compound as a white solid. ¹H-NMR (300 MHz, DMSO-d₆) δ 10.66 (s, 1H), 8.95 (br s, 1H), 7.75 (d, 2H), 7.10–7.30 (m, 5H), 7.08 (d, 2H), 3.84 (s, 3H), 3.74 (s, 2H), 3.30 (m, 2H), 2.76 (m, 2H).

6.8 Synthesis of N-(2-Phenyl)ethyl-N-p-methoxybenzenesulfonyl-G-aminobutyryl Hydroxamic Acid (FG 134)

6.8.1 N-(2-Phenyl)ethyl p-methoxybenzenesulfonamide

Phenethylamine (4.25 g; 35 mmol), p-methoxybenzene sulfonyl chloride (6.20 g; 30 mmol), and triethylamine (3.32 g; 32 mmol) were dissolved in CH₂Cl₂ (50 mL) and the resulting solution stirred 20 h at room temperature. The solution was washed with 0.5 N HCl (2×50 mL) and the aqueous layers back-extracted with additional CH₂Cl₂ (50 mL). The combined organic layers were dried over MgSO₄, filtered and evaporated to give 7.51 g (86%) of a thick, pale yellow oil.

¹H-NMR (CDCl₃): δ 2.77 (t, 2H), 3.20 (q, 2H), 3.88 (s, 3H), 4.60 (t, 1H), 6.96 (d, 2H), 7.05–7.30 (m, 5H), 7.75 (d, 2H).

6.8.2 Ethyl N-(2-Phenyl)Ethyl-N-p-methoxybenzenesulfonyl-γ-aminobutyrate

N-(2-Phenyl)ethyl p-methoxybenzenesulfonamide (2.95 g; 10 mmol) was dissolved in dry DMF (35 mL) and stirred under argon. Sodium hydride, 60% in mineral oil (0.55 g; 14 mmol), was added and the resulting mixture stirred at room temperature for 0.5 h. Ethyl 4-bromobutyrate (2.95 g; 15 mmol) and sodium iodide (250 mg) were added successively and the reaction heated to 90° C. for 6 h. After cooling to room temperature, the mixture was poured into diethyl ether (100 mL) and extracted with water (2×100 mL). The organic layer was dried over MgSO₄, filtered and evaporated to an oil. Preparative HPLC purification, eluting with a mixture of ethyl acetate/hexanes (35:65) gave 3.72 g (92%) of the title compound as an oil.

¹H-NMR (CDCl₃): δ 1.26 (t, 3H), 1.85 (m, 2H), 2.33 (t, 2H), 2.86 (m, 2H), 3.18 (m, 2H), 3.32 (m, 2H), 3.86 (s, 3H), 4.13 (m, 2H), 6.95 (m, 2H), 7.15–7.32 (m, 5H), 7.73 (m, 2H).

6.8.3 N-(2-Phenyl)ethyl-N-p-methoxy-benzenesulfonyl-γ-aminobutyryl Hydroxamic Acid Freshly prepared hydroxylamine reagent (20 mL; 20 mmol) was added to ethyl N-(2-phenyl)ethyl-N-p-methoxybenzene sulfonyl-β-alaninate (3.65 g; 9.1 mmol) and the resulting mixture stirred for 18 h at room temperature. The mixture was poured into 1 N HCl (100 mL) and extracted with CH₂Cl₂ (2×100 mL). The combined extracts were washed with saturated aqueous NaCl (1×100 mL), dried over MgSO₄, and evaporated under reduced pressure to give a crude gum. Trituration with diethyl ether afforded 2.54 g (71%) of the title compound as an oil.

¹H-NMR (DMSO-d₆): δ 1.68 (m, 2H), 1.96 (t, 2H) 2.77 (t, 2H), 3.11 (t, 2H), 3.29 (t, 2H), 3.83 (s, 3H), 7.26–7.08 (m, 7H), 7.72 (d, 2H), 8.69 (s, 1H), 10.23 (s, 1H).

6.9 Synthesis of N-4-Methoxyphenyl-N-4-methoxybenzenesulfonyl-glycine Hydroxamic Acid (FG 202)

6.9.1 Ethyl N-4-Methoxyphenyl-N-4-methoxybenzenesulfonyl-glycinate

N-4-Methoxyphenyl 4-methoxybenzenesulfonamide (1.46 g; 5.00 mmol) was dissolved in dry DMF (25 mL) and stirred under argon. Sodium hydride, 60% in mineral oil (224 mg; 7.0 mmol), was added and the mixture stirred at room temperature for 15 min. Ethyl bromoacetate (1.25 g; 7.5 mmol) and a catalytic amount of sodium iodide were added and the resulting mixture heated at 90° C. overnight. The reaction was poured into diethyl ether (50 mL) and washed with water (2×50 mL). The organic layer was dried over MgSO$_4$, filtered, and evaporated to an oil. Preparative HPLC purification, eluting with a mixture of ethyl acetate/hexanes (35:65), gave 1.75 g (92%) of the title compound as a pale yellow oil.

$^1$H-NMR (CDCl$_3$): δ 1.22 (t, 3H), 3.76 (s, 3H), 3.86 (s, 3H), 4.14 (q, 2H), 4.35 (s, 2H), 6.79 (d, 2H), 6.91 (d, 2H), 7.10 (d, 2H), 7.60 (d, 2H).

6.9.2 N-4-Methoxyphenyl-N-4-methoxybenzene-sulfonyl-glycine Hydroxamic Acid Freshly prepared hydroxylamine reagent (6 mL; 6 mmol) was added to ethyl N-4-methoxyphenyl-N-4-methoxybenzenesulfonyl-glycinate (673 mg; 1.77 mmol) and the resulting mixture stirred overnight at room temperature. The mixture was poured into 1 N HCl (40 mL) and extracted with CH$_2$Cl$_2$ (2×40 mL). The combined extracts were washed with saturated aqueous NaCl (40 mL), dried over MgSO$_4$, and evaporated under reduced pressure to give crude product. Trituration with diethyl ether afforded 405 mg (63%) of the title compound as a white solid.

$^1$H-NMR (DMSO-d$_6$): δ 3.72 (s, 3H), 3.84 (s, 3H), 4.06 (s, 2H), 6.84 (d, 2H), 7.01 (d, 2H), 7.07 (d, 2H), 7.53 (d, 2H), 8.86 (bs, 1H), 10.57 (s, 1H).

6.10 Synthesis of N-(4-Methoxyphenyl)ethyl-N-4-methoxybenzenesulfonyl-glycine Hydroxamic Acid (FG 204)

6.10.1 Ethyl N-(4-Methoxyphenyl)ethyl-N-4-methoxy-benzene Sulfonyl-glycinate N-(4-Methoxyphenyl)ethyl 4-methoxybenzenesulfonamide (1.50 g; 4.67 mmol) was dissolved in dry DMF (20 mL) and stirred under argon. Sodium hydride, 60% in mineral oil (224 mg; 5.6 mmol), was added and the resulting mixture stirred at room temperature for 15 min. Ethyl bromoacetate (780 mL; 7.00 mmol) was added and the reaction stirred at room temperature for 2 h. The mixture was poured into diethyl ether (50 mL) and the organic material washed with water, dried over Na$_2$SO$_4$, filtered, and evaporated to an oil. Preparative HPLC purification, eluting with a mixture of ethyl acetate/hexanes (35:65), gave 1.76 g (93%) of the title compound as a pale yellow oil.

$^1$H-NMR (CDCl$_3$): δ 1.20 (t, 3H), 2.81 (t, 2H), 3.43 (t, 2H), 3.78 (s, 3H), 3.85 (s, 3H), 3.98 (s, 2H), 4.08 (q, 2H), 6.81 (d, 2H), 6.94 (d, 2H), 7.06 (d, 2H), 7.76 (d, 2H).

6.10.2 N-(4-Methoxyphenyl)ethyl-N-4-methoxybenzene-sulfonyl-glycine Hydroxamic Acid Freshly prepared hydroxylamine reagent (6 mL; 6 mmol) was added to ethyl N-(4-methoxyphenyl)-ethyl-N-4-methoxybenzene sulfonyl-glycinate (758 mg; 1.86 mmol) and the resulting mixture stirred overnight at room temperature. The mixture was poured into 1 N HCl (40 mL) and extracted with CH$_2$Cl$_2$ (2×40 mL). The combined extracts were washed with saturated aqueous NaCl (40 mL), dried over MgSO$_4$, and evaporated under reduced pressure to give crude product. Trituration with diethyl ether afforded 327 mg (44%) of the title compound as a white solid.

$^1$H-NMR (DMSO-d$_6$): δ 2.69 (t, 2H), 3.25 (t, 2H), 3.71 (s, 3H), 3.73 (s, 2H), 3.83 (s, 3H), 6.81 (d, 2H), 7.07 (m, 4H), 7.74 (d, 2H), 8.94 (s, 1H), 10.63 (s, 1H).

6.11 Synthesis of N-Hydroxy-3-[(4-methoxyphenethyl)-(4-methoxybenzenesulfonyl)-amino]-propionamide (FG 206)

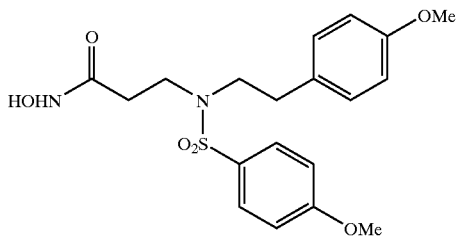

6.11.1 Ethyl 3-[(4-methoxyphenethyl)-(4-methoxybenzenesulfonyl)-amino]-propionate Ethyl acrylate (1.05 g; 10.0 mmol) and 2-(4-methoxyphenyl)ethylamine (1.52 g; 10.0 mmol) were dissolved in absolute ethanol (25 mL) and stirred overnight at room temperature. The solution was evaporated and crude ethyl 3-(4-methoxyphenethy-amino]-propionate (1.25 g; 5.0 mmol) was dissolved in CH$_2$Cl$_2$ (50 mL). 4-Methoxybenzenesulfonyl chloride (1.15 g; 5.5 mmol) and triethylamine (0.5 g; 5.0 mmol) were added and the mixture stirred overnight at room temperature. The reaction was washed with 1 N HCl (2×50 mL) and the aqueous layers back-extracted with CH$_2$Cl$_2$ (50 mL). The combined extracts were washed with saturated aqueous NaCl (100 mL), dried over MgSO$_4$, filtered, and evaporated to an oil. Preparative HPLC purification, eluting with a mixture of ethyl acetate/hexanes (35:65), gave 1.86 g (88%) of the title compound as a pale yellow oil. 300 MHz $^1$H-NMR (CDCl$_3$): δ 1.25 (t, 3H), 2.59 (t, 2H), 2.80 (m, 2H), 3.30 (m, 2H), 3.42 (t, 2H), 3.78 (s, 3H), 3.86 (s, 3H), 4.11 (q, 2H), 6.82 (d, 2H), 6.95 (d, 2H), 7.08 (d, 2H), 7.72 (d, 2H).

6.11.2 N-Hydroxy-3-[(4-methoxyphenethyl)-(4-methoxybenzenesulfonyl)-amino]-propionamide Freshly prepared hydroxylamine reagent (6 mL; 6 mmol) was added to ethyl 3-[(4-methoxyphenethyl)-(4-methoxybenzenesulfonyl)-amino]-propionate (587 mg; 1.40 mmol) and the resulting mixture stirred overnight at room temperature. The mixture was poured into 1 N HCl (40 mL) and extracted with CH$_2$Cl$_2$ (2×40 mL). The combined extracts were washed with saturated aqueous NaCl (40 mL), dried over MgSO$_4$, and evaporated under reduced pressure to give crude product. Trituration with diethyl ether afforded 408 mg (71%) of the title compound as a white solid. 300 MHz $^1$H-NMR (DMSO-d$_6$): δ 2.24 (t, 2H), 2.68 (t, 2H), 3.21 (t, 2H), 3.31 (m, 2H), 3.72 (s, 3H), 3.84 (s, 3H), 6.84 (d, 2H), 7.11 (d, 4H), 7.71 (d, 2H), 8.78 (s, 1H), 10.49 (s, 1H).

6.12 Synthesis of N-Hydroxy-3-[(4-methoxyphenethyl)-(n-butanesulfonyl)-amino]-propionamide (FG 207)

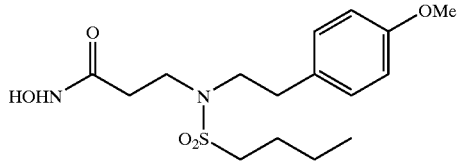

6.12.1 Ethyl 3-[(4-Methoxyphenethyl)-(n-butanesulfonyl)-amino]-propionate

Crude ethyl 3-(4-methoxyphenethyl-amino)-propionate (1.25 g; 5.0 mmol) was dissolved in $CH_2Cl_2$ (50 mL). Butanesulfonyl chloride (1.57 g; 10.0 mmol) and triethylamine (0.5 g; 5.0 mmol) were added and the mixture stirred overnight at room temperature. The reaction was washed with 1 N HCl (2×50 mL) and the aqueous layers back-extracted with $CH_2Cl_2$ (50 mL). The combined extracts were washed with saturated aqueous NaCl (100 mL), dried over $MgSO_4$, filtered, and evaporated to an oil. Preparative HPLC purification, eluting with a mixture of ethyl acetate/hexanes (35:65), gave 1.66 g (89%) of the title compound as a pale yellow oil. 300 MHz $^1$H-NMR ($CDCl_3$): δ 0.90 (t, 3H), 1.26 (t, 3H), 1.35 (m, 2H), 1.67 (m, 2H), 2.63 (t, 2H), 2.76 (m, 2H), 2.84 (t, 2H), 3.42 (t, 2H), 3.54 (t, 2H), 3.78 (s, 3H), 4.15 (q, 2H), 6.84 (d, 2H), 7.13 (d, 2H).

6.12.2 N-Hydroxy-3-[(4-methoxyphenethyl)-(n-butanesulfonyl)-amino]-propionamide Freshly prepared hydroxylamine reagent (8 mL; 8 mmol) was added to ethyl 3-[(4-methoxyphenethyl)-(n-butanesulfonyl)-amino]-propionate (935 mg; 2.52 mmol) and the resulting mixture stirred overnight at room temperature. The mixture was poured into 1 N HCl (40 mL) and extracted with $CH_2Cl_2$ (2×40 mL). The combined extracts were washed with saturated aqueous NaCl (40 mL), dried over $MgSO_4$, and evaporated under reduced pressure to give 545 mg (60%) as a gum which did not crystallize upon trituration with diethyl ether and hexanes. 300 MHz $^1$H-NMR (DMSO-$d_6$): δ 0.86 (t, 3H), 1.31, 2H), 1.54 (m, 2H), 2.28 (t, 2H), 2.76 (t, 2H), 2.96 (m, 2H), 3.32 (t, 2H), 3.42 (t, 2H), 3.72 (s, 3H), 6.86 (d, 2H), 7.16 (d, 2H), 8.79 (s, 1H), 10.52 (s, 1H).

6.13 Synthesis of N-Hydroxy-3-[(4-methoxyphenyl)-(4-methoxybenzenesulfonyl)-amino]-propionamide (FG 208)

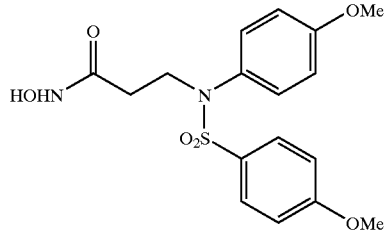

6.13.1 Ethyl 3-[(4-Methoxyphenyl)-(4-methoxybenzenesulfonyl)-amino]-propionate Ethyl acrylate (2.05 g; 20 mmol) and anisidine (2.46 g; 20 mmol) were added to a solution of concentrated HCl (1.5 mL) in absolute ethanol (20 mL) and the resulting mixture refluxed 48 h. The reaction was cooled to room temperature and then poured into 1 N NaOH (100 mL) and extracted with ethyl acetate (2×100 mL). The combined organic layers were washed with water (2×100 mL), dried over $MgSO_4$, filtered, and evaporated to give 3.15 g (70%) of a brown oil. A portion of the crude ethyl 3-(4-methoxyphenyl-amino) propionate (1.12 g; 5.0 mmol) was dissolved in $CH_2Cl_2$ (50 mL). 4-Methoxybenzene-sulfonyl chloride (1.15 g; 5.5 mmol) and triethylamine (0.5 g; 5.0 mmol) were added and the mixture stirred overnight at room temperature. The reaction was washed with 1 N HCl (2×50 mL) and the aqueous layers back-extracted with $CH_2Cl_2$ (50 mL). The combined extracts were washed with saturated aqueous NaCl (100 mL), dried over $MgSO_4$, filtered, and evaporated to an oil. Preparative HPLC purification, eluting with a mixture of ethyl acetate/hexanes (35:65), gave 1.42 g (72%) of the title compound as a pale brown oil. 300 MHz $^1$H-NMR ($CDCl_3$): δ 1.20 (t, 3H), 2.52 (t, 2H), 3.78 (t, 2H), 3.79 (s, 3H), 3.86 (s, 3H), 4.05 (q, 2H), 6.80 (m, 2H), 6.92 (m, 4H), 7.53 (m, 2H).

6.13.2 N-Hydroxy-3-[(4-methoxyphenyl)-(4-methoxybenzenesulfonyl)-amino]-propionamide Freshly prepared hydroxylamine reagent (6 mL; 6 mmol) was added to ethyl 3-[(4-methoxyphenyl)-(4-methoxybenzene-sulfonyl)-amino]-propionate (507 mg; 1.29 mmol) and the resulting mixture stirred overnight at room temperature. The mixture was poured into 1 N HCl (40 mL) and extracted with $CH_2Cl_2$ (2×40 mL). The combined extracts were washed with saturated aqueous NaCl (40 mL), dried over $MgSO_4$, and evaporated under reduced pressure to give 362 mg (74%) as a gum which did not crystallize upon trituration with diethyl ether and hexanes. 300 MHz $^1$H-NMR (DMSO-$d_6$): δ 2.24 (t, 2H), 3.67 (t, 2H), 3.75 (s, 3H), 3.84 (s, 3H), 6.90 (m, 4H), 7.09 (d, 2H), 7.47 (d, 2H), 8.73 (s, 1H), 10.35 (s, 1H).

6.14 Synthesis of N-Hydroxy-3-[(diphenylmethyl)-(4-methoxybenzenesulfonyl)-amino]-propionamide (FG 256)

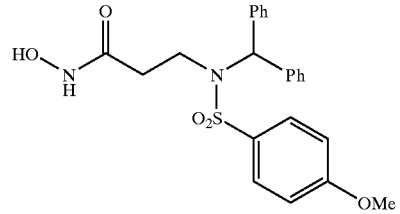

6.14.1 Ethyl 3-[(Diphenylmethyl)-(4-methoxybenzenesulfonyl)-amino]-propionate Ethyl acrylate (1.05 g; 10.0 mmol) and diphenylmethylamine (1.83 g; 10.0 mmol) were dissolved in absolute ethanol (25 mL) and stirred overnight at 70° C. The solution was evaporated and crude ethyl 3-(diphenylmethylamino) propionate (2.85 g; 10.0 mmol) was dissolved in DMF (50 mL). 4-Methoxybenzenesulfonyl chloride (2.30 g; 11.0 mmol) and pyridine (10 mL) were added and the mixture stirred overnight at 70° C. The dark reaction was washed with 1 N HCl (2×100 mL). The combined extracts were washed with saturated aqueous NaCl (100 mL), dried over $MgSO_4$, filtered, and evaporated to an oil. The black residue was eluted through a filter pad of silica gel using a hexanes/ ethyl acetate step gradient to remove polar material. Preparative HPLC purification, eluting with a mixture of ethyl acetate/hexanes (35:65), gave 1.06 g (23%) of the title compound as a pale yellow oil. 300 MHz $^1$H-NMR ($CDCl_3$): δ 1.16 (t, 3H), 2.12 (m, 2H), 3.57 (m, 2H), 3.84 (s, 3H), 3.99 (q, 2H), 6.48 (s, 1H), 6.83 (d, 2H), 7.04 (m, 4H), 7.24 (m, 6H), 7.64 (d, 2H).

6.14.2 N-Hydroxy-3-[(diphenylmethyl)-(4-methoxybenzenesulfonyl)-amino]-propionamide Freshly prepared hydroxylamine reagent (8 mL; 8 mmol) was added to ethyl 3-[(diphenylmethyl)-(4-methoxybenzene-sulfonyl)-amino]-propionate (563 mg; 1.24 mmol) and the resulting mixture stirred overnight at room temperature. The mixture was poured into 1 N HCl (100 mL) and extracted with CH$_2$Cl$_2$ (2×50 mL). The combined extracts were washed with saturated aqueous NaCl (100 mL), dried over MgSO$_4$, and evaporated under reduced pressure to give crude product. Trituration with diethyl ether afforded 262 mg (48%) of the title compound as a white solid. 300 MHz $^1$H-NMR (DMSO-d$_6$): δ 1.81 (m, 2H), 3.40(m, 2H), 3.84 (s, 3H), 6.31 (s, 1H), 7.02 (m, 6H), 7.28 (m, 6H), 7.71 (d, 2H), 8.59 (s, 1H), 10.23 (s, 1H).

6.15 Synthesis of N-Hydroxy-3-[(4-chlorobenzyl)-(4-methoxybenzenesulfonyl)-amino]-propionamide (FG 1237)

6.15.1 Ethyl 3-[(4-Chlorobenzyl)-(4-methoxybenzenesulfonyl)-amino]-propionate To a solution of β-alanine ethyl ester (154 mg, 1 mmol) in anhydrous methylene chloride (7 mL) at room temperature was added triethyl amine (101 mg, 1 mmol) and 4-chlorobenzaldehyde (155 mg, 1.1 mmol). After being stirred for 0.5 h, sodium triacetoxyborohydride (318 mg, 1.5 mmol) was added and the reaction mixture was stirred for additional 1 h at room temperature, followed by the addition of 4-methoxybenzenesulfonyl chloride (207 mg, 1 mmol) and triethyl amine (152 mg, 1.5 mmol). The resulting mixture was stirred for 18 h, quenched with 10% citric acid (10 mL) and, after 30 min, extracted with methylene chloride (2×30 mL). Two phases was separated and the organic layers was washed with brine, dried over MgSO$_4$, filtered, and concentrated. The crude product was purified by silica gel chromatography (2/1: hexanes/ethyl acetate) to give ethyl 3-[(4-chlorobenzyl)-(4-methoxybenzenesulfonyl)-amino]-propionate (44 mg, 0.1 mmol).

6.15.2 N-Hydroxy-3-[(4-chlorobenzyl)-(4-methoxybenzenesulfonyl)-amino]-propionamide (FG 1237)

Freshly prepared NH$_2$OH solution (1 M in methanol) (0.2 mL, 0.2 mmol) was added to ethyl 3-[(4-chlorobenzyl)-(4-methoxybenzenesulfonyl)-amino]-propionate (44 mg, 0.1 mmol). After being stirred at room temperature for 18 h, the reaction mixture was concentrated. The crude product was triturated in ether and the residue was lyophilized from water to give N-hydroxy-3-[(4-chlorobenzyl)-(4-methoxybenzene-sulfonyl)-amino]-propionamide (30 mg, 0.08 mmol) as a light yellow solid. $^1$H-NMR (360 MHz, DMSO-d$_6$) δ 7.75 (d, J=8.8 Hz, 2H), 7.39 (d, J=8.5 Hz, 2H), 7.32 (d, J=8.4 Hz, 2H), 7.11 (d, J=8.8 Hz, 2H), 4.28 (s, 2H), 3.85 (s, 3H), 3.20 (br t, J=7.8 Hz, 2H), 1.86 (t, J=8.1 Hz, 2H).

6.16 Synthesis of N-Hydroxy-3-[(4-methoxyphenethyl)-(3-aminobenzenesulfonyl)-amino]-propionamide (FG 1492)

6.16.1 Methyl 3-[(4-Methoxyphenethyl)-(3-nitrobenzenesulfonyl)-amino]-propionate A mixture of methyl acrylate (6.0 g, 69.7 mmol) and p-methoxyphenethyl amine (10.5 g, 69.7 mmol) in anhydrous methanol (88 mL) was refluxed for 3 days and then was concentrated to give methyl 3-[(4-methoxyphenethyl)amino]-propionate (16.2 g). To a solution of methyl 3-[(4-methoxyphenethyl)amino]-propionate (3.0 g, 12.6 mmol) in anhydrous methylene chloride (35 mL) was added 3-nitrobenzenesulfonyl chloride (2.8 g, 12.6 mmol), followed by triethylamine (2.6 g, 25.3 mmol). After stirring for 18 h at room temperature, the mixture was quenched with 1 N HCl solution (150 mL) and extracted with methylene chloride (100 mL). Combined organic layers was washed successively with 1 N HCl solution (100 mL) and brine, dried over MgSO$_4$, filtered, and concentrated. The crude product was purified by silica gel flash chromatography (2.5/1 to 2/1: hexanes/EtOAc) to provide methyl 3-[(4-methoxyphenethyl)-(4-cyanobenzenesulfonyl)-amino]-propionate (3.28 g, 7.8 mmol).

6.16.2 Methyl 3-[(4-Methoxyphenethyl)-(3-aminobenzenesulfonyl)-amino]-propionate To a clear solution of methyl 3-[(4-methoxyphenethyl)-(3-nitrobenzenesulfonyl)-amino]-propionate in 5/1 methanol/ethyl acetate (30 mL) was added 10% Pd/C (300 mg) and ammonium formate (1.79 g, 28.4 mmol). After being stirred at room temperature for 24 h, the catalyst was filtered off through a pad of celite and the filtrate was concentrated. The residue was partitioned between methylene chloride (100 mL) and water (100 mL). Aqueous layer was extracted with another 100 mL of methylene chloride. Combined organic layer was washed with water (100 mL) and brine, dried over Na$_2$SO$_4$, filtered, and concentrated to give methyl 3-[(4-methoxyphenethyl)-(3-aminobenzenesulfonyl)-amino]-propionate (2.8 g, 7.1 mmol) as a yellow gummy product.

6.16.3 N-Hydroxy-3-[(4-methoxyphenethyl)-(3-aminobenzenesulfonyl)-amino]-propionamide (FG 1492)

Freshly prepared NH$_2$OH solution (1 M in MeOH) (0.6 mL, 0.6 mmol)) was added to methyl 3-[(4-methoxyphenethyl)-(3-aminobenzenesulfonyl)amino] propionate (110 mg, 0.28 mmol). After stirring at room temperature for 18 h, the reaction mixture was concentrated and taken up with 10 mL of water. The mixture was acidified to pH 3–4 by 1 N HCl solution and extracted with ethyl acetate (2×20 mL). Combined organic layers was washed with brine, dried over MgSO$_4$, filtered and concentrated. The crude product was purified by silica gel chromatography (10/1 methylene chloride/methanol) to give N-hydroxy-3-[(4-methoxyphenethyl)-(3-aminobenzene-sulfonyl)amino]-propionamide (33 mg, 0.08 mmol). NMR (360 MHz, DMSO-d6) δ 10.44 (s, 1H), 8.72 (br s, 1H), 7.23–6.25 (m, 8H), 5.57 (br s, 2H), 3.70 (s, 3H), 3.33 (t, 2H), 3.24 (t, 2H), 2.65 (t, 2H), 2.24 (t, 2H).

6.17 Synthesis of N-Hydroxy-3-[(4-methoxyphenethyl)-(4-(tetrazol-5yl) benzenesulfonyl)-amino]-propionamide (FG 1496)

6.17.1 Methyl 3-[(4-Methoxyphenethyl)-(4-cyanobenzene-sulfonyl)-amino]-propionate A mixture of methyl acrylate (6.0 g, 69.7 mmol) and p-methoxyphenethyl amine (10.5 g, 69.7 mmol) in anhydrous methanol (88 mL) was refluxed for 3 days and then was concentrated to give methyl 3-[(4-methoxyphenethyl) amino]-propionate (16.2 g).

To a solution of methyl 3-[(4-methoxy-phenethyl)amino]-propionate (3.0 g, 12.6 mmol) in anhydrous methylene chloride (35 mL) was added 4-cyanobenzenesulfonyl chloride (2.6 g, 12.6 mmol), followed by triethylamine (2.6 g, 25.3 mmol). After stirring for 18 h at room temperature, the mixture was quenched with 1 N HCl solution (150 mL) and extracted with methylene chloride (2×100 mL). Combined organic layers was washed successively with 1 N HCl solution (100 mL) and brine, dried over MgSO$_4$, filtered, and concentrated. The crude product was purified by silica gel flash chromatography (2/1: hexanes/EtOAc) to provide methyl 3-[(4-methoxyphenethyl)-(4-cyanobenzenesulfonyl)-amino]-propionate (3.14 g, 7.8 mmol).

6.17.2 Methyl 3-[(4-Methoxyphenethyl)-(4-(tetrazol-5yl)-benzenesulfonyl)-amino]-propionate A suspension of methyl 3-[(4-methoxyphenethyl)-(4-cyanobenzenesulfonyl)-amino]-propionate (220 mg, 0.55 mmol), sodium azide (43 mg, 0.66 mmol), and triethylamine hydrochloride (91 mg, 0.66 mmol) in anhydrous ethylene glycol dimethyl ether (3 mL) was fluxed for 48 h. Reaction mixture was concentrated, resuspended in water (10 mL) and extracted with ethyl acetate (2×20 mL). The organic layer was washed with 0.5 N HCl solution and brine, dried over $MgSO_4$. After filtration, the filtrate was concentrated to give methyl 3-[(4-methoxyphenethyl)-(4-(tetrazol-5yl)benzenesulfonyl)-amino]-propionate (112 mg, 0.25 mmol).

6.18 Synthesis of N-Hydroxy-3-[(4-methoxyphenethyl)-(4-(tetrazol-5yl)benzenesulfonyl)-amino]-propionamide (FG 1496)

Freshly prepared $NH_2OH$ solution (1 M in MeOH) (1.5 mL) was added to methyl 3-[(4-methoxyphenethyl)-(4-(tetrazol-5yl)-benzenesulfonyl)-amino]-propionate (112 mg, 0.25 mmol). After stirring at room temperature for 18 h, the reaction mixture was partitioned between 1 N HCl solution (20 mL) and ethyl acetate (30 mL). Two phases were separated and the aqueous layer was extracted with another 30 mL of ethyl acetate. Combined organic layers were washed with brine, dried over $MgSO_4$, filtered and concentrated to give N-hydroxy-3-[(4-methoxyphenethyl)-(4-(tetrazol-5yl)benzene-sulfonyl)amino]-propionamide (52 mg, 0.12 mmol). NMR (360 MHz, DMSO-d6) δ 10.46 (s, 1H), 8.74 (br s, 1H), 8.22 (d, J=8.4 Hz, 2H), 7.99 (d, J=8.7 Hz, 2H), 7.10 (d, J=8.2 Hz, 2H), 6.81 (d, J=8.2 Hz, 2H), 3.69 (s, 3H), 3.42 (t, J=7.5 Hz, 2H), 3.31 (t, J=7.9 Hz, 2H), 2.70 (t, J=7.6 Hz, 2H), 2.25 (t, J=7.5 Hz, 2H).

6.19 N-Hydroxy—N',N'-disubstituted-propionamides

N-Hydroxy—N',N'-disubstituted-propionamides in examples 6.24.1 thru 6.24.37 were prepared according to general reaction schemes I, II, and III. More specifically, the following steps were executed:

Step 1: Methyl acrylate or ethyl acrylate is added to a solution of a primary amine in ethanol (1.3 mL/mmol). The mixture is heated to reflux (ca. 90° C.) for 20 h and then concentrated.

Step 2: The residue of step 1 is dissolved in methylene chloride (2.8 mL/mmol), followed by the addition of sulfonyl chloride (1 eq.) and Amberlyst (A-21) weakly basic ion exchange resin (0.8 g/mmol). The mixture is vortexed overnight at room temperature (ca. 18 h), monitored by TLC by observing the disappearance of sulfonyl chloride. The reaction mixture is filtered and concentrated.

Step 3: To the residue of Step 2 is added 2 equivalents of freshly prepared neutralized $NH_2OH$ (1 M in methanol). The mixture is vortexed overnight (monitored by TLC), concentrated, followed by work up procedure and/or chromatographic purification to afford N-hydroxy-N',N'-disubstituted-propionamides. Two work up procedures are set up depending upon the feature of the product.

Step 4:

Work up procedure A: (For hydroxamates 6.24.1–6.24.27): The residue of step 3 is treated with 1 N HCl solution and extracted with ethyl acetate. The organic layer is dried over $MgSO_4$, filtered, and concentrated. The residue is then triturated with ether to remove undesired products which are discarded. The solid is collected and dried in vacco.

Work up procedure B: (For hydrophilic hydroxamates 6.24.28 to 5.24.33): The residue of step 3 is triturated with ethyl acetate twice. Ethyl acetate is decanted and discarded. The residue is treated with water, neutralized by 1 N HCl solution to pH=7–8, and extracted with 10/1 ethyl acetate/methanol. The combined organic layers is washed with brine, dried over magnesium sulfate, filtered, and concentrated. The residue is triturated in ether, which is discarded, and dried in vacco to furnish the product as a white solid.

In the case that solid product formed during work up process, the solid is collected, washed with ethyl acetate and dried in vacco.

In the case that TLC indicates low purity of the desired product, purification will be conducted using silica gel chromatography and/or recrystallization.

Preparation of neutralized $NH_2OH$ solution (1 M) in methanol: A warm and clear solution of hydroxylamine hydrochloride in methanol (2 mM/mL) (it becomes clear upon heating) is added to another warm and clear solution of potassium hydroxide in methanol (3 mM/mL) (it also becomes clear upon heating). White precipitate of potassium chloride forms immediately. The mixture is cooled in an ice bath for 30 min. and filtered. The fresh filtrate (1 M) is used for the hydroxamation reaction.

Preparation of 4-(3-Substituted-ureido)benzenesulfonyl chloride: To a solution of primary or secondary amine (0.5 mmol) in THF (1 mL) at 0° C. was added 4-(chlorosulfonyl) phenyl isocyanate (0.5 mmol). After stirring at 0° C. for 2 h, the mixture was concentrated to afford 4-(3-substituted-ureido)benzenesulfonyl chloride. This material was then used in Step B as described above.

6.19.1 Synthesis of N-Hydroxy-3-[(adamantan-2-yl)-(4-methoxybenzenesulfonyl)-amino]-propionamide (FG 1335)

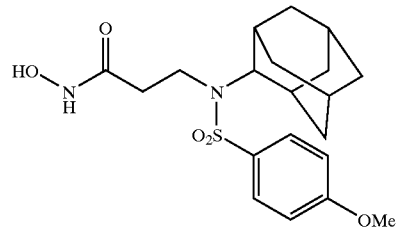

NMR (360 MHz, DMSO-d6) δ 10.46 (s, 1H), 8.68 (s, 1H), 7.70 (d, J=8.8 Hz, 2H), 7.09 (d, J=9.0 Hz, 2H), 3.83 (s, 3H), 3.47 (m, 2H), 2.34 (m, 2H), 2.15–1.40 (m, 16H).

6.19.2 Synthesis of N-Hydroxy-3-[(morpholin-4-yl-ethyl)-(4-methoxybenzenesulfonyl)-amino]-propionamide (FG 1131)

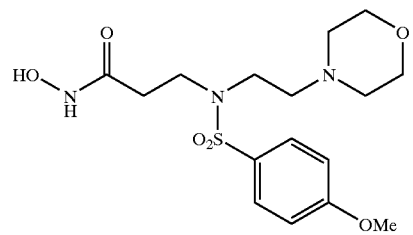

NMR (360 MHz, DMSO-d6) δ 10.43 (s, 1H), 8.71 (s, 1H), 7.73 (d, J=9.2 Hz, 2H), 7.10 (d, J=9.2 Hz, 2H), 3.83 (s, 3H), 3.52 (t, J=4.7 Hz, 4H), 3.28 (m, 2H), 3.16 (t, J=7.8 Hz, 2H), 2.40–2.33 (m, 6H), 2.25 (t, J=7.7 Hz, 2H), 6.19.3 Synthesis of N-Hydroxy-3-[(pyridin-2-yl-ethyl)-(4-methoxybenzenesulfonyl)-amino]-propionamide (FG 1132)

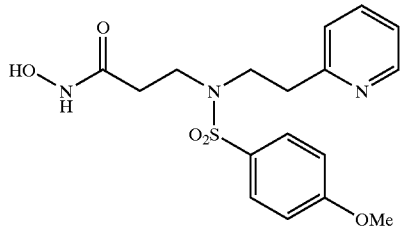

NMR (360 MHz, DMSO-d6) δ 10.45 (s, 1H), 8.74 (s, 1H), 8.46 (d, J=4.8 Hz, 1H), 7.68 (m, 3H), 7.22 (m, 2H), 7.09 (d, J=8.9 Hz, 2H), 3.82 (s, 3H), 3.41 (t, J=7.8 Hz, 2H), 3.31 (t, J=7.6 Hz, 2H), 2.91 (t, J=7.7 Hz, 2H), 2.22 (t, J=7.4 Hz, 2H).

6.19.4 Synthesis of N-Hydroxy-3-[(phenethyl)-(4-nitrobenzenesulfonyl)-amino]-propionamide (FG 1268)

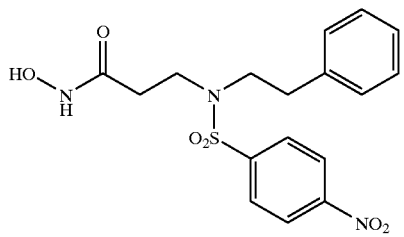

NMR (360 MHz, DMSO-d6) δ 10.45 (s, 1H), 8.75 (s, 1H), 8.35 (d, J=8.7 Hz, 1H), 8.03 (d, J=8.8 Hz, 1H), 7.26–7.18 (m, 5H), 3.43 (t, J=7.2 Hz, 2H), 3.36 (t, J=7.9 Hz, 2H), 2.78 9(t, J=7.9 Hz, 2H), 2.23 (t, J=7.2 Hz, 2H).

6.19.5 Synthesis of N-Hydroxy-3-[(phenethyl)-(thiophen-2yl-sulfonyl)-amino]-propionamide (FG 1270)

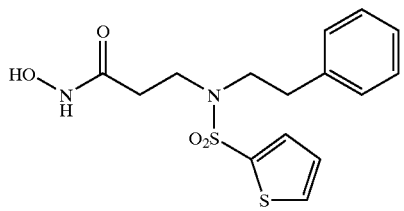

NMR (360 MHz, DMSO-d6) δ 10.46 (s, 1H), 8.74 (s, 1H), 7.97 (d, J=4.8 Hz, 1H), 7.66 (d, J=3.7 Hz, 1H), 7.30–7.20 (m, 6H), 3.36 (t, J=7.4 Hz, 2H), 3.29 (m, 2H), 2.77 (t, J=7.8 Hz, 2H), 2.26 (t, J=7.4 Hz, 2H).

6.19.6 Synthesis of N-Hydroxy-3-[(4-methoxy-phenethyl)-(4-methylsulfonyl-benzene-sulfonyl)-amino]-propionamide (FG 1460)

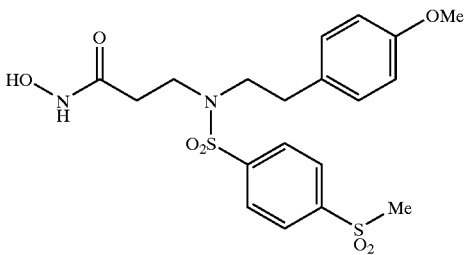

NMR (360 MHz, DMSO-$d_6$) δ 8.09 (d, J=8.1 Hz, 2H), 8.00 (d, J=8.5 Hz, 2H), 7.10 (d, J=8.3 Hz, 2H), 6.81 (d, J=8.5 Hz, 2H), 3.70 (s, 3H), 3.37 (t, J=7.4 Hz, 2H), 3.29 (m, 2H), 2.71 (t, J=7.9 Hz, 2H), 2.10 (t, J=7.5 Hz, 2H).

6.19.7 Synthesis of N-Hydroxy-3-[(3,4-methylenedioxybenzyl)-(4-methoxy-benzenesulfonyl)-amino]-propionamide (FG 1273)

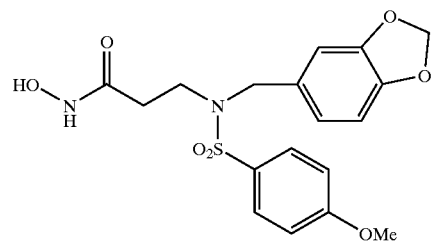

NMR (360 MHz, DMSO-d6) δ 10.34 (s, 1H), 8.65 (s, 1H), 7.75 (d, J=8.7 Hz, 2H), 7.11 (d, J=8.8 Hz, 2H), 6.84 (d, J=7.8 Hz, 1H), 6.76 (s, s, 1H), 6.75 (d, J=7.8 Hz, 1H), 5.99 (s, 2H), 4.17 (s, 2H), 3.84 (s, 3H), 3.21 (m, 2H), 2.04 (m, 2H).

6.19.8 Synthesis of N-Hydroxy-3[(4-chloro-phenethyl)-(4-methoxybenzenesulfonyl)-amino)-propionamide (FG 1300)

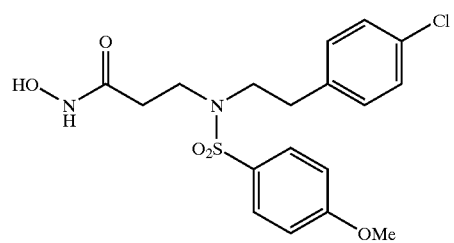

NMR (360 MHz, DMSO-d6) δ 10.43 (s, 1H), 8.74 (s, 1H), 7.69 (d, J=8.7 Hz, 2H), 7.31 (d, J=8.7 Hz, 2H), 7.20 (d, J=8.4 Hz, 2H), 7.08 (d, J=8.6 Hz, 2H), 3.83 (s, 3H), 3.25 (m, 4H), 2.73 (t, J=7.6 Hz, 2H), 2.21 (t, J=7.3 Hz, 2H).

6.19.9 Synthesis of N-Hydroxy-3[(cyclohexyl-ethyl)-(4-methoxy-benzenesulfonyl)-amino]-propionamide (FG 1306)

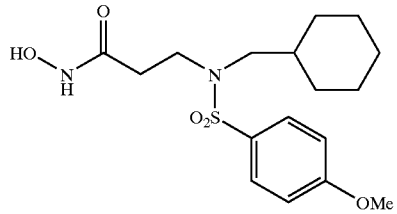

NMR (360 MHz, DMSO-d6) δ 10.42 (s, 1H), 8.69 (s, 1H), 7.70 (d, J=8.9 Hz, 2H), 7.10 (d, J=8.7 Hz, 2H), 3.83 (s, 3H), 3.20 (t, J=7.8 Hz, 2H), 2.82 (d, J=7.4 Hz, 2H), 2.18 (t, J=7.8 Hz, 2H), 1.62 (m, 6H), 1.15 (m, 3H), 0.82 (m, 2H).

6.19.10 Synthesis of N-Hydroxy-3-[benzodioxan-2-yl-methyl)-(4-methoxybenzene)-sulfonyl)-amino]-propionamide (FG 1374)

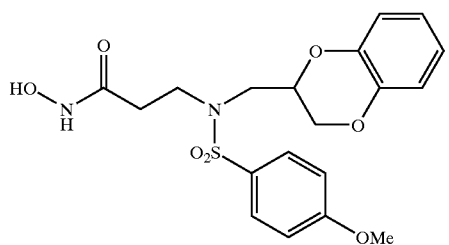

NMR (360 MHz, DMSO-d6) δ 10.42 (s, 1H), 8.70 (s, 1H), 7.76 (d, J=8.7 Hz, 2H), 7.11 (d, J=9.2 Hz, 2H), 6.81 (m, 4H), 4.36–4.27 (m, 2H), 3.96 (m, 1H), 3.84 (s, 3H), 3.37 (m, 4H), 2.52 (m, 1H), 2.30 (m, 1H).

6.19.11 Synthesis of N-Hydroxy-3-[(3,4-methylenedioxybenzyl)-(thiophene-2-sulfonyl)-amino]-propionamide (FG 1371)

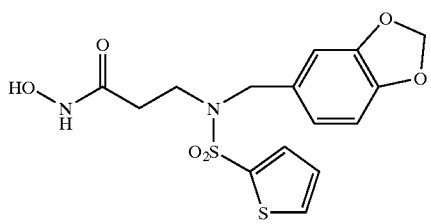

NMR (360 MHz, DMSO-d6) δ 10.37 (s, 1H), 8.68 (s, 1H), 8.00 (d, J=4.8 Hz, 1H), 7.69 (d, J=3.7 Hz, 1H), 7.23 (dd, J=4.8, 3.9 Hz, 1H), 6.87–6.76 (m, 3H), 6.00 (s, 2H), 4.26 (s, 2H), 3.28 (m, 2H), 2.09 (t, J=8.0 Hz, 2H).

6.19.12 Synthesis of N-Hydroxy-3-[(3,4-methylenedioxybenzyl)-(5-benzene-sulfonylthiophene-2-sulfonyl)-amino]-propionamide (FG 1361)

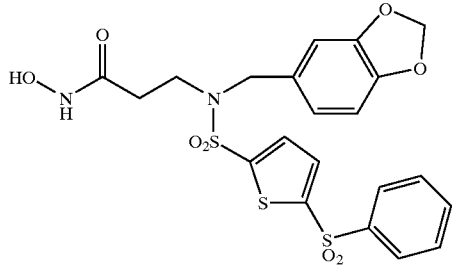

NMR (360 MHz, DMSO-d6) δ 10.39 (s, 1H), 8.70 (s, 1H), 8.06–7.66 (m, 7H), 6.79–6.70 (m, 3H), 5.99 (s, 2H), 4.29 (s, 2H), 3.36 (t, J=7.7 Hz, 2H), 2.11 (t, J=7.6 Hz, 2H).

6.19.13 Synthesis of N-Hydroxy-3[(3,4-methylenedioxybenzyl)-(4-n-butoxybenzenesulfonyl)-amino]-propionamide (FG 1372)

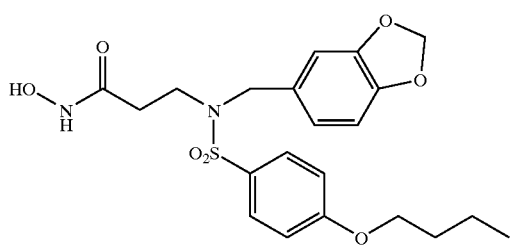

NMR (360 MHz, DMSO-d6) δ 10.33 (s, 1H), 8.64 (s, 1H), 7.73 (d, J=8.5 Hz, 2H), 7.10 (d, J=8.7 Hz, 2H)m 6.85–6.74 (m, 3H), 5.99 (s, 2H), 3.24 (m, 2H), 2.04 (t, J=7.6 Hz, 2H), 1.94 (m, 2H), 1.76 (m, 2H), 1.44 (m, 2H), 0.93 (t, J=7.4 Hz, 3H).

6.19.14 Synthesis of N-Hydroxy-3-[(3,4-methylenedioxybenzyl)-(octanesulfonyl)-amino]-propionamide (FG 1359)

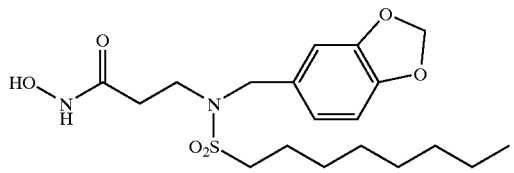

NMR (360 MHz, DMSO-d6) δ 10.43 (s, 1H), 8.70 (s, 1H), 6.96–6.80 (m, 3H), 6.00 (s, 2H), 4.25 (s, 2H), 3.27 (m, 2H), 3.06 (t, J=7.9 Hz, 2H), 2.16 (t, J=7.5 Hz, 2H), 1.62 (m, 2H), 1.34–1.25 (m, 10H), 0.85 (t, J=6.9 Hz).

6.19.15 Synthesis of N-Hydroxy-3-[(3,4-methylenedioxybenzyl)-(5-bromothiophene-2-sulfonyl)-amino]-propionamide (FG 1367)

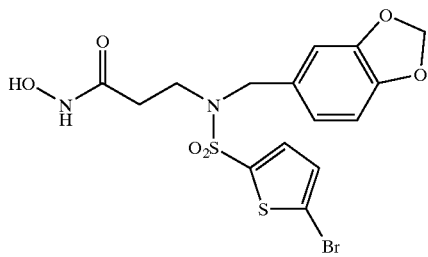

NMR (360 MHz, DMSO-d6) δ 10.38 (s, 1H), 8.68 (s, 1H), 7.54 (d, J=3.9 Hz, 1H), 7.40 (d, J=3.6 Hz, 1H), 6.80 (m, 3H), 6.00 (s, 2H), 4.24 (s, 2H), 3.31 (t, J=7.6 Hz, 2H), 2.10 (t, J=7.8 Hz, 2H).

6.19.16 Synthesis of N-Hydroxy-3-[(3,4-methylenedioxybenzyl)-(4-acetylamino-benzenesulfonyl)-amino]-propionamide (FG 1357)

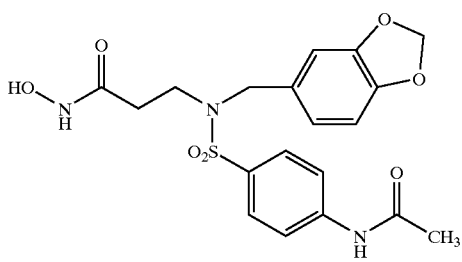

NMR (360 MHz, DMSO-d6) δ 10.34 (s, 1H), 7.78 (d, J=8.7 Hz, 2H), 7.74 (d, J=8.6 Hz, 2H), 6.85–6.78 (m, 3H), 5.99 (s, 2H), 4.19 (s, 2H), 3.23 (m, 2H), 2.08 (s, 3H), 2.07 (m, 2H).

6.19.17 Synthesis of N-Hydroxy-3-[(3,4-methylenedioxybenzyl)-(3,4-dimethoxybenzene-sulfonyl)-amino]-propionamide (FG 1410)

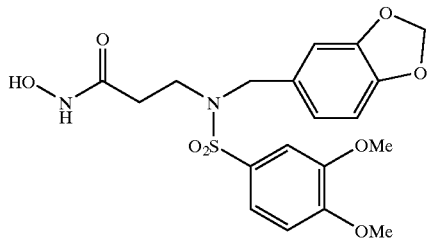

NMR (360 MHZ, DMSO-d6) δ 7.39 (dd, J=8.4, 2.2 Hz, 1H), 7.23 (d, J=2.3 Hz, 1H), 7.12 (d, J=8.3 Hz, 1H), 6.84 (m, 3H), 5.99 (s, 2H), 4.21 (s, 2H), 3.84 (s, 3H), 3.82 (s, 3H), 3.21 (t, J=8.0 Hz, 2H), 1.90 (t, J=8.1 Hz, 2H).

6.19.18 Synthesis of N-Hydroxy-3-[(3,4-methylenedioxybenzyl)-(benzo-2,1,3-thiadiazole-4-sulfonyl)-amino]-propionamide (FG 1362)

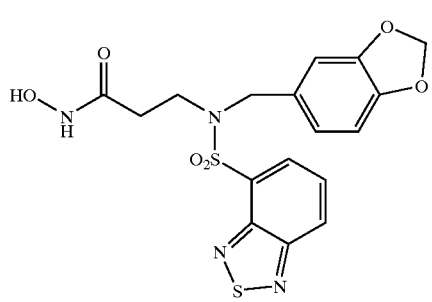

NMR (360 MHz, DMSO-d6) δ 10.27 (s, 1H), 8.58 (s, 1H), 8.38 (d, J=8.7 Hz, 1H), 8.22 (d, J=7.0 Hz, 1H), 7.84 (dd, J=8.6, 7.2 Hz, 1H), 6.77–6.67 (m, 3H), 5.96 (s, 2H), 4.48 (s, 2H), 3.52 (t, J=7.8 Hz, 2H), 2.02 (t, J=7.5 Hz, 2H).

6.19.19 Synthesis of N-Hydroxy-3-[(3,4-methylenedioxybenzyl)-(4-methylsulfonylbenzenesulfonyl)-amino]-propionamide (FG 1464)

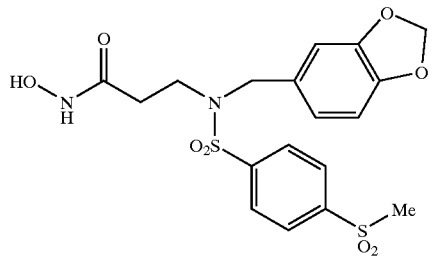

NMR (360 MHz, DMSO-d6) δ 8.12 (d, J=8.4 Hz, 2H), 8.06 (d, J=8.7 Hz, 2H), 6.85–6.75 (m, 3H), 5.99 (s, 2H), 4.29 (s, 2H), 3.29 (m, 2H), 2.49 (s, 3H), 1.93 (t, J=7.7 Hz, 2H).

6.19.20 Synthesis of N-Hydroxy-3-[(2-thiophenethyl)-(phenylmethylsulfonyl)-amino]-propionamide (FG 1414)

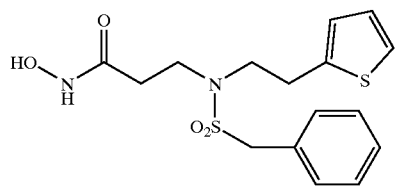

NMR (360 MHz, DMSO-d6) δ 10.46 (s, 1H), 8.74 (s, 1H), 7.38–7.31 (m, 6H), 6.94 (dd, J=5.1, 3.4 Hz, 1H), 6.87 (d, J=3.4 Hz, 1H), 4.37 (s, 2H), 3.33 (t, J=7.3 Hz, 2H), 3.25 (m, 2H), 2.94 (t, J=7.8 Hz, 2H), 2.23 (t, J=7.3 Hz, 2H).

6.19.21 Synthesis of N-Hydroxy-3-[(2-thiophenethyl)-(4-n-butoxy-benzenesulfonyl)-amino]-propionamide (FG1416)

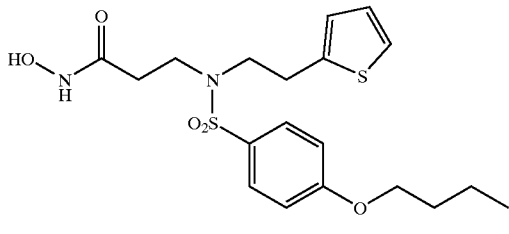

NMR (360 MHz, DMSO-d6) δ 10.43 (s, 1H), 8.72 (s, 1H), 7.69 (d, J=8.9 Hz, 2H), 7.32 (d, J=5.2 Hz, 1H), 7.09 (d, J=8.7 Hz, 2H), 6.94 (dd, J=5.2, 3.2 Hz, 1H), 6.87 (d, J=2.4 Hz, 1H), 4.05 (t, J=6.4 Hz, 2H), 3.28 (m, 2H), 2.97 (t, J=7.5 Hz, 2H), 2.22 (t, J=7.4 Hz, 2H), 1.70 (m, 2H), 1.42 (m, 2H), 0.92 (t, J=7.3 Hz, 3H).

6.19.22 Synthesis of N-Hydroxy-3-[(thiophen-2yl-ethyl)-(5-bromothiophen-2-sulfonyl)-amino]-propionamide (FG 1417)

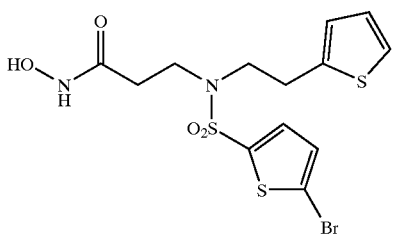

NMR (360 MHz, DMSO-d6) δ 10.46 (s, 1H), 8.74 (s, 1H), 7.53 (d, J=4.1 Hz, 1H), 7.38 (d, J=4.1 Hz, 1H), 7.34 (d, J=5.4 Hz, 1H), 6.95 (dd, J=5.0, 3.4 Hz, 1H), 6.90 (d, J=3.0 Hz, 1H), 3.37 (m, 4H), 3.03 (t, J=7.8 Hz, 2H), 2.26 (t, J=7.4 Hz, 2H).

6.19.23 Synthesis of N-Hydroxy-3-[(2-thiophenethyl)-(2-thiophenesulfonyl)-amino]-propionamide (FG 5 1425)

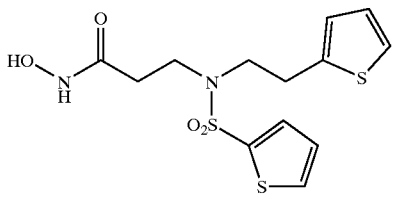

NMR (360 MHz, DMSO-d6) δ 10.46 (s, 1H), 8.74 (s, 1H), 7.98 (dd, J=4.8, 1.3 Hz, 1H), 7.67 (dd, J=3.7, 1.3 Hz, 1H), 7.34 (dd, J=5.1, 1.0 Hz, 1H), 7.23 (dd, J=5.0, 4.0 Hz, 1H), 6.95 (dd, J=5.1, 3.2 Hz, 1H), 6.89 (d, J=2.3 Hz, 1H), 3.35 (m, 4H), 3.02 (t, J=7.7 Hz, 2H), 2.26 (t, J=7.3 Hz, 2H).

6.19.24 Synthesis of N-Hydroxy-3-[(2-thiophenethyl)-(5-benzene-sulfonylthiophene-2-sulfonyl)-amino]-propionamide (FG 1419)

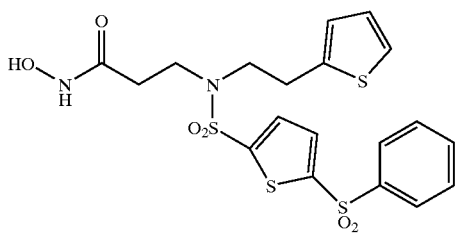

NMR (360 MHz, DMSO-d6) δ 8.04 (d, J=7.5 Hz, 2H), 7.89 (d, J=4.1 Hz, 1H), 7.76–7.65 (m, 4H), 7.28 (d, J=5.1 Hz, 1H), 6.88 (dd, J=4.8, 3.4 Hz, 1H), 6.84 (d, J=3.1 Hz, 1H), 3.37 (m, 4H), 3.00 (t, J=7.6 Hz, 2H), 2.11 (t, J=7.4 Hz, 2H).

6.19.25 Synthesis of N-Hydroxy-3-[(2-thiophenetyl)-(4-acetylamino-benzenesulfonyl)-amino]-propionamide (FG 1411).

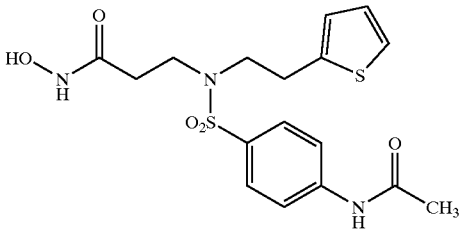

NMR (360 MHz, DMSO-d6) δ 10.44 (s, 1H), 10.31 (s, 1H), 8.73 (s, 1H), 7.77 (d, J=8.8 Hz, 2H), 7.71 (d, J=8.9 Hz, 2H), 7.33 (d, J=5.1 Hz, 1H), 6.94 (dd, J=4.9, 3.4 Hz, 1H), 6.88 (d, J=3.0 Hz, 1H), 3.29 (m, 4H), 2.97 (t, J=7.7 Hz, 2H), 2.21 (t, J=7.3 Hz, 2H), 2.07 (s, 3H).

6.19.26 Synthesis of N-Hydroxy-3-[(2-thiophenethyl)-(4-methylsulfonyl-benzenesulfonyl)-amino]-propionamide (FG 1463)

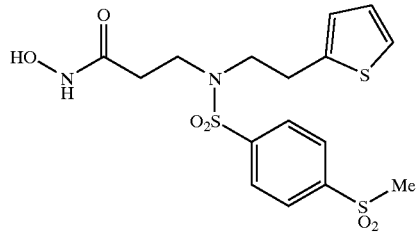

NMR (360 MHz, DMSO-d6) δ 8.11 (d, J=8.6 Hz, 2H), 8.02 (d, J=8.6 Hz, 2H), 7.32 (d, J=5.1 Hz, 1H), 6.94–6.88 (m, 2H), 3.37 (m, 4H), 3.29 (t, J=7.4 Hz, 2H), 2.10 (t, J=7.7 Hz, 2H).

6.19.27 Synthesis of N-Hydroxy-3-[(2-methoxy-phenethyl)-(4-carboxy-benzenesulfonyl)-amino]-propionamide (FG 1405)

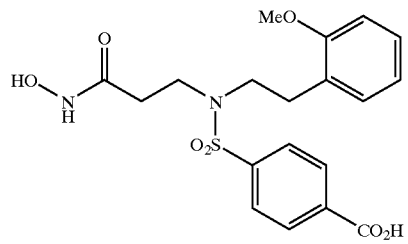

NMR (360 MHz, DMSO-d6, room temp.) δ 10.50 (s, 1H), 8.75 (s, 1H), 7.79–6.72 (m, 8H), 3.76 (s, 3H), 3.66 (br t, J=6.8 Hz, 1H), 3.38 (m, 1H), 3.25 (m, 2H), 2.67 (m, 2H), 2.34 (br t, J=6.8 Hz, 1H), 2.28 (br t, J=7.1 Hz, 1H).

6.19.28 Synthesis of N-Hydroxy-3-[(3,4-methylenedioxybenzyl)-(4-(N'-hydroxyamidino)benzenesulfonyl)-amino]-propionamide (FG 1369)

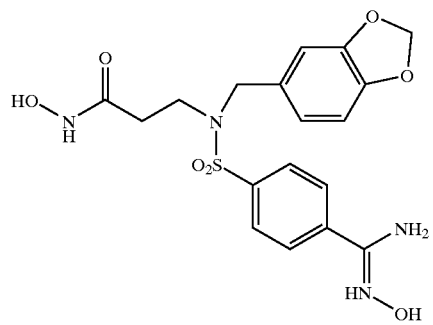

NMR (360 MHz, DMSO-d6) δ 10.36 (s, 1H), 9.94 (s, 1H), 8.66 (s, 1H), 7.89 (d, J=8.2 Hz, 2H), 7.81 (d, J=8.4 Hz, 2H), 6.85 (d, J=7.8 Hz, 1H), 6.77 (m, 2H), 5.99 (s, 2H), 5.95 (s, 2H), 4.23 (s, 2H), 3,25 (m, 2H), 2.05 (t, J=7.7 Hz, 2H).

6.19.29 Synthesis of N-Hydroxy-3-[(3,4-methylenedioxybenzyl)-(3-(N'-hydroxyamidino)benzenesulfonyl)-amino]-propionamide (FG 1458)

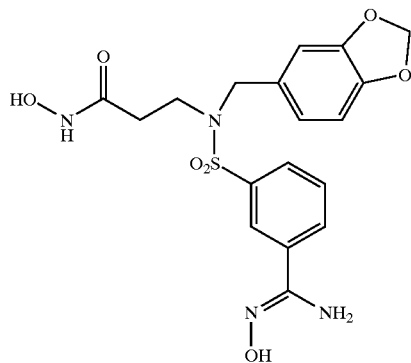

NMR (360 MHz, DMSO-d6) δ 10.36 (s, 1H), 9.87 (s, 1H), 8.97 (s, 1H), 8.11 (s, 1H), 7.96 (d, J=8.1 Hz, 1H), 7.81 (d, J=8.2 Hz, 1H), 7.62 (t, J=7.9 Hz, 1H), 6.83 (m, 3H), 6.00 (s, 2H), 5.99 (s, 2H), 4.23 (s, 2H), 3.27 (m, 2H), 2.05 (m, 2H).

6.19.30 Synthesis of N-Hydroxy-3-[(4-methoxyphenethyl)-(4-(N'-hydroxyamidino)benzenesulfonyl)-amino]-propionamide (FG 1455)

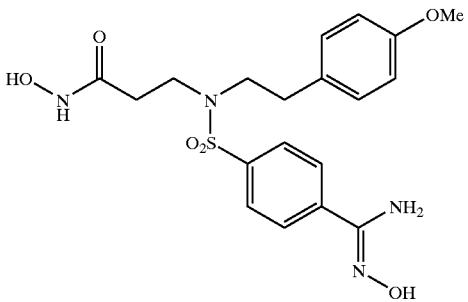

NMR (360 MHz, DMSO-d6) δ 10.46 (s, 1H), 9.91 (s, 1H), 8.74 (s, 1H), 7.86 (d, J=8.9 Hz, 2H), 7.76 (d, J=9.0 Hz, 2H), 7.09 (d, J=8.3 Hz, 2H), 6.82 (d, J=9.0 Hz, 2H), 5.92 (s, 2H), 3.70 (s, 3H), 3.35 (t, J=7.6 Hz, 2H), 3.25 (m, 2H), 2.67 (t, J=8.1 Hz, 2H), 2.24 (t, J=7.3 Hz, 2H).

6.19.31 Synthesis of N-Hydroxy-3-[(4-methoxyphenethyl)-(3-(N'-hydroxyamidino)benzenesulfonyl)-amino]-propionamide (FG 1456)

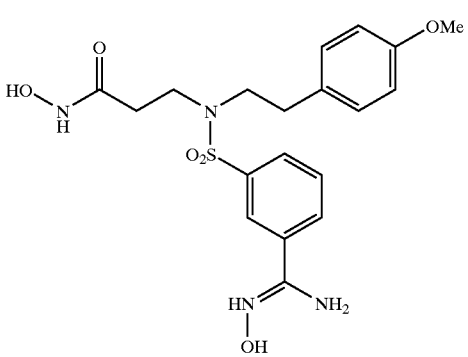

NMR (360 MHz, DMSO-d6) δ 10.47 (s, 1H), 9.86 (s, 1H), 8.75 (s, 1H), 8.08 (s, 1H), 7.94 (d, J=7.7 Hz, 1H), 7.76 (d, J=7.9 Hz, 1H), 7.60 (t, J=8.1 Hz, 1H), 7.08 (d, J=8.1 Hz, 2H), 6.82 (d, J=8.4 Hz, 2H), 5.99 (s, 2H), 3.36 (m, 2H), 3.25 (m, 2H), 2.66 (t, J=7.7 Hz, 2H), 2.24 (t, J=7.4 Hz, 2H).

6.19.32 N-Hydroxy-3-[(2-thiophenethyl)-(3-(N'-hydroxyamidino)benzenesulfonyl)-amino]-propionamide (FG 1457)

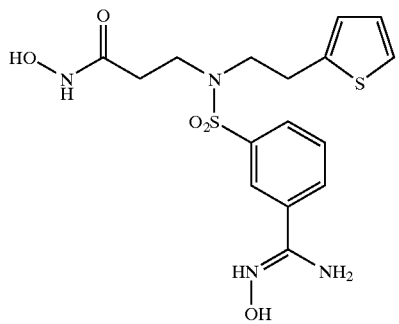

NMR (360 MHz, DMSO-d6) δ 10.46 (s, 1H), 9.86 (s, 1H), 8.74 (s, 1H), 8.08 (s, 1H), 7.95 (d, J=7.6 Hz, 1H), 7.77 (d, J=8.6 Hz, 1H), 7.61 (t, J=7.8 Hz, 1H), 7.31 (dd, J=5.3 Hz, 1H), 6.87 (m, 2H), 6.00 (s, 2H), 3.35 (m, 4H), 2.98 (t, J=7.7 Hz, 2H), 2.23 (t, J=7.6 Hz, 2H).

6.19.33 Synthesis of N-Hydroxy-3-[(2-thiophenethyl)-(4-(N'-hydroxyamidino)-benzenesulfonyl)-amino]-propionamide (FG 1409)

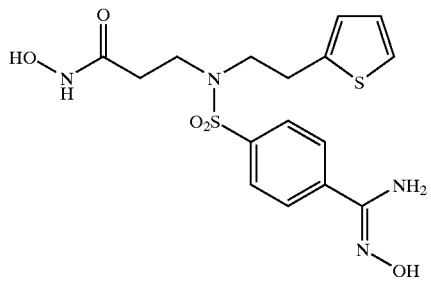

NMR (360 MHz, DMSO-d6) δ 10.45 (s, 1H), 9.92 (s, 1H), 8.74 (s, 1H), 7.87 (d, J=8.7 Hz, 2H), 7.77 (d, J=8.4 Hz, 2H), 7.32 (d, J=5.1 Hz, 1H), 6.94 (dd, J=5.1, 3.5 Hz, 1H), 6.88 (d, J=3.4 Hz, 1H), 5.93 (s, 2H), 3.35 (m, 4H), 2.99 (t, J=7.8 Hz, 2H), 2.23 (t, J=7.3 Hz, 2H).

6.20 Synthesis of N-Hydroxy-3-[(4-methoxyphenethyl)-(4-(3-(4-chlorophenyl)ureido)benzenesulfonyl)-amino]-propionamide (FG 1730)

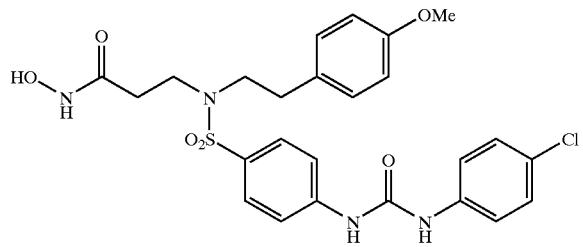

Compound 1730 can be made using reaction scheme 10. NMR (360 MHz, DMSO-d6) δ 10.46 (s, 1H), 9.16 (s, 1H), 8.91 (s, 1H), 8.74 (s, 1H), 7.68 (d, J=9.2 Hz, 2H), 7.62 (d, J=8.7 Hz, 2H), 7.47 (d, J=8.6 Hz, 2H), 7.32 (d, J=9.2 Hz, 2H), 7.10 (d, J=8.7 Hz, 2H), 6.83 (d, J=8.7 Hz, 2H), 3.71 (s, 3H), 3.22 (t, J=7.2 Hz, 2H), 3.21 (t, J=8.0 Hz, 2H), 2.67 (t, J=7.9 Hz, 2H), 2.23 (t, J=7. 2 Hz, 2H).

6.21 Synthesis of N-Hydroxy-3-[(4-methoxyphenethyl)-(4-(3-benzyl-ureido)benzenesulfonyl)-amino]-propionamide (FG 1731)

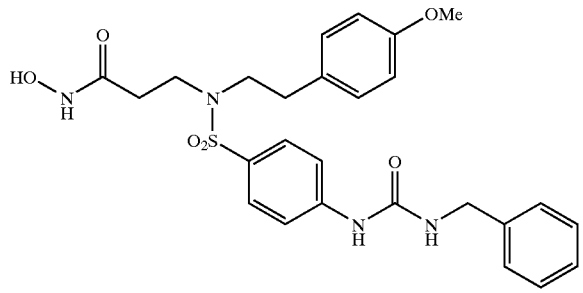

Compound 1731 can be made using reaction scheme 10. NMR (360 MHz, DMSO-d6) δ 10.45 (s, 1H), 9.04 (s, 1H), 8.98 (s, 1H), 8.73 (s, 1H), 7.87–6.82 (m, 13H), 4.30 (d, J=5.8 Hz, 2H), 3.70 (s, 3H), 3.30 (m, 2H), 3.19 (t, J=7.5 Hz, 2H), 2.66 (t, J=7.7 Hz, 2H), 2.21 (t, J=7.3 Hz, 2H).

6.22 Synthesis of N-Hydroxy-3-[(4-methoxyphenethyl)-(4-(3-phenethyl-ureido)benzenesulfonyl)-amino]-propionamide (FG 1732)

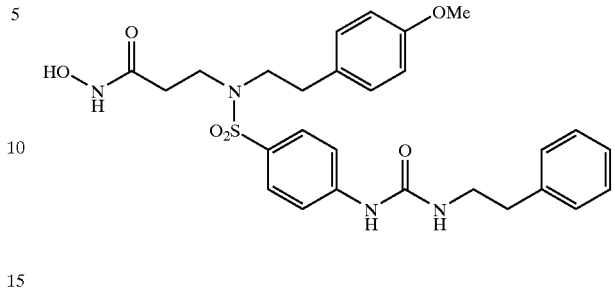

Compound 1732 can be made using reaction scheme 10. NMR (360 MHz, DMSO-d6) δ 10.44 (s, 1H), 8.95 (s, 1H), 8.89 (s, 1H), 8.72 (s, 1H), 7.62–6.81 (m, 13H), 3.71 (s, 3H), 3.34 (m, 4H), 3.19 (t, J=7.9 Hz, 2H), 2.75 (t, J=7.2 Hz, 2H), 2.65 (t, J=7.0 Hz, 2H), 2.21 (t, J=7.4 Hz, 2H).

6.23 Synthesis of N-Hydroxy-3-[(4-methoxyphenethyl)-(4-(3-methyl-ureido)benzenesulfonyl)-amino]-propionamide (FG 1733)

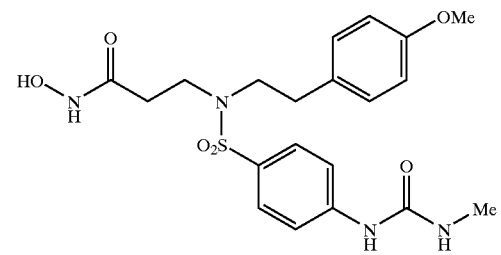

Compound 1733 can be made using reaction scheme 10. NMR (360 MHz, DMSO-d6) δ 10.45 (s, 1H), 8.98 (s, 1H), 8.73 (s, 1H), 7.59 (m, 4H), 7.09 (d, J=8.9 Hz, 2H), 6.83 (d, J=8.8 Hz, 2H), 3.70 (s, 3H), 3.30 (m, 2H), 3.18 (t, J=8.0 Hz, 2H), 2.67 (m, 2H), 2.64 (d, J=4.5 Hz, 3H), 2.21 (t, J=7.3 Hz, 2H).

6.24 Synthesis of FG 2032

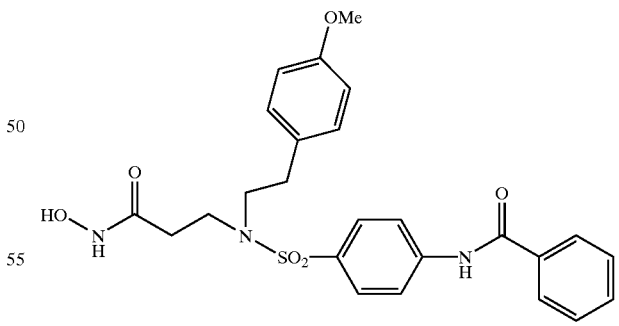

To a clear solution of methyl 3-[(4-methoxyphenethyl)-(4-nitrobenzensulfonyl)-amino]-propionate in 5:1 methanol/ethyl acetate (4.2 mL/mmol) is added by portion palladium (10%) in charcoal solid (10% w/w), followed by ammonium formate (4 eq.). The resulting mixture is refluxed for 6 hours and filtered through a pad of celite. Filtrate is concentrated and partitioned between ethyl acetate and water. The organic layer is washed with brine, dried over sodium sulfate, filtered and concentrated to give methyl 3-[(4-methoxyphenethyl)-(4-aminobenzenesulfonyl)-amino]-propionate as a brown oily product in quantitative yield.

To a solution of methyl 3-[(4-methoxyphenethyl)-(4-aminobenzenesulfonyl)-amino]-propionate in acetonitrile (7.8 mL/mmol) is added benzoyl chloride followed by triethyl amine (2 eq.). The mixture is stirred at room temperature for 5 hours and then partitioned between methylene chloride and 0.1 N hydrochloric acid aqueous solution. The acid layer is extracted with methylene chloride. Combined organic layers are washed with brine, dried over magnesium sulfate, filtered, and concentrated. The residue is then treated with 10 equivalents of freshly prepared neutralized $NH_2OH$ (1 M in methanol). The mixture is stirred at room temperature for 5 hours and concentrated. The residue is partitioned between 10:1 ethyl acetate/methanol and 1 N hydrochloric acid aqueous solution. The organic layer is washed with brine, dried over magnesium sulfate, filtered, and concentrated to give the corresponding hydroxamic acid FG 2032.

6.25 Synthesis of FG 2033

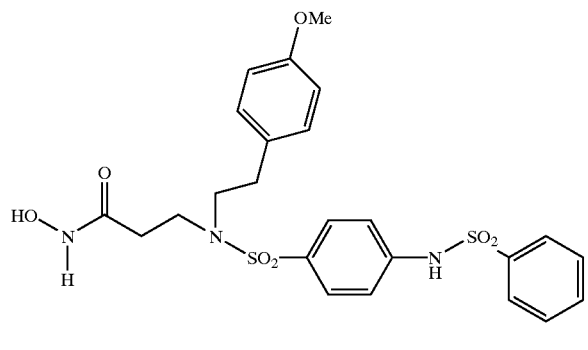

To a clear solution of methyl 3-[(4-methoxyphenethyl)-(4-nitrobenzensulfonyl)-amino]-propionate in 5:1 methanol/ethyl acetate (4.2 mL/mmol) is added by portion palladium (10%) in charcoal solid (10% w/w), followed by ammonium formate (4 eq.). The resulting mixture is refluxed for 6 hours and filtered through a pad of celite. Filtrate is concentrated and partitioned between ethyl acetate and water. The organic layer is washed with brine, dried over sodium sulfate, filtered and concentrated to give methyl 3-[(4-methoxyphenethyl)-(4-aminobenzenesulfonyl)-amino]-propionate as a brown oily product in quantitative yield.

To a solution of methyl 3-[(4-methoxyphenethyl)-(4-aminobenzenesulfonyl)-amino]-propionate in acetonitrile (7.8 mL/mmol) is added benzenesulfonyl chloride followed by triethyl amine (2 eq.). The mixture is stirred at room temperature for 5 hours and then partitioned between methylene chloride and 0.1 N hydrochloric acid aqueous solution. The acid layer is extracted with methylene chloride. Combined organic layers are washed with brine, dried over magnesium sulfate, filtered, and concentrated. The residue is then treated with 10 equivalents of freshly prepared neutralized $NH_2OH$ (1 M in methanol). The mixture is stirred at room temperature for 5 hours and concentrated. The residue is partitioned between 10:1 ethyl acetate/methanol and 1 N hydrochloric acid aqueous solution. The organic layer is washed with brine, dried over magnesium sulfate, filtered, and concentrated to give the corresponding hydroxamic acid FG 2033.

6.26 Synthesis of Other Compounds

Other compounds of the invention can be synthesized by routine modification of the above-described syntheses, or by other methods that are well-known in the art. Appropriate starting materials are commercially available or can by synthesized using routine methods.

7. EXAMPLE: C-PROTEINASE $IC_{50}$ ASSAYS

The following assay may be used to determine the level of activity and effect of the different compounds of the present invention on C-proteinase activity.

To determine inhibition of recombinant human C-proteinase, 60 μl of a reaction mix (final concentration in 100 μl of 0.05M Tris-HCl pH 7.6, 0.1M NaCl, 0.02% Brij-35, 5 mM $CaCl_2$ and 50 μM of a fluorogenic peptide) was added to 20 μl of the inhibitor in a 96 well plate. The reaction was started with the addition of 20 μl of the recombinant human C-proteinase mix. The reaction proceeded for 4 hours at 37° C. and the fluorescence was measured using a Bio-Tek Fl-600. The $IC_{50}$ was determined by plotting the percentage of activity versus the inhibitor concentration and estimating the inhibitor concentration that gives 50% activity of the control with no inhibitor.

The $IC_{50}$ value of the inhibitors that have been tested is shown in TABLE 1.

TABLE 1

$IC_{50}$ (μM) Of Various C-Proteinase Inhibitors

| Compound (FG#) | $IC_{50}$ (μM) |
|---|---|
| 121 | 9 |
| 122 | 10 |
| 123 | 39 |
| 124 | 2 |
| 125 | 29 |
| 126 | 1 |
| 128 | 15.3 |
| 134 | 7 |
| 202 | 72.8 |
| 204 | 22.1 |
| 206 | 1.05 |
| 208 | 1.68 |
| 1131 | 80.5 |
| 1132 | 8 |
| 1268 | 3.03 |
| 1237 | 3.57 |
| 1270 | 1.21 |
| 1273 | 0.63 |
| 1300 | 2.43 |
| 1301 | 14.5 |
| 1302 | 5.7 |
| 1306 | 1.71 |
| 1335 | 36.5 |
| 1357 | 0.55 |
| 1360 | 1.17 |
| 1361 | 0.88 |
| 1362 | 1.51 |
| 1363 | 12.38 |
| 1364 | 2.60 |
| 1365 | 0.59 |
| 1366 | 2.85 |
| 1367 | 1.47 |
| 1368 | 6.01 |
| 1369 | 0.23 |
| 1370 | 0.87 |
| 1371 | 0.91 |
| 1372 | 1.70 |
| 1373 | 0.35 |
| 1379 | >10 |
| 1380 | >10 |
| 1405 | 1.46 |
| 1407 | 0.58 |
| 1408 | 0.75 |
| 1409 | 0.18 |
| 1410 | 1.77 |
| 1411 | 0.39 |
| 1414 | 3.50 |

TABLE 1-continued

IC$_{50}$ ($\mu$M) Of Various C-Proteinase Inhibitors

| Compound (FG#) | IC$_{50}$ ($\mu$M) |
|---|---|
| 1415 | 3.85 |
| 1416 | 0.82 |
| 1417 | 1.67 |
| 1418 | 5.37 |
| 1419 | 3.95 |
| 1420 | 3.00 |
| 1421 | 13.7 |
| 1422 | 8.36 |
| 1423 | 2.61 |
| 1424 | 8.88 |
| 1425 | 1.32 |
| 1455 | 0.086 |
| 1456 | 0.4 |
| 1457 | 0.84 |
| 1458 | 0.25 |
| 1459 | 7.12 |
| 1460 | 0.29 |
| 1461 | 12.90 |
| 1462 | 19.13 |
| 1463 | 0.70 |
| 1464 | 0.35 |
| 1465 | 9.07 |
| 1466 | 17.49 |
| 1467 | 8.39 |
| 1468 | 2.42 |
| 1469 | 15.39 |
| 1470 | 9.07 |
| 1471 | 4.08 |
| 1472 | 6.32 |
| 1473 | 8.85 |
| 1492 | 0.32 |
| 1496 | 0.25 |
| 1730 | 0.3 |
| 1731 | 0.010 |
| 1732 | 0.045 |
| 1733 | 0.057 |
| 1858 | 0.01 |
| 1891 | 0.026 |
| 1894 | 0.01 |
| 1895 | 0.784 |
| 1896 | 0.141 |
| 1943 | 0.81 |
| 1944 | 0.092 |
| 2032 | 0.41 |
| 2033 | 0.47 |

7.1 Tissue Culture Assay for the Determination of C-proteinase Activity and the IC$_{50}$ of Inhibitors C-proteinase activity and the IC$_{50}$ of inhibitors in vivo may be determined in tissue culture assays by measuring the production of procollagen and mature collagen in conditioned medium before and after treatment with a particular compound. The ratio of collagen and procollagen will directly correlate to the cellular conversion of the precursor to the mature collagen product, and as such indicate the C-proteinase activity.

Alternatively, the media content of C-propeptide/cell may be determined, and compared for untreated cells and inhibitor-treated cells.

7.2 Animal Models for the Determination of C-proteinase Activity and the Efficacy of Inhibitors Several animal models which mimic clinical disorders related to unregulated or inappropriate collagen production are known in the art and may be employed to determine the in vivo efficacy of the compounds of the invention. These animal models include a wound chamber model in rats (Schilling et al., 1959, Surgery 46:702–710), an estradiol stimulated uterus expansion model (Mandell et al., 1982, The Journal of Biological Chemistry 257:5268–5273), and an induced angiogenesis model (Matrigel) (Passaniti et al., 1992, Laboratory Investigation 67:519–528). Further animal models include clinical disorder models like liver fibrosis models (Tsukamoto et al., 1990, Seminar in Liver Disease 10:56–65; Kock-Weser, 1952, Laboratory Investigation 1:324–331; Marrione, 1949, American Journal of Pathology 25:273–285; Tams, 1957, American Journal of Pathology 33:13–27; Wahl et al., 1986, Journal of Experimental Medicine 163:884–902), a pulmonary fibrosis model (Kelly et al., 1980, Journal of Laboratory Clinical Medicine 96:954–964), arterial restenosis models (Jackson, 1994, Trends of Cardiovascular Medicine 4:122–130; Clowes et al., 1983, Laboratory Investigation 49:327–333), a kidney fibrosis model (Yamamoto et al., 1987, Kidney International 32:514–525), a tendon repairing model (Franklin et al., 1986, The Journal of Laboratory and Clinical Medicine 108:103–108), a tumor growth model (Kiohs, et al., 1985, JNCL 75:353–359), a trabeculectomy model (Lahery et al., 1989, Journal of Ocular Pharmacology 5:155–179), and an abdominal adhesions model (Williams et al., 1992, Journal of Surgical Research 52:65–70).

7.3 Measurement of Cytotoxicity

C-proteinase inhibitors were studied in cytotoxicity assays wherein quiescent cells were exposed to C-proteinase inhibitors for a given time and cell viability measured. By examining cellular metabolic activity, cell viability and cell survival were determined.

C-proteinase inhibitors were tested on human foreskin fibroblasts that had been grown to confluence in 96 well microtiter plates in Dulbecco's Modified Eagle Medium (DMEM) containing 10% fetal calf serum. Shortly before adding the inhibitors, the media was removed and 90 $\mu$l per microtiter well of fresh serum-free DMEM was added to the cells. The C-proteinase inhibitors were made up as concentrated stocks containing compound at 250 $\mu$M in the presence of 5% DMSO as solvent. A concentrated stock of 10 $\mu$l was added to each microtiter well to give a final compound concentration of 25 $\mu$M in the presence of 0.5% DMSO. The cells were incubated in the presence of the C-proteinase inhibitor for 48 hours, and then cell viability and survival were measured as a function of metabolic activity. To examine cellular metabolic activity, 10 $\mu$l of WST-1 reagent (Boehringer Mannheim) was added to each well of a 96 well microtiter plate containing quiescent cells that were already in media. The plate was incubated at 37° C. for 120 minutes and removed. The absorbance at 450 nm–650 nm was recorded. Increased absorbance was observed in cells that were healthy. Controls included untreated healthy cells, and cells killed with 0.1% saponin.

Cytotoxicity was evaluated as a function of cellular survival. Cellular survival was determined by measuring the metabolic activity of the quiescent cells after exposure to the C-proteinase inhibitors. To determine the metabolic activity of the cells, the color change of a trazolium dye over time was examined according to Mossmann, 1938, Immunol. Methods 65:66; Carmichael, 1987, Cancer Res 47:936, incorporated herein by reference. Healthy cells cleaved the dye producing a colored product that can be quantitated. Unhealthy cells demonstrated a reduction in metabolic activity and reduced color change. Dead cells had no metabolic activity and no effect on the dye was shown.

The amount of dye cleaved by cells that had been incubated with inhibitor, expressed as a percentage relative to untreated cells, is shown in TABLE 2. Cells that register at 60% or below are considered either very sick or dead. Control cells that were intentionally killed give a value of close to 20%.

TABLE 2

Percent Metabolic Activity of Fibroblasts Exposed To Various C-Proteinase Inhibitors Relative to Untreated Fibroblasts

| Compound | Percent |
|---|---|
| 1300 | 109.9 |
| 1301 | 110.7 |
| 1302 | 102.3 |
| 1305 | 93.9 |
| 1306 | 106.3 |
| 1335 | 113.3 |
| 1357 | 108.1 |
| 1359 | 101.1 |
| 1360 | 114.5 |
| 1361 | 103.4 |
| 1362 | 119.4 |
| 1363 | 114.9 |
| 1364 | 117.2 |
| 1365 | 121.2 |
| 1366 | 107.4 |
| 1367 | 114.5 |
| 1368 | 110.2 |
| 1369 | 117.1 |
| 1370 | 117.9 |
| 1371 | 114.4 |
| 1372 | 109.2 |
| 1373 | 103.2 |
| 1374 | 117.6 |
| 1379 | 100.3 |
| 1380 | 107.7 |
| 1405 | 114.5 |
| 1407 | 111.5 |
| 1408 | 113.1 |
| 1409 | 108.8 |
| 1410 | 108.6 |
| 1411 | 108.2 |
| 1414 | 112.6 |
| 1415 | 109.6 |
| 1416 | 92.8 |
| 1417 | 120.3 |
| 1418 | 101.0 |
| 1419 | 104.7 |
| 1420 | 124.4 |
| 1421 | 118.2 |
| 1422 | 118.6 |
| 1423 | 119.9 |
| 1424 | 111.7 |
| 1425 | 109.5 |
| 1455 | 115.1 |
| 1456 | 106.8 |
| 1457 | 107.4 |
| 1458 | 111.0 |
| 1459 | 107.3 |
| 1460 | 108.9 |
| 1461 | 112.7 |
| 1462 | 112.6 |
| 1463 | 110.0 |
| 1464 | 111.0 |
| 1465 | 105.4 |

7.5 Specificity

The compounds of the present invention were assayed against other matrix metalloproteinases (MMPs) to determine compound specificity. MMP1 (collagenase), MMP2 (gelatinase) and MMP9 (gelatinase B) were assayed according to the protocols provided in WO 93/34918 for MMP1 and MMP2. The specificity of selected compounds of the present invention against MMP1, MMP2 and MMP9 are provided in Table 3.

TABLE 3

IC50 (uM) of Select C-Proteinase Inhibitors Against MMPs

| FG # | $IC_{50}$ of Cpase ($\mu$M) | $IC_{50}$ of MMP1/CPase ($\mu$M) | $IC_{50}$ of MMP2/CPase ($\mu$M) | $IC_{50}$ of MMP9/CPase ($\mu$M) |
|---|---|---|---|---|
| 126 | 1.8 | >8.0 | 2.2 | 3.5 |
| 206 | 1.05 | >10.7 | 2.1 | 1.5 |
| 208 | 1.68 | >11.2 | 0.46 | 0.30 |
| 1455 | 0.086 | >3.6 | >4.5 | >4.5 |
| 1731 | 0.01 | >891 | >742.5 | >742.5 |
| 1732 | 0.032 | >255 | >360.5 | >360.5 |
| 1858 | 0.01 | >1061 | >855.0 | >855.0 |
| 1891 | 0.026 |  | >112.1 | >112.1 |
| 1894 | 0.01 | >516 | 94.9 | >253.9 |

The present invention is not to be limited in scope by the exemplified embodiments which are intended as illustrations of single aspects of the invention, and any compounds and methods for the use thereof which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

All references cited herein are hereby incorporated by reference in their entirety.

What is claimed is:

1. A compound having an inhibitory effect on C-proteinase and having the structural formula:

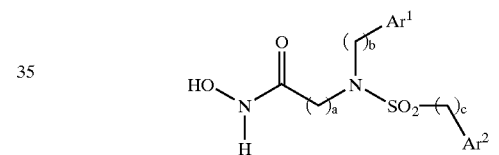

or pharmaceutically acceptable salts thereof, wherein:
a is an integer from 2 to 4;
b is an integer from 0 to 4;
c is an integer from 0 to 4;
$Ar^1$ is selected from the group consisting of ($C_5$–$C_{20}$) aryl, ($C_5$–$C_{20}$) aryl independently substituted with one or more $Y^1$, 5–20 membered heteroaryl, and 5–20 membered heteroaryl independently substituted with one or more $Y^1$;
$Ar^2$ is selected from the group consisting of ($C_5$–$C_{20}$) aryl, ($C_5$–$C_{20}$) aryl independently substituted with one or more $Y^2$, 5–20 membered heteroaryl, and 5–20 membered heretoaryl independently substituted with one or more $Y^2$;
each $Y^1$ is independently selected from the group consisting of an electron-donating functional group, an electron-withdrawing functional group, and a lipophilic functional group; and
each $Y^2$ is independently selected from the group consisting of a functional group having an acidic hydrogen, a functional group capable of participating in a hydrogen bond, a polar functional group, an electron-withdrawing functional group, an electron-donating functional group, and a lipophilic functional group,
with the proviso that when a is two, b and c are each zero and $Ar^1$ is phenyl, then $Ar^2$ is other than 4-chlorophenyl or 4-bromophenyl.

2. The compound of claim 1 wherein $Y^1$ and $Y^2$ are each independently selected from the group consisting of halogen, —R, —OR, —SR, —NRR, —NO, —NO$_2$, —CN, -trihalomethyl, and —S$_2$NH$_2$; where each R is independently selected from the group consisting of H, (C$_1$–C$_8$) alkyl, (C$_2$–C$_8$) alkenyl, and (C$_2$–C$_8$) alkynyl.

3. The compound of claim 1 wherein each $Y^2$ is independently selected from the group consisting of -halogen, -trihalomethyl, —R, —C(O)OR, —CN, —C(O)—NR—OR, —C(NRR)=N—OR, —C(O)—R, —C(O)NRR, —C(S)NRR, —C(NHR)=NR, —NRR, —NO$_2$, —NH—C(O)R, —NH—C(O)—NRR, —NH—C(O)—OR, —NH—SO$_2$—R, —NH—C(S)—NRR, —NH—C(O)R, —NR—C(O)—NRR, —NR—C(S)—NRR, —OR, —P(O)(OH)(NRR), —P(O)(OH)$_2$, —SO$_2$R, —S(O)—R, —SO$_3$H, —SR, and -tetrazole; where each R is independently selected from the group consisting of H, (C$_1$–C$_8$) alkyl, (C$_2$–C$_8$) alkenyl, (C$_2$–C$_8$) alkynyl, (C$_5$–C$_{20}$) aryl, (C$_6$–C$_{26}$) alkaryl, 5–20 membered heteroaryl and 6–26 membered alk-heteroaryl.

4. The compound of claim 1 wherein Ar$^1$ is selected from the group consisting of (C$_5$–C$_{20}$) aryl and (C$_5$–C$_{20}$) aryl independently substituted with one or more $Y^1$; and Ar$^2$ is selected from the group consisting of (C$_5$–C$_{20}$) aryl and (C$_5$–C$_{20}$) aryl independently substituted with one or more $Y^2$.

5. The compound of claim 4 having the structural formula:

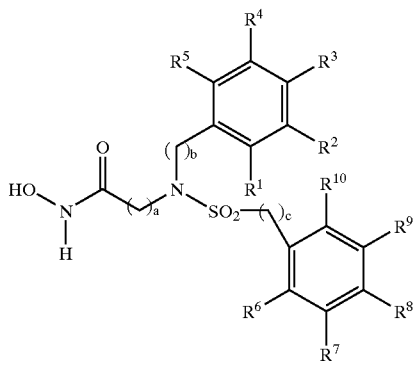

or pharmaceutically acceptable salts thereof, wherein a, b, and c are as defined in claim 1;

$R^1$, $R^2$, $R^3$, $R^4$ and $R^5$ are each independently selected from the group consisting of H, an electron-donating functional group, an electron-withdrawing functional group, and a lipophilic functional group;

$R^6$, $R^7$, $R^8$, $R^9$ and $R^{10}$ are each independently selected from the group consisting of H, a functional group having an acidic hydrogen, a functional group capable of participating in a hydrogen bond, a polar functional group, an electron-withdrawing functional group, an electron-donating functional group, and a lipophilic functional group;

with the proviso that when a is two, b and c are each zero and $R^1$, $R^2$, $R^4$, $R^5$, $R^6$, $R^7$, $R^9$ and $R^{10}$ are each —H, then $R^8$ is other than —F or —Cl.

6. The compound of claim 5 wherein $R^1$, $R^2$, $R^3$, $R^4$ and $R^5$ are each independently selected from the group consisting of —R, halogen, —OR, —SR, —NRR, —COOH, —SO$_3$H, —P(O)(OH)$_{21}$, —C(O)—NH—OH, —P(O)(OH)(NRR), and tetrazole; where each R is independently selected from the group consisting of H, (C$_1$–C$_8$) alkyl, (C$_2$–C$_8$) alkenyl and (C$_2$–C$_8$) alkynyl.

7. The compound of claim 5 wherein $R^6$, $R^7$, $R^8$, $R^9$ and $R^{10}$ are each independently selected from the group consisting of —H, —C(NHR)=N—OH, —NH—C(O)R, —NH—C(O)—NRR, —C(S)NHR, —C(O)NHR, —CO$_2$H, —NR$_2$, —C(NHR)=NR, —NH—(CO)—OR, —NH—SO$_2$—R, —C≡N, —OR, —SR, —SO$_2$R, —S(O)R, —NO$_2$, and trihalomethyl; where each R is independently selected from the group consisting of H, (C$_1$–C$_8$) alkyl, (C$_2$–C$_8$) alkenyl and (C$_2$–C$_8$) alkynyl.

8. The compound of claim 5 wherein:

a is an integer from 2 to 4;

b is an integer from 0 to 4; and c is zero.

9. The compound of claim 8 wherein:

a is an integer from 2 to 3;

b is an integer from 0 to 2;

$R^3$ and $R^4$ are each independently selected from the group consisting of —H, halogen, —OR, and trihalomethyl;

$R^5$ is selected from the group consisting of —H and —OR;

$R^6$ is selected from the group consisting of —H, —C(O)OR, —C(NH$_2$)=NOH and —SO$_2$R;

$R^7$ is selected from the group consisting of —H and —C(NH$_2$)=NOH;

$R^8$ is selected from the group consisting of —H, —OR, —NO$_2$, —C(O)OR, —SO$_2$R and —C(NH$_2$)=NOH; and each R is independently selected from the group consisting of H, (C$_1$–C$_3$) alkyl, (C$_2$–C$_3$) alkenyl, and (C$_2$–C$_3$) alkynyl.

10. The compound of claim 5 selected from the group consisting of N-hydroxy-3-[(benzyl)-(4-methoxy-benzenesulfonyl)-amino]-propionamide, N-benzyl-N-p-methoxybenzene sulfonyl-g-butyryl hydroxamic acid, N-hydroxy-3-[(phenyl)-(4-methoxy-benzenesulfonyl)-amino)-propionamide, N-phenyl-N-p-methoxybenzene sulfonyl-g-aminobutyryl hydroxamic acid, N-hydroxy-3-[(phenethyl)-(4-methoxybenzenesulfonyl)-amino]-propionamide, N-(2-phenyl)ethyl-N-p-methoxybenzenesulfonyl-g-aminobutyryl hydroxamic acid, N-hydroxy-3-[(4-methoxyphenethyl)-(4-methoxybenzenesulfonyl)-amino]-propionamide, N-hydroxy-3-[(4-methoxyphenyl)-(4-methoxybenzenesulfonyl)-amino]-propionamide, N-hydroxy-3-[(4-nitrobenzenesulfonyl)-(phenethyl)-amino]propionamide, N-hydroxy-3-[(4-chlorophenethyl)-(4-methoxybenzenesulfonyl)-amino]-propionamide, N-hydroxy-3-[(4-methoxybenzenesulfonyl)-(3,4-dimethoxyphenethyl)-amino]propionamide, N-hydroxy-3-[(2-methoxyphenethyl)-(4-carboxy-benzenesulfonyl)-amino]-propionamide, N-hydroxy-3-[(4-methoxyphenyl)-(4-(N'-hydroxyamidino)benzenesulfonyl)-amino]-propionamide, N-hydroxy-3-[(3-(N'-hydroxyamidino)benzenesulfonyl)-(4-methoxyphenethyl)-amino]propionamide, N-hydroxy-3-[(2-(N'-hydroxyamidino)benzenesulfonyl)-(4-methoxyphenethyl)-amino]propionamide, N-hydroxy-3-[(4-methylsulfonylbenzenesulfonyl)-(4-methoxyphenethyl)-amino]propionamide, N-hydroxy-3-[(2-methylsulfonylbenzenesulfonyl)-(4-methoxyphenethyl)-amino]propionamide, N-hydroxy-3-[(2-carbomethoxybenzenesulfonyl)-(4-methoxyphenethyl)-amino]propionamide, and N-hydroxy-3-[(4-(N'-hydroxyamidino)benzenesulfonyl)-(4-pentybenzyl)-amino]propionamide.

11. The compound of claim 1 having the structural formula:

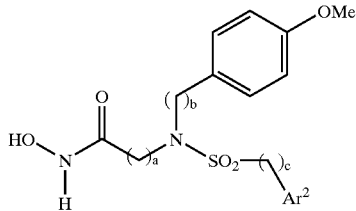

or pharmaceutically acceptable salts thereof, wherein a, b, c, $Ar^2$, and $Y^2$ are as defined in claim 1.

12. The compound of claim 11 wherein $Y^2$ is selected from the group consisting of -halogen, -trihalomethyl, —R, —C(O)OR, —CN, —C(O)—NR—OR, —C(NRR)=N—OR, —C(O)—R, —C(O)NRR, —C(S)NRR, —C(NHR)=NR, —NRR, —NO$_2$, —NH—C(O)R, —NH—C(O)—NRR, —NH—C(O)—OR, —NH—SO$_2$—R, —NH—C(S)—NRR, —NH—C(O)R, —NR—C(O)—NRR, —NR—C(S)—NRR, —OR, —P(O)(OH)(NRR), —P(O)(OH)$_2$, —SO$_2$R, —S(O)—R, —SO$_3$H, —SR, and -tetrazole; where each R is independently selected from the group consisting of H, (C$_1$–C$_8$) alkyl, (C$_2$–C$_8$) alkenyl, (C$_2$–C$_8$) alkynyl, (C$_5$–C$_{20}$) aryl, (C$_6$–C$_{26}$) alkaryl, 5–20 membered heteroaryl and 6–26 membered alk-heteroaryl.

13. The compound of claim 1 wherein $Ar^2$ is selected from the group consisting of phenyl, phenyl mono-substituted with $Y^2$, thienyl, and thienyl mono-substituted with $Y^2$.

14. The compound of claim 11 wherein $Ar^2$ is selected from the group consisting of phenyl, phenyl mono-substituted with $Y^2$ thienyl, and thienyl mono-substituted with $Y^2$.

15. The compound of claim 11 that is selected from the group consisting of N-hydroxy-3-[(4-methoxyphenethyl)-(4-methoxybenzenesulfonyl)-amino]-propionamide, N-hydroxy-3-[(4-methoxyphenyl)-(4-methoxybenzenesulfonyl)-amino]-propionamide, N-hydroxy-3-[(4-methoxyphenethyl)-(4-(N'-hydroxyamidino)benzenesulfonyl)-amino]-propionamide, N-hydroxy-3-[(3-(N'-hydroxyamidino)benzenesulfonyl)-(4-methoxyphenethyl)-amino]propionamide, N-hydroxy-3-[(2-(N'-hydroxyamidino)benzenesulfonyl)-(4-methoxyphenethyl)-amino]propionamide, N-hydroxy-3-[(4-methylsulfonylbenzenesulfonyl)-(4-methoxyphenethyl)-amino]propionamide, N-hydroxy-3-[(2-methylsulfonylbenzenesulfonyl)-(4-methoxyphenethyl)-amino]propionamide, N-hydroxy-3-[(2-carbomethoxybenzenesulfonyl)-(4-methoxyphenethyl)-amino]propionamide, N-hydroxy-3-[(4-methoxyphenethyl)-(5 -(N'-hydroxyaminocarbonyl)thiophen-2-sulfonyl)-amino]-propionamide, and N-hydroxy-3-[(4-methoxyphenethyl)-(2-carboxybenzenesulfonyl)-amino]-propionamide.

16. The compound of claim 1 wherein $Ar^2$ is phenyl substituted with one or more $Y^2$.

17. The compound of claim 16 wherein $Y^2$ are each independently selected from the group consisting of —R, —OR, —SR, —NRR, —NO$_2$, —CN, halogen, trihalomethyl, —C(O)R, —C(O)OR, —C(O)NRR, —C(NRR)=NOR, —NR—C(O)R, —NR—C(O)—NRR, —NR—C(O)—OR, tetrazol-5-yl, —NR—SO$_2$—R, and —SO$_2$R; where each R is independently selected from the group consisting of H, (C$_1$–C$_8$) alkyl, (C$_2$–C$_8$) alkenyl, and (C$_2$–C$_8$) alkynyl.

18. The compound of claim 16 having the structural formula:

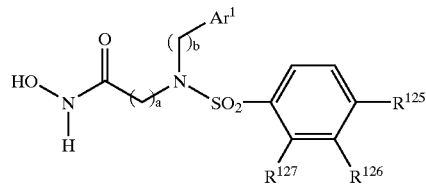

and pharmaceutically acceptable salts thereof, wherein $R^{125}$, $R^{126}$, and $R^{127}$ are each independently selected from the group consisting of —H, —OR, —C(O)R, —C(O)OR, —C(O)NRR, —C(NH$_2$)NOH, —NH—C(O)R, —NR—C(O)—NRR, —NR—C(O)—OR, —NR—SO$_2$—R, -tetrazol-5-yl and —SO$_2$R; and each R is independently selected from the group consisting of hydrogen, (C$_1$–C$_6$) alkyl, (C$_2$–C$_6$) alkenyl and (C$_2$–C$_6$) alkynyl.

19. The compound of claim 18 wherein $Ar^1$ is selected from the group consisting of phenyl, pyridinyl, 1,3-benzodioxolyl, 1,4-benzodioxanyl, and thienyl.

20. The compound of claim 18 that is selected from the group consisting of N-hydroxy-3-[(pyridin-2-yl-ethyl)-(4-methoxybenzenesulfonyl)-amino]-propionamide, N-hydroxy-3-[benzodioxan-2-yl-methyl))-(4-methoxybenzene(-sulfonyl)-amino]-propionamide, N-hydroxy-3-[(3,4-methylenedioxybenzyl)-(4-methoxybenzenesulfonyl)-amino]-propionamide, N-hydroxy-3-[(3,4-methylenedioxybenzyl)-4-acetylamino-benzenesulfonyl)-amino]-propionamide, N-hydroxy-3-[(3,4-methylenedioxybenzyl)-(4-n-butoxybenzenesulfonyl)-amino]-propionimide, N-hydroxy-3-[(3,4-methylenedioxybenzyl)-(3,4-dimethoxybenzene-sulfonyl)-amino]-propionamide, N-hydroxy-3-[(3,4-methylenedioxybenzyl)-(4-methylsulfonylbenezene)-amino]-propionamide, N-hydroxy-3-[(3,4-methylenedioxybenzyl)-(4-(N'-hydroxyamidino)benzenesulfonyl)-amino]-propionamide, N-hydroxy-3-[(3-(N'-hydroxyamidino)benzenesulfonyl)-(3,4-methylenedioxybenzyl)-amino]propionamide, N-hydroxy-3-[(2-thiophenethyl)-(phenylmethylsulfonyl)-amino]-propionamide, N-hydroxy-3-[(2-thiophenethyl)-(4-n-butoxybenzenesulfonyl)-amino]-propionamide, N-hydroxy-3-[(2-thiophenethyl)-(4-acetylaminobenzenesulfonyl)-amino]-propionamide, N-hydroxy-3-[(2-thiophenethyl)-(4-methylsulfonylbenzenesulfonyl)-amino]-propionamide, N-hydroxy-3-[(2-thiophenethyl)-(3-(N'-hydroxyamidino)benzenesulfonyl)-amino]-propionamide, N-hydroxy-3-[(2-thiophenethyl)-(4-(N'-hydroxyamidino)benzenesulfonyl)-amino]-propionamide, N-hydroxy-3-[(benzyl)-(4-methoxybenzenesulfonyl)-amino]-propionamide, N-benzyl-N-p-methoxybenzenesulfonyl-g-butyryl hydroxamic acid, N-hydroxy-3-[(phenyl)-(4-methoxy-benzenesulfonyl)-amino]-propionamide, N-phenyl-N-p-methoxybenzene sulfonyl-g-aminobutyryl hydroxamic acid, N-hydroxy-3-[(phenethyl)-(4-methoxybenzenesulfonyl)-amino]-propionamide, N-(2-phenyl)ethyl-N-p-methoxybenzenesulfonyl-g-aminobutyryl hydroxamic acid, N-hydroxy-3-[(4-methoxyphenethyl)-(4-methoxybenzenesulfonyl)-amino]-propionamide, N-hydroxy-3-[(4-methoxyphenyl)-(4-methoxybenzenesulfonyl)-amino]-propionamide, N-hydroxy-3-[(4-chlorophenethyl)-(4-methoxybenzenesulfonyl)-amino]-propionamide, N-hydroxy-3-[(2-methoxyphenethyl)-(4-carboxybenzenesulfonyl)-amino]-propionamide, N-hydroxy-3-[(4-methoxyphenyl)-(4-(N'-hydroxyamidino)benzenesulfonyl)-amino]-propionamide, N-hydroxy-3-[(3-(N'- hydroxyamidino)benzenesulfonyl)-(4-methoxyphenethyl)-amino]propionamide, N-hydroxy-3-[(4-methylsulfonylbenzenesulfonyl)-(4-methoxyphenethyl)-amino]propionamide, N-hydroxy-3-[(4-nitrobenzenesulfonyl)-(phenethyl)-amino]propionamide, N-hydroxy-3-[(2-(N'-hydroxyamidino)benzenesulfonyl)-(4-methoxyphenethyl)-amino]propionamide, N-hydroxy-3-[(2-methylsulfonylbenzenesulfonyl)-(4-methoxyphenethyl)-amino]proponamide, and N-hydroxy-3-[(2-carbomethoxybenzenesulfonyl)-(4-methoxyphenethyl)-amino]propionamide.

21. The compound of claim 1 wherein
each $Y^1$ is independently selected from the group consisting of —SO$_2$NH$_2$, —R', —OR', —SR', —NR'R', —NO$_2$, —CN, -halogen and trihalomethyl;
each $Y^2$ is independently selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', -tetrazol-5-yl, —NR'—C(O)—OR', —C(NR'R')=NR', —S(O)—R', —S(O)—R", and —NR'—C(S)—NR'R';
each R' is independently selected from the group consisting of H, (C$_1$-C$_8$) alkyl, (C$_2$-C$_8$) alkenyl and (C$_2$-C$_8$) alkynyl;
each R" is independently selected from the group consisting of (C$_5$-C$_{20}$) aryl and (C$_5$-C$_{20}$) aryl independently substituted with one or more —OR', —SR', —NR'R', —NO$_2$, —CN, halogen or trihalomethyl groups.

22. The compound of claim 1 wherein Ar$^1$ is thienyl with the proviso that when a and b are each one and Ar$^2$ is phenyl then c is other than zero.

23. The compound of claim 22 wherein
each $Y^2$ is independently selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', tetrazol-5-yl, —NR'—C(O)—OR', —C(NR'R')=NR', —S(O)—R', —S(O)—R", and —NR'—C(S)—NR'R';
each R' is independently selected from the group consisting of —H, (C$_1$-C$_8$) alkyl, (C$_2$-C$_8$) alkenyl and (C$_2$-C$_8$) alkynyl; and
each R" is independently selected from the group consisting of (C$_5$-C$_{20}$) aryl and (C$_5$-C$_{20}$) aryl independently substituted with one or more —OR', —SR', —NR'R', —NO$_2$, —CN, halogen or trihalomethyl groups.

24. The compound of claim 22 wherein Ar$^1$ is thien-2-yl.
25. The compound of claim 24 that is selected from the group consisting of FG 1417, FG 1419, FG 1420, FG 1421, FG 1423, FG 1425 and FG 1472.
26. The compound of claim 22 wherein:
Ar$^2$ is selected from the group consisting of phenyl, phenyl independently mono- or di-substituted with $Y^2$, 5–10 membered heteroaryl, and 5–10 membered heteroaryl independently mono- or di-substituted with $Y^2$;
each $Y^2$ is independently selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', tetrazol-5-yl, —NR'—C(O)—OR', —C(NR'R')=NR', —S(O)—R', —S(O)—R", and —NR'—C(S)—NR'R';
each R' is independently selected from the group consisting of —H, (C$_1$-C$_8$) alkyl, (C$_2$-C$_8$) alkenyl and (C$_2$-C$_8$) alkynyl; and
each R" is independently selected from the group consisting of phenyl and phenyl independently mono- or di-substituted with halogen, —NR'R', —NO$_2$ or —CN, with the proviso that when a and b are each one and Ar$^2$ is phenyl then c is other than zero.

27. The compound of claim 22 wherein Ar$^2$ is selected from the group consisting of thienyl, 2,1,3-benzothiadiazolyl, imidazolyl, 1,7-thiazopyrrolizinyl, phenyl, and phenyl independently mono-, di- or tri-substituted-with $Y^2$.

28. The compound of claim 22 having the structural formula:

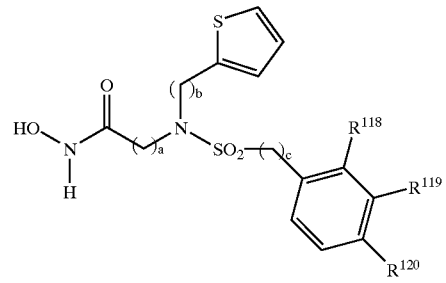

wherein $R^{118}$, $R^{119}$ and $R^{120}$ are each independently selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', tetrazol-5-yl, and —NR'—C(O)—OR';
each R' is independently selected from the group consisting of —H, (C$_1$-C$_8$) alkyl, (C$_2$-C$_8$) alkenyl and (C$_2$-C$_8$) alkynyl; and
R" is independently selected from the group consisting of phenyl and phenyl independently mono-, di-substituted or tri-substituted with halogen or —CN, with the proviso that when a and b are each one then c is other than zero.

29. The compound of claim 28 selected from the group consisting of N-hydroxy-3-[(4-methoxybenzenesulfonyl)-(2-thiophenethyl)-amino]propionamide, N-hydroxy-3-[(4-carboxybenzenesulfonyl)-(2-thiophenethyl)-amino]propionamide, N-hydroxy-3-[(3-carboxybenzenesulfonyl)-(2-thiophenethyl)-amino]propionamide, N-hydroxy-3-[(2-thiophenethyl)-4-(N'-hydroxyamidino)benzenesulfonyl)-amino]-propionamide, N-hydroxy-3-[(2-thiophenethyl)-(4-acetylaminobenzenesulfonyl)-amino]-propionamide, N-hydroxy-3-[(2-thiophenethyl)-(phenylmethylsulfonyl)-amino]-propionamide, N-hydroxy-3-[(2-thiophenethyl)-(4-n-butoxybenzenesulfonyl)-amino]-propionamide, N-hydroxy-3-[(4-(2-cyano-3-chlorophenoxy)benzenesulfonyl)-(2-thiophenethyl)-amino]propionamide, N-hydroxy-3-[(4-trifluoromethylbenzenesulfonyl)-(2-thiophenethyl)-amino]propionamide, N-hydroxy-3-[(4-trifluoromethoxybenzenesulfonyl)-(2-thiophenethyl)-amino]propionamide, N-hydroxy-3-[(2-thiophenethyl)-(3-(N'-hydroxyamidino)benzenesulfonyl)-amino]- propionamide, N-hydroxy-3-[(2-(N'-hydroxyamidino) benzenesulfonyl)-(2-thiophenethyl)-amino]propionamide, N-hydroxy-3-[(2-thiophenethyl)-(4-methylsulfonylbenzenesulfonyl)-amino]-propionamide, N-hydroxy-3-[(2-methylsulfonylbenzenesulfonyl)-(2-thiophenethyl)-amino]propionamide, and N-hydroxy-3-[(2-carbomethoxybenzenesulfonyl)-(2-thiophenethyl)-amino] propionamide.

30. The compound of claim 28 wherein a is two, b is two and c is zero.

31. The compound of claim 22 wherein $Ar^2$ is thienyl or thienyl independently substituted with one or more $Y^2$.

32. The compound of claim 31 having the structural formula:

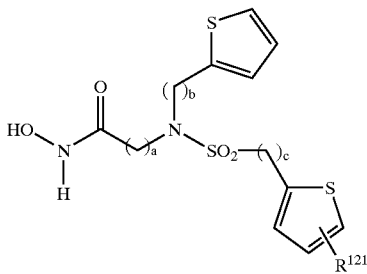

or pharmaceutically acceptable salts thereof, wherein:
$R^{121}$ is selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', tetrazol-5-yl, and —NR'—C(O)—OR';
R' is selected from the group consisting of —H, (C$_1$–C$_8$) alkyl, (C$_2$–C$_8$) alkenyl and (C$_2$–C$_8$) alkynyl; and
R" is (C$_5$–C$_{10}$) aryl.

33. The compound of claim 32 selected from the group consisting of FG 1417, FG 1419, FG 1425, and FG 1472.

34. The compound of claim 31 wherein a is two, b is two and c is zero.

35. The compound of claim 1 having the structural formula:

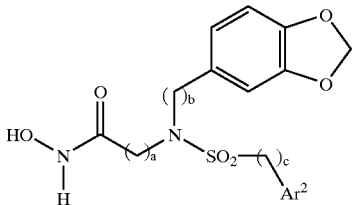

or pharmaceutically acceptable salts thereof.

36. The compound of claim 35 wherein:
$Ar^2$ is selected from the group consisting of phenyl, phenyl independently mono- or di-substituted with $Y^2$, 5–10 membered heteroaryl and 5–10 membered heteroaryl mono- or di-substituted with $Y^2$.

37. The compound of claim 35 wherein a is two, b is one and c is zero.

38. The compound of claim 35 wherein $Ar^2$ is selected from the group consisting of thienyl, 2,1,3-benzothiadiazolyl, imidazolyl, and 1,7-thiazopyrrolizinyl.

39. The compound of claim 35 selected from the group consisting of FG 1367, FG 1361, FG 1362, FG 1363, FG 1365, FG 1371, and FG 1473.

40. The compound of claim 35 having the structural formula:

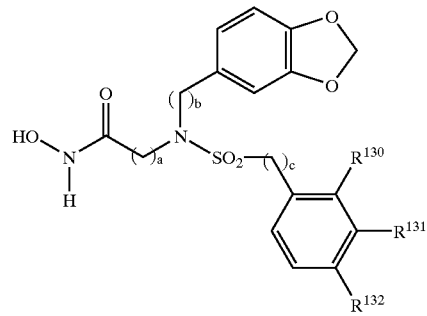

or pharmaceutically acceptable salts thereof, wherein
wherein $R^{130}$, $R^{131}$ and $R^{132}$ are each independently selected from the group consisting of —R', —OR', —OR", —SR', —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', tetrazol-5-yl, and —NR'—C(O)—OR';
each R' is independently selected from the group consisting of —H, (C$_1$–C$_8$) alkyl, (C$_2$–C$_8$) alkenyl and (C$_2$–C$_8$) alkynyl; and
R" is selected from the group consisting of phenyl and phenyl independently mono-, di-substituted or tri-substituted with halogen or —CN, with the proviso that when a and b are each one then c is other than zero.

41. The compound of claim 40 selected from the group consisting of N-hydroxy-3-[(3,4-methylenedioxybenzyl)-(4-methoxybenzenesulfonyl)-amino]-propionamide, N-hydroxy-3-[(4-carboxybenzenesulfonyl)-(3,4-methylenedioxybenzyl)-amino]propionamide, N-hydroxy-3-[(3-carboxybenzenesulfonyl)-(3,4-methylenedioxybenzyl)-amino]propionamide, N-hydroxy-3-[(3,4-methylenedioxybenzyl)-(4-(N'-hydroxyamidino) benzenesulfonyl)-amino]-propionamide, N-hydroxy-3-[(3,4-methylenedioxybenzyl)-(4-acetylaminobenzenesulfonyl)-amino]-propionamide, N-hydroxy-3-[(benzylsulfonyl)-(3,4-methylenedioxybenzyl)-amino]propionamide, N-hydroxy-3-[(3,4-dimethoxybenzenesulfonyl)-(3,4-methylenedioxybenzyl)-amino]propionamide, N-hydroxy-3-[(3,4-methylenedioxybenzyl)-(4-n-butoxybenzenesulfonyl)-amino]-propionimide, N-hydroxy-3-[(4-(2-cyano-3-chlorophenoxy)benzenesulfonyl)-(3,4-methylenedioxybenzyl)-amino]propionamide, N-hydroxy-3-[(4-trifluoromethylbenzenesulfonyl)-(3,4-methylenedioxybenzyl)-amino]propionamide, N-hydroxy-3-[(4-trifluoromethoxybenzenesulfonyl)-(3,4-metbylenedioxybenzyl)-amino]propionamide, N-hydroxy-3-[(3-(N'-hydroxyamidino)benzenesulfonyl)-(3,4-methylenedioxybenzyl)-amino]propionamide, N-hydroxy-3-[(2-(N'-hydroxyamidino)benzenesulfonyl)-(3,4-methylenedioxybenzyl)-amino]propionamide, N-hydroxy-3-[(3,4-methylenedioxybenzyl)-(4-methylsulfonylbenezene)-amino]-propionamide, N-hydroxy-3-[(2-methylsulfonylbenzenesulfonyl)-(3,4-methylenedioxybenzyl)-amino]propionamide, and N-hydroxy-3-[(2-carbomethoxybenzenesulfonyl)-(3,4-methylenedioxybenzyl)-amino]propionamide.

42. The compound of claim 1 wherein $Ar^1$ is benzodioxole and $Ar^2$ is thienyl or thienyl independently substituted with one or more $Y^2$.

43. The compound of claim 42 having the structural formula:

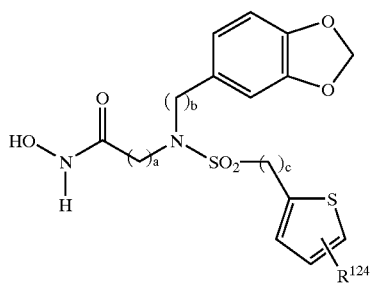

or pharmaceutically acceptable salts thereof wherein $R^{124}$ is selected from the group consisting of —R', —OR', —OR", —SR', SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', tetrazol-5-yl, and —NR'—C(O)—OR';

each R' is independently selected from the group consisting of —H, (C$_1$–C$_8$) alkyl, (C$_2$–C$_8$) alkenyl and (C$_2$–C$_8$) alkynyl; and each R" is selected from the group consisting of phenyl and phenyl independently mono-, di-substituted or tri-substituted with halogen or —CN.

44. The compound of claim 43 wherein a is two, b is one and c is zero.

45. The compound of claim 43 selected from the group consisting of N-hydroxy-3-[(3,4-methylenedioxybenzyl)-(5-bromothiophene-2-sulfonyl)-amino]-propionamide, N-hydroxy-3-[(3,4-methylenedioxybenzyl)-(5-benzene-sulonylthiophene-2-sulfonyl)-amino]-propionamide, N-hydroxy-3-[(3,4-methylenedioxybenzyl)-(thiophene-2-sulfonyl)-amino]-propionamide, and N-hydroxy-3-[(5-(N'-hydroxyaminocarbonyl)thiophen-2-sulfonyl)-(3,4-methylenedioxybenzyl)-amino]propionamide.

46. A pharmaceutical composition comprising the compound of claim 1 and a pharmaceutically acceptable carrier, diluent or excipient.

47. A method of treating a disease related to inappropriate or unregulated production of collagen, said method comprising the step of administering to a subject in need thereof an effective amount of a compound according to claim 1.

48. The method of treating a fibrotic disorder selected from the group consisting of hepatic cirrhosis and arthritis, said method comprising the step of administering to a subject in need thereof an effective amount of a compound according to claim 1.

49. The method of inhibiting an MMP, said method comprising the step of administering to a subject an effective amount of a compound according to claim 1.

* * * * *